United States Patent
Jiricek et al.

(10) Patent No.: US 9,447,039 B2
(45) Date of Patent: Sep. 20, 2016

(54) INDOLE CARBOXAMIDE DERIVATIVES AND USES THEREOF

(71) Applicants: Jan Jiricek, Singapore (SG); Ravinder Reddy Kondreddi, Singapore (SG); Paul William Smith, Singapore (SG)

(72) Inventors: Jan Jiricek, Singapore (SG); Ravinder Reddy Kondreddi, Singapore (SG); Paul William Smith, Singapore (SG)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/420,074

(22) PCT Filed: Sep. 5, 2013

(86) PCT No.: PCT/IB2013/058318
§ 371 (c)(1),
(2) Date: Feb. 6, 2015

(87) PCT Pub. No.: WO2014/037900
PCT Pub. Date: Mar. 13, 2014

(65) Prior Publication Data
US 2015/0175539 A1 Jun. 25, 2015

Related U.S. Application Data

(60) Provisional application No. 61/698,033, filed on Sep. 7, 2012.

(51) Int. Cl.
| | |
|---|---|
| *C07D 209/12* | (2006.01) |
| *C07D 209/42* | (2006.01) |
| *A61K 31/4045* | (2006.01) |
| *A61K 31/407* | (2006.01) |
| *A61K 31/454* | (2006.01) |
| *A61K 31/5377* | (2006.01) |
| *A61K 45/06* | (2006.01) |
| *C07D 491/056* | (2006.01) |

(52) U.S. Cl.
CPC ........... *C07D 209/42* (2013.01); *A61K 31/407* (2013.01); *A61K 31/4045* (2013.01); *A61K 31/454* (2013.01); *A61K 31/5377* (2013.01); *A61K 45/06* (2013.01); *C07D 491/056* (2013.01)

(58) Field of Classification Search
CPC .................................................. C07D 209/12
See application file for complete search history.

(56) References Cited

U.S. PATENT DOCUMENTS

| | | |
|---|---|---|
| 2004/0077646 A1 | 4/2004 | Bamberg |
| 2005/0119486 A1 | 6/2005 | Ohta |
| 2010/0160303 A1 | 6/2010 | Liu |

FOREIGN PATENT DOCUMENTS

| | | |
|---|---|---|
| JP | 2012-107001 | 6/2012 |
| WO | WO 03/035621 | 5/2003 |
| WO | WO 03/048123 | 6/2003 |
| WO | WO 2006/067392 | 6/2006 |
| WO | WO 2007/115315 | 10/2007 |
| WO | WO 2009/063495 | 5/2009 |
| WO | WO 2010/099166 | 9/2010 |
| WO | WO 2011/072275 | 6/2011 |

OTHER PUBLICATIONS

Kremer et al., "Current Status and Future Development of Antitubercular Chemotherapy" Expert Opinion 11:1033-1049 (2002).
Frieden et al., "Tuberculosis" The Lancet 362:887-899 (2003).
Diacon et al., "The Diarylquinoline TMC207 for Multidrug-Resistant Tuberculosis" The New England Journal of Medicine 360(23):2397-2405 (2009).
Davies and Yew, "Recent Developments in the Treatment of Tuberculosis" Expert Opinion Investig. Drugs 12:1297-1312 (2003).
Uhlin et al., "Adjunct Immunotherapies for Tuberculosis" Journal of Infectious Diseases 205(Suppl 2):S325-334 (2012).
Liu et al., "Rearrangment of 3,3-Disubstituted Indolenines and Synthesis of 2,3-Substituted Indoles" Organic Letters 8(25):5769-5771 (2006).
Bonnamour and Bolm, "Iron(II) Triflate as Catalyst for the Synthesis of Indoles by Intramolecular C-H Amination" Organic Letters 13(8):2012-2014 (2011).
Pethe et al., "A Chemical Genetic Screen in *Mycobacterium tuberculosis* Identifies Carbon-Source-Dependent Growth Inhibitors Devoid of in Vivo Efficacy" Nature Communications 1(57):1-8 (2010).

(Continued)

*Primary Examiner* — Michael Barker
*Assistant Examiner* — Karen Cheng
(74) *Attorney, Agent, or Firm* — Chihang Amy Smith; Genomics Institute of the Novartis Research Foundation

(57) ABSTRACT

A compound of Formula (I) is provided that has been shown to be useful for treating a disease, disorder or syndrome that is mediated by the transportation of essential molecules in the mmpL3 pathway:

(I)

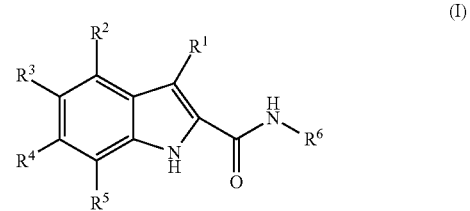

wherein $R^1$, $R^2$, $R^3$, $R^4$, $R^5$ and $R^6$ are as defined herein.

32 Claims, No Drawings

(56) References Cited

OTHER PUBLICATIONS

Wayne, L. G. In *Mycobacterium tuberculosis* Protocols, Parish, T., Stoker, N. G., Eds., Humana Press, Totowa, NJ, pp. 247-269 (2001).
Domenech et al., "Contribution of the *Mycobacterium tuberculosis* MmpL Protein Family to Virulence and Drug Resistance" Infection Immunity 73(6):3492-3501 (2005).
Grzegorzewicz et al., "Inhibition of Mycolic Acid Transport Across the *Mycobacterium tuberculosis* Plasma Membrane", Nature Chemical Biology 8(4):334-341 (2012).
Tahlan et al., "SQ109 Targets MmpL3, a Membrane Transporter of Trehalose Monomycolate Involved in Mycolic Acid Donation to the Cell Wall Core of *Mycobacterium tuberculosis*" Antimicrobial Agents Chemotherapy 56(4):1797-1809 (2012).
La Rosa et al., "MmpL3 is the Cellular Target of the Antitubercular Pyrrole Derivative BM212" Antimicrobial Agents Chemotherapy 56(1):324-331 (2012).
Scherman et al., "Screening a Library of 1600 Adamantyl Ureas for Anti-*Mycobacterium tuberculosis* Activity in vitro and for Better Physical Chemical Properties for Bioavailability" Bioorganic and Medicinal Chemistry 20(10):3255-3262 (2012).
Stanley et al., "Identification of Novel Inhibitors of *M. tuberculosis* Growth Using Whole Cell Based High-Throughput Screening" ACS Chemical Biology 7:1377-1384 (2012).
Mahboobi et al.,"Bis (1H-2-indolyl)-methanones as a Novel Class of Inhibitors of the Platelet Derived Growth Factor Receptor Kinase" Journal of Medicinal Chemistry, American Chemical Society US 45(5):1002-1018, Jan. 1, 2002.
Mueller et al., "Identification and Biochemical Characterization of Small-Molecule Inhibitors of West Nile Virus Serine Protease by a High-Throughput Screen" Antimicrobial Agents and Chemotherapy 53(1):341, 2009.
Onajole et al., "Preliminary Structure-Activity Relationships and Biological Evaluation of Novel Antitubercular Indolecarboxamide Derivatives Against Drug-Susceptible and Drug-Resistant *Mycobacterium tuberculosis* Strains" J. Med. Chem. 56:4093-4103, Apr. 23, 2013.
CAS Registry No. 1322523-21-6, Aug. 24, 2011.
CAS Registry No. 1320804-31-6, Aug. 21, 2011.
CAS Registry No. 1318010-92-2, Aug. 15, 2011.
CAS Registry No. 1279502-37-2, Apr. 13, 2011.
CAS Registry No. 1179375-35-9, Sep. 2, 2009.
CAS Registry No. 930042-39-0, Apr. 13, 2007.
CAS Registry No. 921084-03-9, Feb. 15, 2007.

INDOLE CARBOXAMIDE DERIVATIVES AND USES THEREOF

CROSS-REFERENCE TO RELATED APPLICATIONS

This application is the U.S. National Stage of International Application No. PCT/IB2013/058318, filed Sep. 5, 2013, which claims the benefit of priority to U.S. Provisional Application No. 61/698,033, filed Sep. 7, 2012, the contents of which are incorporated herein by reference.

FIELD OF THE INVENTION

The present invention relates to indole carboxamide derivatives, pharmaceutical formulations thereof, and their use for the treatment of tuberculosis, in particular multi-drug resistant (MDR) and extensively drug-resistant (XDR) tuberculosis.

BACKGROUND

Until tuberculosis is controlled worldwide, it will continue to be a major killer in less developed countries and a constant threat in most of the more-developed countries. It has been reported that 2 billion people are latently infected and 1 in 10 latent infections will progress to the active disease. *Mycobacterium tuberculosis*, the causative agent for tuberculosis (TB), infects one-third of the world's population, resulting in eight to nine million new cases of active TB and two million deaths each year (Kremer, et al., *Expert Opin. Investig. Drugs,* 11, 1033-1049 (2002); and Frieden, T. R., et al., *The Lancet,* 362, 887-99 (2003); and Diacon, Andreas H., et al., *N Eng J Med.* 360(23), 2397-2405 (2009)). TB is presently treated with a four-drug combination (isoniazid, rifampin, pyrazinamide, ethambutol) that imposes a lengthy 6-9 month treatment course, often under the direct observation of a healthcare provider (Davies, et al., *Expert Opin. Investig. Drugs.* 12, 1297-1312 (2003)). The major shortcoming of this regimen is the long treatment time (up to 2 years) and high failure rate, which makes patient compliance and proper implementation a challenge. More than two-thirds of the TB patients do not receive full and proper TB treatment, which results in a high relapse rate and emergence of drug resistance.

About 4% of the TB cases worldwide are multiple-drug resistant (MDR), e.g., resistant to both isoniazid and rifampicin. XDR-TB, an abbreviation for extensively drug-resistant tuberculosis (TB), is a form of TB which is resistant to at least four of the core anti-TB drugs. XDR-TB involves resistance to the two most powerful anti-TB drugs, isoniazid and rifampicin (MDR-TB), in addition to resistance to any of the fluoroquinolones (such as ofloxacin or moxifloxacin) and to at least one of three injectable second-line drugs (amikacin, capreomycin or kanamycin). Although XDR-TB is more rare, 77 countries worldwide had reported at least one case by the end of 2011. The World Health Organization (WHO) estimates that there are about 650,000 MDR-TB cases in the world at any one time. The number of cases of MDR tuberculosis is alarmingly increasing worldwide, with MDR detected in up to 35% of newly diagnosed cases and in 76.5% of patients who had previously been treated for tuberculosis. XDR tuberculosis was identified in 14% of patients with MDR, with patients less than 35 years old exhibiting an odds of MDR tuberculosis that was 2 times that for individuals aged over 35 years. See, Uhlin, M., et al., *J Infect Dis,* 205(Suppl 2), S325-334 (2012).

MDR-TB and XDR-TB both take substantially longer to treat than ordinary (drug-susceptible) TB, and require the use of second-line anti-TB drugs, which are more expensive and have more side-effects than the first-line drugs used for drug-susceptible TB. Treatment is complex and requires longer use of more-expensive, less effective, and toxic anti-tuberculosis drugs, which results in high morbidity and mortality.

There still remains several issues that need to be addressed in both standard TB therapies as well as MDR/XDR resistant therapies. For example, there is a need to shorten the duration of standard TB therapy which could increase compliance and thus reduce resistance. For MDR/XDR resistant TB, there is an unmet need to find novel chemotypes that are active against MDR and XDR TB that enhance cure rate, reduce adverse effects, shorten treatment time, and improve patient compliance which reduces resistance.

SUMMARY

The compounds described herein have been shown to be useful in the treatment of tuberculosis, in particular multi-drug resistant (MDR) and extensively drug-resistant (XDR) tuberculosis.

One aspect of the present invention provides compounds of Formula (I)

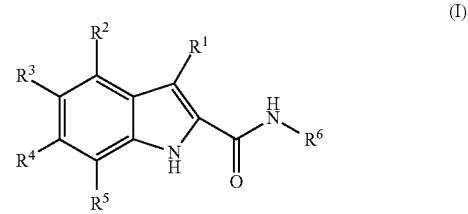

wherein
$R^1$ is H or methyl;
$R^2$ is H, methyl, halo, cyano, trifluoromethyl, or methoxy;
$R^3$ is H, methyl, or methoxy;
$R^4$ is H, methyl, halo, cyano, trifluoromethyl, methoxy, —$(O(CH_2)_m)_n$-morpholinyl, piperidinyl, (($C_1$-$C_4$)alkyl)NH—, or (phenyl)NH—, where m is 1 or 2 and n is 0 or 1; or $R^3$ and $R^4$ taken together with the aromatic carbon atoms to which they are attached form a fused 1,3-dioxolo group;
$R^5$ is H or halo;
provided that $R^2$, $R^3$, $R^4$ and $R^5$ are not all hydrogen;
$R^6$ is
(i) ($C_4$-$C_6$)alkyl, where said ($C_4$-$C_6$)alkyl is optionally substituted with phenyl which is optionally substituted with one to two substituents each independently selected from ($C_1$-$C_4$)alkyl, fluoro-substituted ($C_1$-$C_4$)alkyl, methoxy, hydroxy($C_1$-$C_4$)alkyl, methoxy($C_1$-$C_4$)alkyl, ethynyl, cyano, halo, or hydroxy;
(ii) ($C_5$-$C_7$)cycloalkyl, or —$CH_2$—($C_5$-$C_7$)cycloalkyl, where said ($C_5$-$C_7$)cycloalkyls are optionally substituted with one to two substituents each independently selected from ($C_1$-$C_4$)alkyl, fluoro-substituted ($C_1$-$C_4$)alkyl, methoxy, hydroxy($C_1$-$C_4$)alkyl, methoxy($C_1$-$C_4$)alkyl, ethynyl, cyano, halo, or hydroxy, provided that $R^6$ is not an unsubstituted cyclohexyl, when $R^2$ and $R^4$ are both methyl;
(iii) spiral($C_8$-$C_{11}$)cycloalkyl; or (iv) phenyl, where said phenyl is optionally substituted with one to two substituents each independently selected from $(C_1-C_4)$alkyl, fluoro-substituted $(C_1-C_4)$alkyl, methoxy, hydroxy$(C_1-C_4)$alkyl, methoxy $(C_1-C_4)$alkyl, ethynyl, cyano, halo, or hydroxy, provided that $R^6$ is not an unsubstituted phenyl, when $R^2$ and $R^4$ are both methyl;

or a pharmaceutically acceptable salt thereof.

In one embodiment, the compound of Formula (I) is provided wherein $R^1$ is H; $R^2$ is H, methyl, trifluoromethyl, methoxy, chloro, bromo, fluoro, or cyano; $R^3$ is H or methoxy; $R^4$ is H, methyl, trifluoromethyl, methoxy, chloro, bromo, fluoro, cyano, —O(CH$_2$)$_2$)-morpholinyl, ((C$_1$-C$_4$)alkyl)NH—, or (phenyl)NH—; or $R^3$ and $R^4$ taken together with the aromatic carbon atoms to which they are attached form a fused 1,3-dioxolo group; $R^5$ is H or chloro; provided that $R^2$, $R^3$, $R^4$ and $R^5$ are not all hydrogen; $R^6$ is (i) C$_5$ alkyl; (ii) (C$_5$-C$_7$)cycloalkyl, or —CH$_2$-(cyclohexyl), where said (C$_5$-C$_7$)cycloalkyl is optionally substituted with one to two substituents each independently selected from halo, methyl, isopropyl, fluoro-substituted methyl, methoxy(C$_1$-C$_4$)alkyl, ethynyl, or cyano, provided that $R^6$ is not an unsubstituted cyclohexyl, when $R^2$ and $R^4$ are both methyl; (iii) spiro[2.5] octan-6-yl; or (iv) phenyl substituted with halo or methyl; or a pharmaceutically acceptable salt thereof.

In another embodiment, a compound of Formula (I) is provided wherein $R^1$ is H; $R^2$ is H, methyl, trifluoromethyl, chloro, bromo, fluoro, or cyano; $R^3$ is H; $R^4$ is H, methyl, trifluoromethyl, chloro, bromo, fluoro, cyano, or (phenyl)NH—; $R^5$ is H or chloro; provided that $R^2$, $R^3$, $R^4$ and $R^5$ are not all hydrogen; $R^6$ is (C$_5$-C$_7$)cycloalkyl or —CH$_2$-(cyclohexyl), where said (C$_5$-C$_7$)cycloalkyl is optionally substituted with one to two substituents each independently selected from halo, methyl, isopropyl, fluoro-substituted methyl, or ethynyl, provided that $R^6$ is not an unsubstituted cyclohexyl, when $R^2$ and $R^4$ are both methyl; or a pharmaceutically acceptable salt thereof.

Representative compounds of Formula (I) include: N-cycloheptyl-4,6-dimethyl-1H-indole-2-carboxamide; 4-bromo-N-cycloheptyl-6-(trifluoromethyl)-1H-indole-2-carboxamide; 4,6-dimethyl-N-(2-methylcyclohexyl)-1H-indole-2-carboxamide; N-(cyclohexylmethyl)-4,6-dimethyl-1H-indole-2-carboxamide; 4,6-dimethyl-N-((1R,2S)-2-methylcyclohexyl)-1H-indole-2-carboxamide; 4,6-dimethyl-N-((1S,2R)-2-methylcyclohexyl)-1H-indole-2-carboxamide; N-((1R,2S,3S)-2,3-dimethylcyclohexyl)-4,6-dimethyl-1H-indole-2-carboxamide; N-((1R,2S,3R)-2,3-dimethylcyclohexyl)-4,6-dimethyl-1H-indole-2-carboxamide; N-(trans-4-isopropylcyclohexyl)-4,6-dimethyl-1H-indole-2-carboxamide; N-((1S,2R,3S)-2,3-dimethylcyclohexyl)-4,6-dimethyl-1H-indole-2-carboxamide; 4,6-difluoro-N-(4-methylcyclohexyl)-1H-indole-2-carboxamide; 4,6-dichloro-N-(4-methylcyclohexyl)-1H-indole-2-carboxamide; N-(4-methylcyclohexyl)-4,6-bis(trifluoromethyl)-1H-indole-2-carboxamide; N-((1S,2R,3R)-2,3-dimethylcyclohexyl)-4,6-dimethyl-1H-indole-2-carboxamide; 4,6-dichloro-N-((1R,2S)-2-methylcyclohexyl)-1H-indole-2-carboxamide; 4,6-dimethyl-N-((1R,2S)-2-methylcyclopentyl)-1H-indole-2-carboxamide; 4,6-dimethyl-N-(2-(trifluoromethyl)cyclohexyl)-1H-indole-2-carboxamide; N-(4-isopropylcyclohexyl)-4,6-dimethyl-1H-indole-2-carboxamide; N-(2-isopropylcyclohexyl)-4,6-dimethyl-1H-indole-2-carboxamide; 4,6-dichloro-N-(4,4-difluorocyclohexyl)-1H-indole-2-carboxamide; 4,6-dichloro-N-(cis-4-methylcyclohexyl)-1H-indole-2-carboxamide; 4,6-dichloro-N-(trans-4-methylcyclohexyl)-1H-indole-2-carboxamide; 4,6-dichloro-N-(4,4-dimethylcyclohexyl)-1H-indole-2-carboxamide; 4,6-dichloro-N-(4-(trifluoromethyl)cyclohexyl)-1H-indole-2-carboxamide; N-(4,4-Dimethylcyclohexyl)-4,6-difluoro-1H-indole-2-carboxamide; 4,6-dichloro-N-(4-(fluoromethyl)cyclohexyl)-1H-indole-2-carboxamide; 4,6-dichloro-N-(1-ethynylcyclohexyl)-1H-indole-2-carboxamide; 6-chloro-N-(4-methylcyclohexyl)-1H-indole-2-carboxamide; 6,7-dichloro-N-(4-methylcyclohexyl)-1H-indole-2-carboxamide; 7-chloro-N-(4-methylcyclohexyl)-1H-indole-2-carboxamide; 4-chloro-N-(4-methylcyclohexyl)-1H-indole-2-carboxamide; 6-methyl-N-((1R,2S)-2-methylcyclohexyl)-1H-indole-2-carboxamide; 4-methyl-N-((1R,2S)-2-methylcyclohexyl)-1H-indole-2-carboxamide; 4-bromo-N-((1R,2S)-2-methylcyclohexyl)-1H-indole-2-carboxamide; 6-bromo-N-((1R,2S)-2-methylcyclohexyl)-1H-indole-2-carboxamide; 4-cyano-N-((1R,2S)-2-methylcyclohexyl)-1H-indole-2-carboxamide; 6-cyano-N-((1R,2S)-2-methylcyclohexyl)-1H-indole-2-carboxamide; 6-bromo-4-methyl-N-((1R,2S)-2-methylcyclohexyl)-1H-indole-2-carboxamide; 4-bromo-6-methyl-N-((1R,2S)-2-methylcyclohexyl)-1H-indole-2-carboxamide; 6-cyano-4-methyl-N-((1R,2S)-2-methylcyclohexyl)-1H-indole-2-carboxamide; 4-cyano-6-methyl-N-((1R,2S)-2-methylcyclohexyl)-1H-indole-2-carboxamide; 4-methyl-N-((1R,2S)-2-methylcyclohexyl)-6-(phenylamino)-1H-indole-2-carboxamide; 6-chloro-4-fluoro-N-(4-methylcyclohexyl)-1H-indole-2-carboxamide; 4-chloro-6-fluoro-N-(4-methylcyclohexyl)-1H-indole-2-carboxamide; 4,6-dicyano-N-(trans-4-methylcyclohexyl)-1H-indole-2-carboxamide; 4,6-difluoro-N-(trans-4-methylcyclohexyl)-1H-indole-2-carboxamide; 5,6-dichloro-N-(4-methylcyclohexyl)-1H-indole-2-carboxamide; 4,6-dicyano-N-(4-methylcyclohexyl)-1H-indole-2-carboxamide; and 4,6-dichloro-N-(1-ethynylcyclohexyl)-1H-indole-2-carboxamide; or a pharmaceutically acceptable salt thereof.

Compounds of particular interest include: 4,6-difluoro-N-(4-methylcyclohexyl)-1H-indole-2-carboxamide; 4,6-dichloro-N-(4-methylcyclohexyl)-1H-indole-2-carboxamide; N-(4-methylcyclohexyl)-4,6-bis(trifluoromethyl)-1H-indole-2-carboxamide; 4,6-dichloro-N-((1R,2S)-2-methylcyclohexyl)-1H-indole-2-carboxamide; 4-bromo-N-cycloheptyl-6-(trifluoromethyl)-1H-indole-2-carboxamide; 5,6-dichloro-N-(4-methylcyclohexyl)-1H-indole-2-carboxamide; 4,6-dichloro-N-(cis-4-methylcyclohexyl)-1H-indole-2-carboxamide; 4,6-dichloro-N-(trans-4-methylcyclohexyl)-1H-indole-2-carboxamide; 4,6-dicyano-N-(4-methylcyclohexyl)-1H-indole-2-carboxamide; 4,6-Dichloro-N-(4,4-dimethylcyclohexyl)-1H-indole-2-carboxamide; 6-chloro-4-fluoro-N-(4-methylcyclohexyl)-1H-indole-2-carboxamide; 4-chloro-6-fluoro-N-(4-methylcyclohexyl)-1H-indole-2-carboxamide; 4,6-dichloro-N-(4-(trifluoromethyl)cyclohexyl)-1H-indole-2-carboxamide; N-(4,4-Dimethylcyclohexyl)-4,6-difluoro-1H-indole-2-carboxamide; 4,6-dichloro-N-(4-(fluoromethyl)cyclohexyl)-1H-indole-2-carboxamide; and 4,6-difluoro-N-(trans-4-methylcyclohexyl)-1H-indole-2-carboxamide; or a pharmaceutically acceptable salt thereof.

Of particular interest are 4,6-Dichloro-N-(4,4-dimethylcyclohexyl)-1H-indole-2-carboxamide; and N-(4,4-Dimethylcyclohexyl)-4,6-difluoro-1H-indole-2-carboxamide; or a pharmaceutically acceptable salt thereof.

One compound of interest has the following structure:

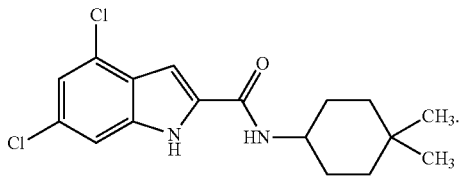 [SMILES: CC1(C)CCC(NC(=O)c2cc3c(Cl)cc(Cl)cc3[nH]2)CC1]

Another compound of interest has the following structure

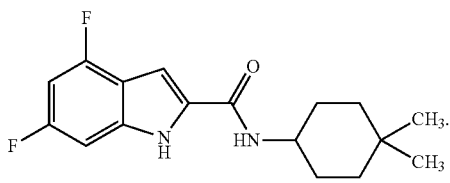 [SMILES: CC1(C)CCC(NC(=O)c2cc3c(F)cc(F)cc3[nH]2)CC1]

Another aspect of the present invention includes a pharmaceutical composition comprising a compound of Formula (I) compromising any one of embodiments described above, or a pharmaceutically acceptable salt thereof, and a pharmaceutically acceptable carrier or excipient. The pharmaceutical composition may further comprise at least one additional pharmaceutical agent described herein below. Additional pharmaceutical agents of particular interest are antituberculosis agents. Examples of antituberculosis agent include isoniazid, rifampicin, pyrazinamide, ethambutol, streptomycin, kanamycin, amikacin, capreomycin, ofloxacin, levofloxacin, moxifloxacin, cycloserine, para-aminosalicylic acid, ethioamide, prothionamide, thioacetazone clofazimine, amoxicilin with clavulanate, imipenem, linezolid, clarithromycin, and thioridazine.

In yet another aspect of the present invention, a method is provided for treating a disease, disorder or syndrome mediated by the transportation of essential molecules in the mmpL3 pathway comprising the step of administering to a patient (in particular, a human) in need thereof, a compound of Formula (I) including any of the embodiments described herein, or a pharmaceutically acceptable salt thereof. The disease, disorder or syndrome of particular interest is tuberculosis. The essential molecule of interest is trehalose monomycolate. In a particular useful embodiment, the human has (i) a sputum smear-positive, sputum smear-negative, or extrapulmonary tuberculosis; (ii) tuberculosis caused by drug resistant *Mycobacterium tuberculosis* complex (*M. tuberculosis*) organisms; or (iii) tuberculosis combined with human immunodeficiency virus (HIV) infection. The compound may be administered as a pharmaceutical composition described herein Another aspect of the present invention includes a compound according to Formula (I), for use in therapy (e.g., the use of a compound of Formula (I) for the treatment of a disease, disorder, or syndrome mediated by the transportation of essential molecules (e.g., trehalose monomycolate (TMM)) in the mmpL3 pathway.

In yet another aspect of the present invention, a method is provided for treating a disease, disorder or syndrome mediated by the transportation of essential molecules in the mmpL3 pathway comprising the step of administering to a patient (in particular, a human) in need thereof (i) a first composition comprising any one of the compounds according to Claims 1 through 8, or a pharmaceutically acceptable salt thereof, and a pharmaceutically acceptable carrier or excipient; and (ii) a second composition comprising at least one additional pharmaceutical agent and a pharmaceutically acceptable carrier or excipient. The disease, disorder or syndrome of particular interest is tuberculosis. The essential molecule of particular interest is trehalose monomycolate. In one embodiment, the human has (i) a sputum smear-positive, sputum smear-negative, or extrapulmonary tuberculosis; (ii) tuberculosis caused by drug resistant *Mycobacterium tuberculosis* complex (*M. tuberculosis*) organisms; or (iii) tuberculosis combined with human immunodeficiency virus (HIV) infection. The first and second compositions may be administered simultaneously; or sequentially in any order.

DEFINITIONS

As used herein, the terms "alkyl" refers to a hydrocarbon radical of the general formula $C_nH_{2n+1}$. The alkane radical may be straight or branched. For example, the term "($C_1$-$C_6$)alkyl" refers to a monovalent, straight, or branched aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like). Similarly, the alkyl portion (i.e., alkyl moiety) of an alkoxy, acyl (e.g., alkanoyl), alkylamino, dialkylamino, and alkylthio group has the same definition as above.

"Halo-substituted alkyl" refers to an alkyl group, as defined above, substituted with at least one halogen atom. For example, when the halogen atom is fluoro, common haloalkyl groups include fluoromethyl, difluoromethyl, trifluoromethyl, 2,2,2-trifluoroethyl, 2,2,2,1,1-pentafluoroethyl, and the like. Mixed halogen substitution are also included (e.g., chlorofluoromethyl).

The term "alkynyl" refers to a monovalent group derived from a hydrocarbon having at least one carbon-carbon triple bond. The term "$C_2$-$C_6$-alkynyl" refers to a monovalent group derived from a hydrocarbon having two to six carbon atoms and comprising at least one carbon-carbon triple bond. The alkynyl group can be unbranched or branched. Representative examples include ethynyl (HC≡C—), propynyl (e.g., $CH_3$—C≡C— and H—C≡C—$CH_2$—), butynyl (e.g., H—C≡C—CH($CH_3$)—, H—C≡C—$CH_2CH_2$—, $CH_3$—C≡C—$CH_2$—, and $CH_3$—$CH_2$—C≡C—), and so on.

The term "hydroxy-substituted alkyl" refers to an alkyl group, as defined above, substituted with one or more hydroxyl (—OH) groups (e.g., —$CH_2OH$, —CH(OH)—$CH_2OH$, —CH(OH)—$CH_3$, and so on). Preferably, the alkyl group is substituted with 1 to 2 hydroxyl groups, more preferably one hydroxyl group.

The term "methoxy-substituted alkyl" refers to an alkyl group, as defined above, substituted with one or more methoxy (—$OCH_3$) groups (e.g., —$CH_2OCH_3$, —CH($OCH_3$)$_2$, —CH($OCH_3$)—$CH_2OCH_3$, —CH($OCH_3$)—$CH_3$, and so on). Preferably, the alkyl group is substituted with 1 to 2 methoxy groups, more preferably one methoxy group.

"Halogen" or "halo" may be fluorine, chlorine, bromine or iodine (particularly useful halogens as substituents are fluorine, bromine, and chlorine, more particularly fluorine and chlorine).

The term "cycloalkyl" refers to a nonaromatic carbocyclic ring that is fully hydrogenated and exists as a monocyclic ring. Unless specified otherwise, the carbocyclic ring is generally a 3- to 8-membered ring. For example, a fully saturated cycloalkyl include groups such as cyclopropyl, cyclobutyl, cyclopentyl, cyclohexyl, and the like.

The term "spirocycloalkyl" refers to two nonaromatic carbocyclic rings that are connected through a common carbon atom. Unless specified otherwise, the individual carbocyclic rings are generally 3- to 6-membered rings or the joined rings are generally an 8- to 11-membered bicyclic ring system. For example, a spiral-$(C_8-C_{11})$cycloalkyl group includes groups such as spiro[2.5]octan-6-yl, spiro[3.5]nonan-7-yl, spiro[4.5]decan-8-yl, and spiro[5.5]undecan-3-yl. A particularly useful spirocycloalkyl group is spiro[2.5]octan-6-yl.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. The term "animal" refers to humans (male or female), companion animals (e.g., dogs, cats and horses), zoo animals, marine animals, birds and other similar animal species.

As used herein, a subject is "in need of" a treatment if such subject would benefit biologically, medically or in quality of life from such treatment (preferably, a human).

The phrase "pharmaceutically acceptable" indicates that the substance or composition must be compatible chemically and/or toxicologically, with the other ingredients comprising a formulation, and/or the mammal being treated therewith.

The term "compounds of the present invention" (unless specifically identified otherwise) refer to compounds of Formula (I) and salts thereof, as well as all stereoisomers (including diastereoisomers and enantiomers), rotamers, tautomers and isotopically labeled compounds (including deuterium substitutions), as well as inherently formed moieties (e.g., polymorphs, solvates and/or hydrates). For purposes of this invention, solvates and hydrates are generally considered compositions.

DETAILED DESCRIPTION

The present invention provides compounds and pharmaceutical formulations thereof that are useful in the treatment tuberculosis, in particular MDR or XDR resistant tuberculosis.

Compounds of the present invention may be synthesized by synthetic routes that include processes analogous to those well-known to those of skill in the art, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), or Beilsteins Handbuch der organischen Chemie, 4, Aufl. ed. Springer-Verlag, Berlin, including supplements (also available via the Beilstein online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amino, or carboxyl groups) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). Suitable carboxyl protecting groups (C(O)O-Pg) include alkyl esters (e.g., methyl, ethyl or t-butyl), benzyl esters, silyl esters, and the like. The need for such protection is readily determined by one skilled in the art. For a general description of protecting groups and their use, see T. W. Greene, Protective Groups in Organic Synthesis, John Wiley & Sons, New York, 1991.

Scheme 1 (below) describes a potential route for producing compounds of Formula (I). For a more detailed description, see the Example section below.

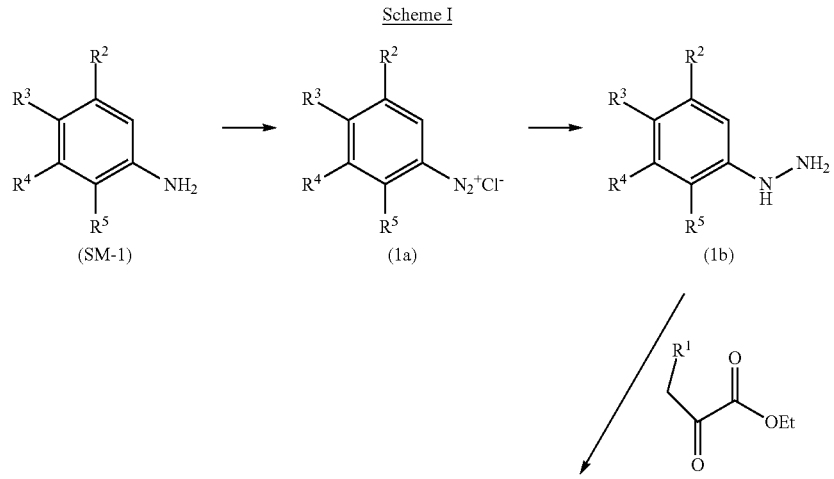

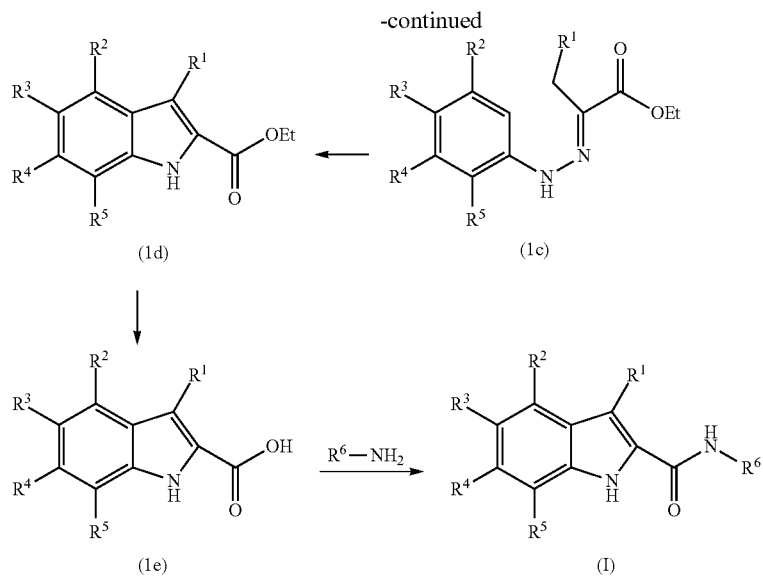

The aniline starting material (SM-1) is generally available commercially or can be prepared by methods well known to those of skill in the art. For example, each of the following compounds are available commercially from a variety of suppliers: 2-chloroaniline; 2-fluoroaniline; 2-bromoaniline; 3-chloroaniline; 3-fluoroaniline; 3-bromoaniline; 2,3-dichloroaniline; 2,3-difluoroaniline; 2,5-dichloroaniline; 2,5-difluoroaniline; 3,5-dichloroaniline; 3,5-difluoroaniline; 2,3,5-trichloroaniline; 2,3,5-difluoroaniline; 3-methylaniline; 3-trifluoromethylaniline; 3,4-dimethylaniline; 3,5-dimethylaniline; 3,5-bis(trifluoromethyl)aniline; 3,4,5-trimethylaniline; 3-aminobenzonitrile; 5-amino-1,3-benzenedicarbonitrile; 3-trifluoromethylaniline; m-anisidine; p-anisidine; 3,4-dimethoxyaniline; 3,5-dimethoxyaniline; 3,4,5-trimethoxyaniline; 3-morpholin-4-ylaniline; 3-(piperazin-1-yl)aniline; N-(m-aminophenyl)aniline; N1-methyl-1,3-benzenediamine; N1-ethyl-1,3-benzenediamine; N1-isopropyl-1,3-benzenediamine; N1-n-propyl-1,3-benzenediamine; N-(n-butyl)benzene-1,3-diamine; N-(sec-butyl)benzene-1,3-diamine; N-(iso-butyl)benzene-1,3-diamine; N-(t-butyl)benzene-1,3-diamine; 3,4-methylenedioxyaniline; 3-bromo-5-methylaniline; 3-amino-5-methylbenzonitrile; 3-chloro-5-fluoroaniline; spiro[2.5]octan-6-amine; spiro[3.5]nonan-7-amine; spiro[4.5]decan-8-amine; and spiro[5.5]undecan-3-amine. Other aniline derivatives can be made by modifying any of the above compounds using conventional chemistry well-known to those of skill in the art or using the synthesis described below in the Example section.

The desired aniline derivative (SM-1) is converted to its corresponding diazonium salt derivative (1a) using conditions and procedures well known to those of skill in the art. For example, the desired aniline derivative (SM-1) may be reacted with sodium nitrite in the presence of concentrated hydrogen chloride at cooled temperatures (e.g., −10° C.). The diazonium salt derivative (1a) can then be reduced to its corresponding hydrazine derivative (1b) using conventional chemistry. For example, the diazonium salt can be reduced using sulfur dioxide (or sodium sulfite) or stannous chloride in a highly acidic medium (e.g., concentrated aqueous hydrogen chloride). To introduce the $R^1$ group and prepare for cyclization to the indole ring system. When $R^1$ is hydrogen, the hydrazine derivative (1b) is reacted with ethyl pyruvate to form the pyruvate hydrazone derivative (1c). When $R^1$ is methyl, the hydrazine derivative (1b) is refluxed in ethanol with 2-oxo-butyric acid in the presence of p-toluenesulfonic acid (see e.g., WO 2007115315).

The desired indole derivative (1d) may then be prepared from (1c) using a Fischer indole synthesis (e.g., addition of a Brønsted or Lewis acids, or in the presence of polyphosphoric acid (PPA) at elevated temperatures). When $R^1$ is methyl, the indole derivative (1d) can alternatively be prepared using the preparation described by Liu, Kevin G; et al., in "Rearrangement of 3,3-disubstituted indolenines and synthesis of 2,3-substituted indoles" *Organic Letters*, 8(25), 5769-5771 (2006). The indole derivative (1d) can also be prepared using the synthesis described below in Scheme II.

Scheme II

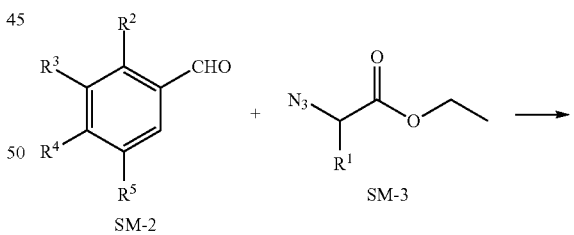

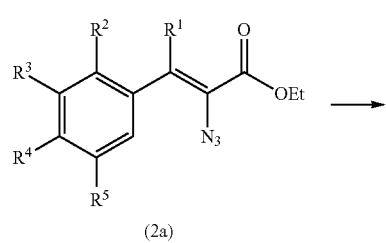

(2a)

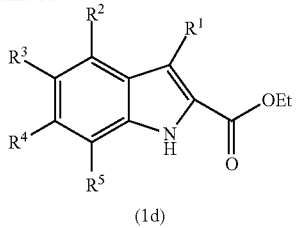

(1d)

The desired benzaldehyde derivative (SM-2) is condensed with the desired azide ester (SM-3) in the presence of a strong base (e.g., sodium ethoxide in ethanol). The azide intermediate (2a) is then cyclized to the indole at elevated temperatures in a non-protic solvent (e.g., xylene) to produce the desired indole ester (1d). Alternatively, the indole cyclization can be accomplished using an iron(II) triflate catalyst as described by J. Bonnamour, in *Org. Lett.*, 13, 2012-2014 (2011). The ester derivative (1d) can then be used in the synthesis described above to produce the desired compound of the present invention (I).

The ester group of indole derivative (1d) from either Scheme I or II can be hydrolyzed using conventional chemistry (e.g., treatment with lithium hydroxide in an aqueous medium at room temperature) to form the indole carboxylic acid derivative (1e).

Several carboxylic acid derivatives (1e) are also available commercially. Suitable commercially available carboxylic acid derivatives include: 4,6-dimethyl-1H-indole-2-carboxylic acid; 6-methyl-1H-indole-2-carboxylic acid; 4-methyl-1H-indole-2-carboxylic acid; 3,4-dimethyl-1H-indole-2-carboxylic acid; 4,6-dichloro-1H-indole-2-carboxylic acid; 6,7-dichloro-1H-indole-2-carboxylic acid; 4,7-dichloro-1H-indole-2-carboxylic acid; 6-chloro-1H-indole-2-carboxylic acid; 4-chloro-1H-indole-2-carboxylic acid; 5-chloro-1H-indole-2-carboxylic acid; 7-chloro-1H-indole-2-carboxylic acid; 4,6-difluoro-1H-indole-2-carboxylic acid; 4-fluoro-1H-indole-2-carboxylic acid; 6-fluoro-1H-indole-2-carboxylic acid; 4-chloro-6-fluoro-1H-indole-2-carboxylic acid; 6-chloro-4-fluoro-1H-indole-2-carboxylic acid; 6-bromo-1H-indole-2-carboxylic acid; 4-bromo-1H-indole-2-carboxylic acid; 4,6-dimethoxy-1H-indole-2-carboxylic acid; 5,6-dimethoxy-1H-indole-2-carboxylic acid; 5H-[1,3]dioxolo[4,5-f]indole-6-carboxylic acid; 4,5-dimethoxy-1H-indole-2-carboxylic acid; 6-methoxy-1H-indole-2-carboxylic acid; 4-methoxy-1H-indole-2-carboxylic acid; and 5-methoxy-1H-indole-2-carboxylic acid.

The final compound of Formula (I) can be prepared by traditional peptide coupling chemistry using the desired amino compound ($R^6$—$NH_2$). For example, the indole carboxylic acid derivative (1e) can be treated with the desired amine ($R^6$—$NH_2$) in the presence of 2-(7-aza-1H-benzotriazole-1-yl)-1,1,3,3-tetramethyluronium hexafluorophosphate (HATU) and N,N-diisopropylethylamine (DIPEA) in dimethylformamide (DMF) at room temperature. Other peptide coupling reagents and conditions may be used which are well known to those of skill in the art.

Suitable amines which are commerically available include: n-butylamine; sec-butylamine; iso-butylamine; t-butylamine; pentylamine; iso-pentylamine; neo-pentylamine; n-hexylamine; 4-methylpentylamine; 3-methylpentylamine; 2-methylpentylamine; 2,2-dimethylbutylamine; 2,3-dimethylbutylamine; 3,3-dimethylbutylamine; cyclohexylamine; 2-methylcyclohexylamine; cis-2-methylcyclohexylamine; trans-2-methylcyclohexylamine; 3-methylcyclohexylamine; 4-methylcyclohexylamine; cis-4-methylcyclohexylamine; trans-4-methylcyclohexylamine hydrochloride; 4-ethylcyclohexylamine; 2-isopropylcyclohexylamine; 4-isopropylcyclohexylamine; trans-4-isopropylcyclohexylamine; 2-(trifluoromethyl)cyclohexan-1-amine; (1S,2R)-2-(trifluoromethyl)cyclohexan-1-amine; 4-(trifluoromethyl)cyclohexan-1-amine; 2-aminocyclohexanol; (1R,2S)-2-aminocyclohexanol; (1R,2R)-2-aminocyclohexanol; 2-methoxycyclohexylamine; (1S,2R)-2-methoxycyclohexylamine; (1R,2S)-2-methoxycyclohexylamine; trans-2-methoxycyclohexylamine; 4,4-dimethylcyclohexylamine hydrochloride; 2-aminocyclohexane-1-carbonitrile; trans-2-aminocyclohexane-1-carbonitrile; cis-2-aminocyclohexane-1-carbonitrile; (4-aminocyclohexyl)methanol; trans-(4-aminocyclohexyl)methanol; trans-4-(Methoxymethyl)cyclohexanamine hydrochloride; cis-4-(Methoxymethyl)cyclohexanamine hydrochloride; (1R,2S,3S)-2,3-dimethylcyclohexan-1-amine hydrochloride; (1R,2S,3R)-2,3-dimethylcyclohexan-1-amine hydrochloride; (1S,2R,3S)-2,3-dimethylcyclohexan-1-amine;
1-ethynylcyclohexylamine; 4,4-difluorocyclohexylamine; (1R,2S)-2-methylcyclopentan-1-amine; cycloheptylamine; cyclohexanemethanamine; aniline; p-chloroaniline; p-fluoroaniline; p-isopropylaniline; o-methylaniline; m-methylaniline; p-methylaniline; benzylamine; and 1-methyl-3-phenylpropylamine.

The compounds and intermediates may be isolated and used as the compound per se or as its salt. As used herein, the terms "salt" or "salts" refers to an acid addition or base addition salt of a compound of the invention or intermediate. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfomate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^{3}H$, $^{13}C$, and $^{14}C$, are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^{2}H$ or D) may afford certain therapeutic advantages resulting from greater metabolic stability, for example increased in vivo half-life, reduced dosage requirements, reduced cyp inhibition (competitive or time dependent) or an improvement in therapeutic index. For example, substitution with deuterium may modulate undesirable side effects of the undeuterated compound, such as competitive cyp inhibition, time dependent cyp inactivation, etc. It is understood that deuterium in this context is regarded as a substituent in compounds of the present invention (including both the monomeric and linker moieties of the dimer). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of the present invention can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

It will be recognized by those skilled in the art that the compounds of the present invention may contain chiral centers and as such may exist in different isomeric forms. As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound.

"Enantiomers" are a pair of stereoisomers that are non-superimposable mirror images of each other. A 1:1 mixture of a pair of enantiomers is a "racemic" mixture. The term is used to designate a racemic mixture where appropriate.

"Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-.

Unless specified otherwise, the compounds of the present invention are meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Compounds of the invention that contain groups capable of acting as donors and/or acceptors for hydrogen bonds may be capable of forming co-crystals with suitable co-crystal formers. These co-crystals may be prepared from compounds of the present invention by known co-crystal forming procedures. Such procedures include grinding, heating, co-subliming, co-melting, or contacting in solution compounds of the present invention with the co-crystal former under crystallization conditions and isolating co-crystals thereby formed. Suitable co-crystal formers include those described in WO 2004/078163. Hence the invention further provides co-crystals comprising a compound of the present invention.

Although not bound to any particular mechanism of action, the compounds of the present invention are believed to target mmpL3 (an essential membrane bound protein and, in particular, to be involved in transportation of essential molecules like trehalose monomycolate (TMM). None of the known first-line or second-line TB agents are known to inhibit the mmpL3 pathway. TMM is an essential component in the mycobacterial cell wall biosynthesis and therefore useful in the treatment of tuberculosis, in particular MDR and XDR resistant tuberculosis. Consequently, a compound of the present invention may be used in the manufacture of a medicament for the treatment of tuberculosis.

The compounds of the present invention are typically used as a pharmaceutical composition (e.g., a compound of the present invention and at least one pharmaceutically acceptable carrier). As used herein, the term "pharmaceutically acceptable carrier" includes generally recognized as safe (GRAS) solvents, dispersion media, surfactants, antioxidants, preservatives (e.g., antibacterial agents, antifungal agents), isotonic agents, salts, preservatives, drug stabilizers, buffering agents (e.g., maleic acid, tartaric acid, lactic acid, citric acid, acetic acid, sodium bicarbonate, sodium phosphate, and the like), and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated. For purposes of this invention, solvates and hydrates are considered pharmaceutical compositions comprising a compound of the present invention and a solvent (i.e., solvate) or water (i.e., hydrate).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to give the patient an elegant and easily handleable product.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), ampoules, plastic bags, metal cylinders, and the like.

The container may also include a tamper-proof assemblage to prevent indiscreet access to the contents of the package. In addition, the container has deposited thereon a label that describes the contents of the container. The label may also include appropriate warnings.

In certain instances, it may be advantageous to administer the compound of the present invention in combination with at least one additional pharmaceutical (or therapeutic) agent (e.g., first-line or second-line antituberculosis drugs, and for patients with HIV or AIDS an HIV/AIDS drug). The compound of the present invention may be administered either simultaneously with, or before or after, one or more other therapeutic agent(s). Alternatively, the compound of the present invention may be administered separately, by the same or different route of administration, or together in the same pharmaceutical composition as the other agent(s).

Suitable additional TB agents include first-line drugs (such as isoniazid, rifampicin, pyrazinamide, ethambutol and combinations thereof); second-line drugs (such as streptomycin, kanamycin, amikacin, capreomycin, ofloxacin, levofloxacin, moxifloxacin, cycloserine, para-aminosalicylic acid, ethioamide, prothionamide, thioacetazone and combinations thereof); and other antituberculosis drugs (such as clofazimine, amoxicilin with clavulanate, imipenem, linezolid, clarithromycin, thioridazine and combinations thereof).

Other potential additional TB agents include compounds such as bicyclic nitroimidazoles (e.g., (S)-6,7-dihydro-2-nitro-6-[[4-(trifluoromethoxy)phenyl]methoxy]-5H-imidazo[2,1-b][1,3]oxazine (PA-824) and TBA-354, available from TB Alliance), bedaquiline (TMC-207), delamanid (OPC67683), oxazolidinone, 2-[(2S)-2-methyl-1,4-dioxa-8-azaspiro[4.5]decan-8-yl]-8-nitro-6-trifluoromethyl-4H-1,3-benzothiazin-4-one (BTZ043), imidazopyridines (e.g., Q201, available from Quro Science Inc.), and combinations thereof.

Suitable therapeutic agents for adjunct therapy include human immunodeficiency virus (HIV) drugs, immunotherapeutic agents, (e.g., anti-interleukin 4 neutralizing antibodies, mycobaterium vaccae, high-dose intravenous immunoglobulin, 16a-bromoepiandosterone (HE2000), RUTI® vaccine, DNA vaccine with HSP65, Ag85, MPT-64, and MPT-83, dzherelo (plant extracts from the Ukraine), cytokines (such as Interleukin 2, Interleukin 7, Interleukin 15, Interleukin 27, Interleukin 12, Interferon γ), immunosuppressive agents (such as corticosteroids, thalidomide, and etanercept)), steroids, anti-inflammatory agents (e.g., prednisone), and other agents well-known to those of skill in art for use in improving the quality of care for patients being treated for the diseases, conditions, or disorders described herein.

Suitable HIV/AIDS drugs include non-nucleoside reverse transcriptase inhibitors (NNRTIs), such as efavirenz (Sustiva), etravirine (Intelence) and nevirapine (Viramune); Nucleoside reverse transcriptase inhibitors (NRTIs), such as Abacavir (Ziagen), and the combination drugs emtricitabine and tenofovir (Truvada), and lamivudine and zidovudine (Combivir); Protease inhibitors (PIs), such as atazanavir (Reyataz), darunavir (Prezista), fosamprenavir (Lexiva) and ritonavir (Norvir); Entry or fusion inhibitors, such enfuvirtide (Fuzeon) and maraviroc (Selzentry); and Integrase inhibitors, such as Raltegravir (Isentress).

The compound of the present invention or pharmaceutical composition thereof for use in humans is typically administered orally at a therapeutic dose.

The typical dose (effect amount) range is generally from about 300 mg to about 1100 mg/day to a 70 kg body weight adult for full treatment duration in an accepatable formulation. The "effective amount" of a compound of the invention is the amount necessary or sufficient to treat or prevent a disease caused by a mycobacterial infections such as those caused by *Mycobacterium tuberculosis, Mycobacterium bovis, Mycobacterium leprae, Mycobacterium africanum, Mycobacterium avium, Mycobacterium microti*, or any *mycobacterium* that causes multi-drug resistant (MDR) TB or extensively resistant (XDR) TB, or any other mycobacterial species known to cause disease in humans. The effective amount can vary depending on the compound employed, the mode of administration, the treatment desired and the disease indicated, as well as other factors such as a patient's age, body weight, general health and sex. Furthermore, several divided dosages, as well as staggered dosages, can be administered daily or sequentially, or the dose can be continuously infused, or can be a bolus injection. Further, the dosages of the compounds of the invention can be proportionally increased or decreased as indicated by the exigencies of the therapeutic or prophylactic situation.

In general, the therapeutically effective dosage of a compound, the pharmaceutical composition, or the combinations thereof, is dependent on the species of the subject, the body weight, age and individual condition, the disorder or disease or the severity thereof being treated. A physician, pharmacist, clinician or veterinarian of ordinary skill can readily determine the effective amount of each of the active ingredients necessary to prevent, treat or inhibit the progress of the disorder or disease.

The *International Standards for Tuberculosis Care* describes a widely accepted level of care that all practitioners, public and private, should follow in dealing with people who have, or are suspected of having, tuberculosis. The Standards are intended to facilitate the effective engagement of all care providers in delivering high-quality care for patients of all ages, including those with sputum smear-positive, sputum smear-negative, and extrapulmonary tuberculosis; tuberculosis caused by drug resistant *Mycobacterium tuberculosis* complex (*M. tuberculosis*) organisms; and tuberculosis combined with human immunodeficiency virus (HIV) infection.

Another aspect of the invention is a product comprising a compound of the present invention and at least one other therapeutic agent (or pharmaceutical agent) as a combined preparation for simultaneous, separate or sequential use in therapy to treat a subject having sputum smear-positive, sputum smear-negative, and extrapulmonary tuberculosis; tuberculosis caused by drug resistant *Mycobacterium tuberculosis* complex (*M. tuberculosis*) organisms; or tuberculosis combined with human immunodeficiency virus (HIV) infection.

In the combination therapies of the invention, the compound of the present invention and the other therapeutic agent may be manufactured and/or formulated by the same or different manufacturers. Moreover, the compound of the present invention and the other therapeutic (or pharmaceutical agent) may be brought together into a combination therapy: (i) prior to release of the combination product to physicians (e.g. in the case of a kit comprising the compound of the invention and the other therapeutic agent or fixed dose composition); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of the present invention for treating tuberculosis, in particular MDR and XDR resistant tuberculosis, wherein the medicament is prepared for administration with another therapeutic agent. The invention also provides for the use of another therapeutic agent, wherein the medicament is administered as a combination of a compound of the present invention with the other therapeutic agent.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

Unless specified otherwise, starting materials are generally available from commercial sources such as TCI Fine Chemicals (Japan), Shanghai Chemhere Co., Ltd. (Shanghai, China), Aurora Fine Chemicals LLC (San Diego, Calif.), FCH Group (Ukraine), Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), AstraZeneca Pharmaceuticals (London, England), Chembridge Corporation (USA), Matrix Scientific (USA), Conier Chem & Pharm Co., Ltd (China), Enamine Ltd (Ukraine), Combi-Blocks, Inc. (San Diego, USA), Oakwood Products, Inc. (USA), Apollo Scientific Ltd. (UK), Allichem LLC. (USA) and Ukrorgsyntez Ltd (Latvia).

The following abbreviations used herein below have the corresponding meanings:
h hour(s)
DCM dichloromethane
NMR nuclear magnetic resonance
TLC thin layer chromatography
MS mass spectrometry
LC-MS liquid chromatography-mass spectrometry
HPLC high performance liquid chromatography
DMSO dimethylsulfoxide
TEA triethylamine
$Et_3N$ triethylamine
DMF dimethylformamide
THF tetrahydrofuran
TBAF tetra-n-butylammonium fluoride
DIPEA N,N-diisopropylethylamine
HATU 2-(7-Aza-1H-Benzotriazole-1-yl)-1,1,3,3-tetramethyluronium hexafluorophosphate
$NH_4Cl$ ammonium chloride
$Na_2SO_4$ sodium sulphate
NaOH sodium hydroxide
LiOH lithium hydroxide
$H_2SO_4$ sulphuric acid
$NaHCO_3$ sodium bicarbonate
$Na_2CO_3$ sodium carbonate
HCl hydrochloric acid
$NH_2OH.HCl$ hydroxylamine hydrochloride
$NaCNBH_3$ sodium cyanoborohydrate
TFA trifluoroacetic acid
DMAP 4-dimethylaminopyrdine
$Boc_2O$ di-tert-butyl dicarbonate
JohnPhos 2-(di-tert-butylphosphino)biphenyl General Procedures The following three methods (A, B or C) were used to synthesize the substituted indole-2-carboxamides using substituted indole-2-carboxylic acids and amines

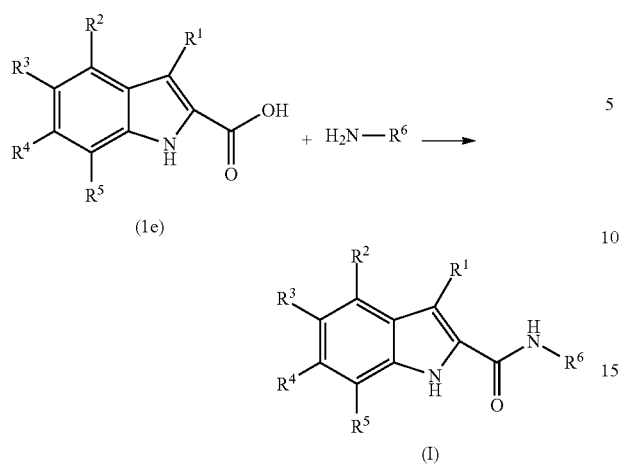

(Ie)

(I)

To indole-2-carboxylic acid (1e) (500 μL, 0.2 M in anhydrous DMF) was added HATU (250 μL, 0.4 M in anhydrous DMF) and Et$_3$N (50 μL, 2.0 M in anhydrous DMF) and stirred for 5 minutes at room temperature. The desired amine (R$^6$—NH$_2$) was dissolved in 520 μL anhydrous DMF and added to the reaction mixture. The reaction mixture was stirred for two hours at 45° C. and the solvent was evaporated in vacuo and the residue was purified via preparative HPLC to obtain the desired product indole-2-carboxamide (I).

Purification Method for Library Compounds:
  Column: BISCHOFF C18 20*50 mm 10 μm, A: Water (0.1% TFA) B: Methanol, Shimadzu HPLC Pump.
QC Method for Library Compounds:
  Column: ZORBAX SB-C8 30*4.6 mm, 3.5 μm
  Detector: UV and ELSD
  Mobile phase: A: Water (0.03% TFA), B: CH$_3$CN (0.05% TFA),
  Flow rate: 2.000 mL/minute
  Gas pressure: 3.3 bar
  Drift tube temp: 35° C.
  Wavelength: 214 nm Method B To a solution of substituted indole-2-carboxylic acid (1e: 1 mmol) in dry DMF (4 mL) were added HATU (1.5 eq.) and the desired amine (R$^6$—NH$_2$: 1.2 eq.) followed by DIPEA (5.0 eq.) at 0° C. The resulting mixture was stirred at room temperature for 12 h to 24 h. To the reaction mixture water (10 mL) was added and stirred for 10 minutes. The resultant solid was collected by filtration, washed with water, hexane and dried. In some instances reaction mixture was extracted with ethyl acetate. The organic layer was washed with water, brine, dried over anhydrous Na$_2$SO$_4$ and concentrated under reduced pressure. The crude compounds were purified by column chromatography over silica gel (100-200 mesh) or CombiFlash® purification system (Teledyne Isco) using appropriate mixtures of ethyl acetate and hexanes/petroleum ether or preparative HPLC to obtain the desired product indole-2-carboxamide (I).

Method C

To a solution of indole-2-carboxylic acid (1e: 1 mmol) in DMF (4 mL) was added DIPEA (2 eq.) followed by HATU (1.2 eq.). The mixture was stirred for 15 minutes before the desired amine (R$^6$—NH$_2$) was added. The mixture was left to stir at room temperature for 5-16 hrs before saturated NH$_4$Cl solution was added. The mixture was extracted with ethyl acetate and the combined organic extracts were washed with water and brine, dried over anhydrous Na$_2$SO$_4$, filtered and concentrated in vacuo. The crude material was purified on CombiFlash® purification system (Teledyne Isco) using appropriate mixtures of ethyl acetate and cyclohexanes to obtain the desired product indole-2-carboxamide (I).

Preparation of Key Intermediates

Preparation of Intermediate 4,6-dichloro-H-indole-2-carboxylic acid from 3,5-dichloro aniline (I-1d)

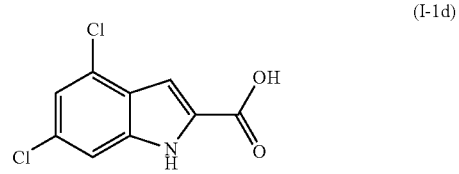 [SMILES: O=C(O)c1cc2c(Cl)cc(Cl)cc2[nH]1]

(I-1d)

Step 1: Preparation of Intermediate 3,5-chlorophenyl)hydrazine (I-1a)

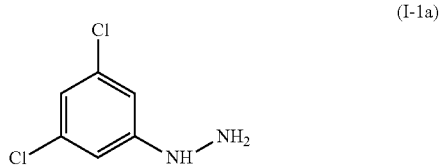

(I-1a)

To a cold suspension of 3,5-dichloroaniline (15.0 g, 92.58 mmol, ×4 batches) in conc. HCl (45 mL, for each batch) was added a solution of NaNO$_2$ (7 g, 101.44 mmol, for each batch) in water (65 mL, for each batch) at –10° C. and stirred for 30 minutes. Then a solution of SnCl$_2$ (52.49 g, 277.7 mmol, for each batch) in conc. HCl (45 mL, for each batch) was added slowly. After addition was complete, a white precipitate was formed which was stored at 4° C. for 7 h. The precipitated solid was collected by filtration, washed with hexane and suspended in 10% aq NaOH solution (pH=13) and extracted with Ethyl acetate (4×200 mL). The organic layer was washed with water (250 mL), brine, dried over anhydrous Na$_2$SO$_4$ and concentrated under reduced pressure. The solids thus obtained from 4 batches were combined and was washed with n-hexane to afford 45 g (68.6%) of 3,5-chlorophenyl)hydrazine (I-1a) as an off-white solid.

$^1$H NMR (400 MHz, DMSO-d$_6$): δ 6.75 (s, 1H), 6.72 (s, 2H), 5.30 (br s, 1H, —NH), 3.58 (br s, 2H, —NH$_2$). ESI MS: m/z 179.0 (M+2H).

Step 2: Preparation of Intermediate Ethyl 2-(2-(3,5-dichlorophenyl)hydrazono)-propanoate (I-1b)

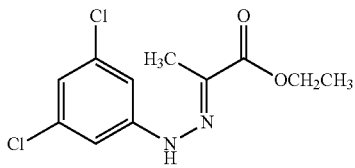

(I-1b)

To a mixture of (3,5-chlorophenyl)hydrazine (I-1a: 22 g, 124.27 mmol, ×2 batches) and 2-oxo-propionic acid ethyl ester (14.5 mL, 124.27 mmol, for each batch) in ethanol (120 mL, for each batch) was added con. $H_2SO_4$ (2 mL, for each batch) and the reaction mixture stirred at room temperature for 3 h. Ethanol was distilled-off and the residue was dissolved in ethyl acetate and washed with 10% aqueous $NaHCO_3$ solution. The combined organic layer was washed with water, brine, dried over anhydrous $Na_2SO_4$ and concentrated under reduced pressure to afford 52 g (76%) of ethyl 2-(2-(3,5-dichlorophenyl)hydrazono) propanoate (I-1b) as an off-white solid.

$^1$H NMR (400 MHz, DMSO-$d_6$): δ 10.12 (s, 1H), 7.22 (s, 2H), 7.05 (s, 1H), 4.20 (q, J=6.8 Hz, 2H), 2.05 (s, 3H), 1.26 (t, J=7.2 Hz, 3H). ESI MS: m/z 272.9 (M−H) & 274.9 [(M+2)-H].

Step 3: Preparation of Intermediate Ethyl 4,6-dichloro-1H-indole-2-carboxylate (I-1c)

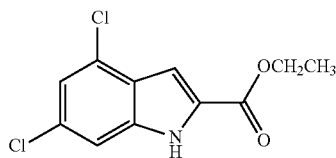

(I-1c)

A mixture of ethyl 2-(2-(3,5-dichlorophenyl)hydrazono) propionate (I-1b: 26 g, 94.50 mmol, ×2 batches) and polyphosphoric acid (260 g, for each batch) was stirred at 110° C. for 3 h. The reaction mixture was poured into crushed ice and stirred well and the resultant precipitate was collected by filtration. The obtained solid was basified using saturated aqueous $NaHCO_3$ (pH=10) and extracted into ethyl acetate (3×150 mL). The combined organic layer washed with brine, dried on anhydrous $Na_2SO_4$ and concentrated. Crude compound was purified (over 100-200 silica) using 30% ethyl acetate in hexanes as eluent to afford 36 g (73.8%) of ethyl 4,6-dichloro-1H-indole-2-carboxylate (I-1c) as an off-white solid.

$^1$H NMR (400 MHz, DMSO-$d_6$): δ 12.46 (s, 1H), 7.46 (s, 1H), 7.30 (s, 1H), 7.12 (s, 1H), 4.36 (q, J=7.2 Hz, 2H), 1.35 (t, J=7.2 Hz, 3H). ESI MS: m/z 255.8 (M−H).

Final Step: Preparation of Intermediate 4,6-Dichloro-1H-indole-2-carboxylic acid (I-1d)

To a solution of ethyl 4,6-dichloro-1H-indole-2-carboxylate (I-1c: 50 g, 193.72 mmol) in a solvent mixture consisting of THF & water (1:1) (900 mL) was added LiOH.$H_2O$ (24.41 g, 581.7 mmol) and the reaction mixture stirred at room temperature for 18h. The solvent (THF) was distilled-off, the residue was diluted with water (400 mL) and acidified with 2N aqueous HCl to pH 6.0. The residue was extracted in to ethyl acetate (4×150 mL), combined organic layer washed with brine (350 ml), dried on anhydrous $Na_2SO_4$ and concentrated under reduced pressure to obtain 39 g (87.5%) of 4,6-dichloro-1H-indole-2-carboxylic acid (I-1d) as light brown solid.

$^1$H NMR (400 MHz, DMSO-$d_6$): δ 12.25 (s, 1H), 7.43 (s, 1H), 7.25 (s, 1H), 7.05 (s, 1H). ESI MS: m/z 227.7 (M−H).

Preparation of Intermediate 4,6-Dicyano-1H-indole-2-carboxylic acid (I-2b)

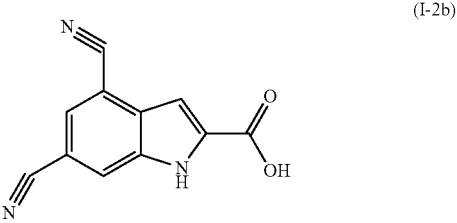 [SMILES: N#Cc1cc(C#N)c2cc(C(=O)O)[nH]c2c1]

(I-2b)

Step 1: Preparation of Intermediate Ethyl 4,6-dicyano-1H-indole-2-carboxylate (I-2a)

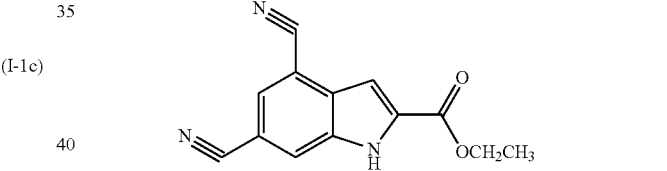

(I-2a)

To an argon purged solution of ethyl 4,6-dichloro-1H-indole-2-carboxylate (I-1c: 1 g, 3.89 mmol) in DMF (8 mL) were added dicyanozinc (1.37 g, 11.67 mmol), $Pd_2(dba)_3$ (356 mg, 0.389 mmol) followed by Xphos (166 mg. 0.389 mmol), the mixture was then stirred in microwave at 160° C. for 14 h. The resultant reaction mixture was allowed to cool to room temperature, diluted with water (10 mL) and ammonia solution (2 mL; Specific Gravity 0.91). The aqueous layer was extracted with ethyl acetate (3×50 mL). The combined organic layer was washed with water, brine, dried over anhydrous $Na_2SO_4$ solution and concentrated. The crude compound was purified by column chromatography over silica gel (100-200 mesh) using a solvent gradient of 6% ethyl acetate in chloroform as eluent to afford 300 mg (32%) of ethyl 4,6-dicyano-1H-indole-2-carboxylate (I-2a) as a brown solid.

ESI MS: m/z 237.9 (M−H).

Final Step: Preparation of 4,6-Dicyano-1H-indole-2-carboxylic acid (I-2b)

To a stirred solution of ethyl 4,6-dicyano-1H-indole-2-carboxylate (I-2a: 500 mg, 2.09 mmol) in ethanol (10 mL) was added LiOH.$H_2O$ (176 mg, 4.18 mmol) and heated to reflux for 6 h. Ethanol was evaporated under reduced pressure and the residue was washed with diethyl ether. The solid formed was dissolved in water (20 mL), acidified with saturated citric acid solution and filtered. The solid was further washed with water and dried under vacuum to afford 250 mg (57%) of 4,6-dicyano-1H-indole-2-carboxylic acid (I-2b) as a light brown solid.

ESI MS: m/z 209.9 (M–H).

Preparation of Intermediate
4-cyano-1H-indole-2-carboxylic acid (I-3b)

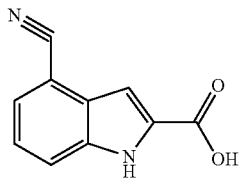

(I-3b)

Step 1: Preparation of Intermediate Ethyl
4-cyano-1H-indole-2-carboxylate (I-3a)

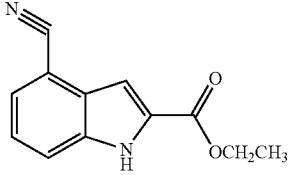

(I-3a)

To a stirred solution of ethyl 4-bromo-1H-indole-2-carboxylate (500 mg, 1.86 mmol) in DMF (10 mL) was added Cu(I)CN (501 mg, 5.59 mmol) and heated to 150° C. for 24 h. The reaction mixture was cooled to room temperature, the water (25 mL) was added and the reaction mixture extracted with ethyl acetate (4×50 mL). The organic layer was washed with water (25 mL), brine (25 mL), dried over anhydrous $Na_2SO_4$ and evaporated under reduced pressure to get the crude product. The crude product was purified by column chromatography over silica gel (100-200 mesh) using a solvent gradient of 10% ethyl acetate in petroleum ether to afford 330 mg (82%) of ethyl 4-cyano-1H-indole-2-carboxylate (I-3a) as an off-white solid.

$^1$H NMR (400 MHz, $CDCl_3$): δ 9.14 (s, 1H), 7.67 (d, J=8.41 Hz, 1H), 7.55 (d, J=6.56 Hz, 1H), 7.41 (s, 1H), 7.38 (t, J=8.41 Hz, 1H), 4.45 (q, J=7.32 Hz, 2H), 1.44 (t, J=7.32 Hz, 3H).

Final Step: 4-Preparation of Intermediate
Cyano-1H-indole-2-carboxylic acid (I-3b)

To a solution of ethyl 4-cyano-1H-indole-2-carboxylate (I-3a: 330 mg, 1.542 mmol) in ethanol (10 mL) was added $LiOH.H_2O$ (129 mg, 3.08 mmol) and the mixture was refluxed for 16 h. The solvent was evaporated under reduced pressure and the residue diluted with water (10 mL). The aqueous layer was acidified with 10% aq. HCl solution to pH 6.0 and the precipitated solid was filtered. The residue was washed with water and dried under vacuum to afford 250 mg (87%) of 4-cyano-1H-indole-2-carboxylic acid (I-3b) as an off-white solid.

$^1$H NMR (400 MHz, DMSO-$d_6$): δ 13.44 (br s, 1H), 12.46 (s, 1H), 7.79 (d, J=8.88 Hz, 1H), 7.65 (d, J=7.61 Hz, 1H), 7.44-7.38 (m, 1H), 7.12 (d, J=1.27 Hz, 1H).

ESI MS: m/z 184.7 (M–H).

Preparation of Intermediate
5H-[1,3]dioxolo[4,5-f]indole-6-carboxylic acid
(I-4c)

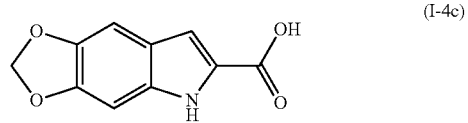 [SMILES: O=C(O)c1cc2cc3c(cc2[nH]1)OCO3]

(I-4c)

The intermediate I-4c was synthesized using the procedure described in Dong, Xiaochun; et al., *Med. Chem. Lett.*, 16, 5913-5916 (2006).

Step 1: Preparation of Intermediate (Z)-Ethyl
2-azido-3-(benzo[d][1,3]dioxol-5-yl)acrylate (I-4a)

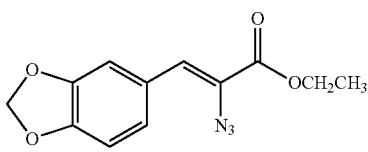

(I-4a)

To a stirred solution of ethyl bromo acetate (20 g, 119.76 mmol) in ethanol (52 mL) was added $NaN_3$ solution (7.78 g, 119.76 mmol) in water (24 mL) and heated to reflux for 4 h. Ethanol was evaporated under reduced pressure and the aqueous layer extracted with ether. The organic layer was washed with water, brine, concentrated, and dried to afford 3.4 g of ethyl azido acetate.

A solution of benzo[d][1,3]dioxole-5-carbaldehyde (1 g, 6.66 mmol) and ethyl azido acetate (3.4 g, 26.64 mmol) in ethanol (5 mL) was added drop wise to sodium ethoxide (1.8 g, 26.64 mmol) in ethanol (5 mL) at 0° C. and stirred for 4 h. The reaction mixture was quenched with aq. $NH_4Cl$ solution and extracted with ethyl acetate. The combined organic layer was washed with water, brine, dried over anhydrous $Na_2SO_4$ solution and concentrated under reduced pressure. The crude compound was purified by column chromatography over silica gel (100-200 mesh) using a solvent gradient of 4-6% ethyl acetate in petroleum ether as eluent to afford 0.6 g (34%) of (Z)-ethyl 2-azido-3-(benzo [d][1,3]dioxol-5-yl)acrylate (I-4a) as an off-white solid.

$^1$H NMR (400 MHz, $CDCl_3$): δ 7.58 (d, J=1.46 Hz, 1H), 7.19-7.17 (m, 1H), 6.84 (s, 1H), 6.82 (d, J=8.05 Hz, 1H), 6.01 (s, 2H), 4.39-4.23 (m, 2H), 1.42-1.29 (m, 3H).

Step 2: Preparation of Intermediate Ethyl
5H-[1,3]dioxolo[4,5-f]indole-6-carboxylate (I-4b)

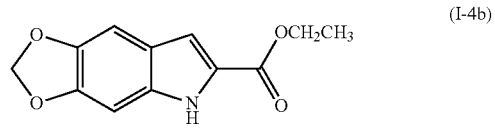 [SMILES: CCOC(=O)c1cc2cc3c(cc2[nH]1)OCO3]

(I-4b)

A stirred solution of (Z)-ethyl 2-azido-3-(benzo[d][1,3]dioxol-5-yl)acrylate (I-4a: 0.6 g, 1.532 mmol) in xylene (20 mL) was maintained at 150° C. for 3 h. Xylene was distilled out completely and the crude compound was purified by column chromatography over silica gel (100-200 mesh) using a solvent gradient of 8-10% ethyl acetate in petroleum ether as eluent to afford 0.4 g (75%) of ethyl 5H-[1,3]dioxolo[4,5-f]indole-6-carboxylate (I-4b) as a pale yellow solid.

$^1$H NMR (400 MHz, CDCl$_3$): δ 8.81 (s, 1H), 7.10 (d, J=1.9 Hz, 1H), 6.99 (s, 1H), 6.83 (s, 1H), 5.97 (s, 2H), 4.37 (q, J=6.98 Hz, 2H), 1.39 (t, J=6.98 Hz, 3H).

Final Step: Preparation of Intermediate 5H-[1,3]dioxolo[4,5-f]indole-6-carboxylic acid (I-4c)

To a solution of ethyl 5H-[1,3]dioxolo[4,5-f]indole-6-carboxylate (I-4b: 0.4 g, 1.716 mmol) in ethanol (8 mL) was added LiOH.H$_2$O (0.144 g, 3.433 mmol) and refluxed for 16 h. The solvent was evaporated under reduced pressure and the residue was dissolved in water (10 mL). The aqueous layer was acidified with 10% aq. HCl solution to pH 6.0, precipitated solid was filtered, residue was washed with water and dried under vacuum to afford 0.3 g (86%) of 5H-[1,3]dioxolo[4,5-f]indole-6-carboxylic acid (I-4c) as an off-white solid.

$^1$H NMR (400 MHz, DMSO-d$_6$): δ 12.65 (s, 1H), 11.58 (s, 1H), 7.05 (s, 1H), 6.94 (d, J=2.05 Hz, 1H), 6.85 (s, 1H), 5.98 (s, 2H). ESI MS: 203.9 (M–H).

Preparation of Intermediate 6-(Benzyloxy)-4-methyl-1H-indole-2-carboxylic acid (I-5a)

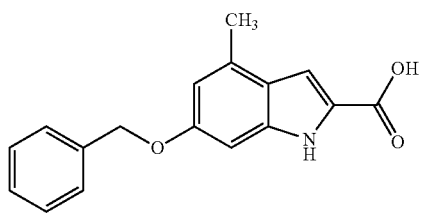

(I-5a)

Intermediate I-5a was prepared using procedures analogous to those described above for the synthesis of 5H-[1,3]dioxolo[4,5-f]indole-6-carboxylic acid (I-4c) using 4-(benzyloxy)-2-methylbenzaldehyde (I-4c) as the starting material instead of benzo[d][1,3]dioxole-5-carbaldehyde. ESI MS: m/z 282.24 (M+H).

Preparation of Intermediate 4,4-dimethylcyclohexyl amine (I-6b)

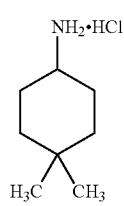

(I-6b)

Step 1: Preparation of Intermediate 4,4-dimethylcyclohexanone oxime (I-6a)

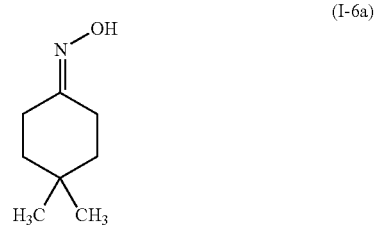

(I-6a)

To 4,4-Dimethylcyclohexanone (50 g, 396.19 mmol), NH$_2$OH.HCl (35.84 g, 515.75 mmol) in H$_2$O (190 mL) and ethanol (250 mL) was added a solution of Na$_2$CO$_3$ (54.16 g, 510.99 mmol) in water (170 mL) dropwise over a period of 20 minutes. After complete addition, reaction mixture was heated to reflux for 3h. The ethanol was evaporated, and the residue extracted into ethyl acetate (4×120 mL). The combined organic layer was washed with water (150 mL), brine (150 mL) and dried over sodium sulfate and concentrated to afford 45 g (80.4%) 4,4-dimethyl cyclohexanone oxime (I-6a) as white solid.

$^1$H NMR (400 MHz, DMSO-d$_6$): δ 10.1 (s, 1H), 2.38 (m, 2H), 2.13 (m, 2H), 1.38-1.28 (m, 4H), 0.95 (s, 6H).

Final Step: 4,4-dimethylcyclohexanamine hydrochloride (I-6b)

4,4-dimethylcyclohexanone oxime (I-6a: 80 g, 566.5 mmol) in ethanol (650 ml) was taken in autoclave and Raney Ni (30 g) was added. The reaction mixture was kept under H$_2$ atmosphere at 80 psi for 16h. The hydrogen atmosphere was removed and the reaction mixture was filtered through a celite pad. The filtrate was stirred with 1M HCl in ether (850 mL) and concentrated to give an off-white residue. It was again triturated with ether (1 L) to obtain 82 g (88.4%) of 4,4-dimethylcyclohexanamine hydrochloride (I-6b) as white crystalline solid.

$^1$H NMR (400 MHz, DMSO-d$_6$): δ 8.01 (br s, 2H), 2.88 (m, 1H), 1.80-1.65 (m, 2H), 1.60-1.4 (m, 2H), 1.40-1.30 (m, 2H), 1.25-1.15 (m, 2H), 0.9 (s, 6H).

Preparation of Intermediate 2-Aminocyclohexanecarbonitrile (I-7b)

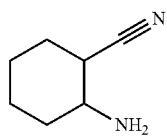

(I-7b)

Step 1: Preparation of
2-Aminocyclohex-1-enecarbonitrile (I-7a)

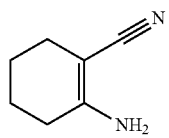
(I-7a)

To cold toluene (20 mL) was added 60% NaH (720 mg, 18.0 mmol) slowly and followed by a solution of 1,5-dicyanopentane (2.1 mL, 16.37 mmol) in toluene (5 mL) slowly at 0° C. The resulting mixture was refluxed for 4 h and cooled to room temperature. The reaction mixture was quenched with ethanol (2 mL), water (20 mL) and acetic acid (2 mL). The organic layer was separated and aqueous layer was extracted with ethyl acetate (3×20 mL). The combined organic layer was washed with brine, dried over anhydrous $Na_2SO_4$ and concentrated under reduced pressure. Water was added to the crude residue, then filtered and washed with hexane to afford 850 mg (42%) of 2-amino-cyclohex-1-enecarbonitrile (I-7a) as a pale brown solid.

$^1$H NMR (400 MHz, CDCl$_3$): δ4.21 (s, 2H), 2.2-2.12 (m, 4H), 1.75-1.55 (m, 4H).

Final Step: Preparation of
2-Aminocyclohexanecarbonitrile (I-7b)

To a cold solution of 2-aminocyclohex-1-enecarbonitrile (I-7a: 50 mg, 0.41 mmol) in methanol (3 mL) was added NaCNBH$_3$ (103 mg, 1.64 mmol) and acetic acid (5 drops) at 0° C. The resulting mixture was stirred at room temperature for 16h. The reaction mixture was diluted with ethyl acetate and the organic layer was washed with saturated NaHCO$_3$, brine, dried over anhydrous Na$_2$SO$_4$ and concentrated to afford 40 mg (78%) of diastereomeric mixture of 2-amino-cyclohexanecarbonitrile (I-7b) as a gum.

ESI MS: m/z 125.3 (M+H)

Preparation of Intermediate
(1R,2S)-2-methylcyclohexanamine (I-8c)

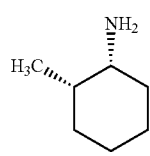
(I-8c)

Intermediate I-8c was prepared using procedures described in PCT Publication No. WO2011/14817 A1.

Step 1: Preparation of Intermediate (1R,E)-N-(2-Methylcyclohexylidene)-1-phenylethanamine (I-8a)

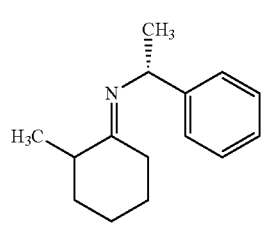
(I-8a)

A stirred solution of 2-methylcyclohexanone (5 g, 44.64 mmol) and (R)-1-phenylethanamine (5.4 g, 44.64 mmol) in toluene (50 mL) was maintained at 140-145° C. for 24 h. The solvent was removed under reduced pressure to afford 8 g (84%) of a diastereomeric mixture of (1R,E)-N-(2-methylcyclohexylidene)-1-phenylethanamine (I-8a) as a pale yellow oil.

Step 2: Preparation of Intermediate 2-Methyl-N—((R)-1-phenylethyl)cyclohexanamine (I-8b)

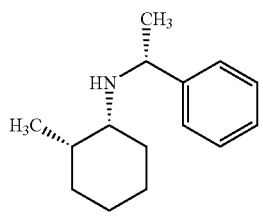
(I-8b)

A suspension of (1R,E)-N-(2-methylcyclohexylidene)-1-phenylethanamine (I-8a: 25 g, 116.27 mmol) and Raney-Ni (3.75 g) in ethanol (250 mL) was maintained under hydrogen atmosphere in a Parr hydrogenator using 5 bar pressure for 2 days. The reaction mixture was filtered and filtrate evaporated under reduced pressure. The crude compound was treated with ethereal HCl, and the precipitated salt was filtered, washed with cold ether and dried to afford 20 g (80%) of 2-methyl-N—((R)-1-phenylethyl)-cyclohexanamine (I-8b) as a white solid.

ESI MS: m/z 218.19 (M+H).

Final Step: Preparation of Intermediate
(1R,2S)-2-methylcyclohexanamine (I-8c)

A solution of 2-methyl-N—((R)-1-phenylethyl)cyclohexanamine (I-8b: 30 g, 178.57 mmol) in glacial acetic acid (160 mL) was treated with 10% Pd—C (0.820 mg). The mixture maintained under a hydrogen atmosphere (45 psi) in a Parr hydrogenator at 50° C. for 19 h. The reaction mixture was filtered through a celite pad and the filtrate was adjusted to pH 12 with 6N NaOH (500 mL) solution. The compound was extracted with chloroform (3×500 mL), dried over anhydrous Na$_2$SO$_4$ and evaporated to afford 7.5 g (35%) of (1R,2S)-2-methylcyclohexanamine (I-8c) as a yellow solid.

$^1$H NMR (400 MHz, CDCl$_3$): δ 8.32 (br s, 2H), 3.4-3.35 (m, 1H), 2.02-1.25 (m, 9H), 1.1 (d, J=7.03 Hz, 3H).

The following chiral amines were prepared using procedures described in Speckenbach, B., et al., *Synthesis*, 1325-1330 (1997).

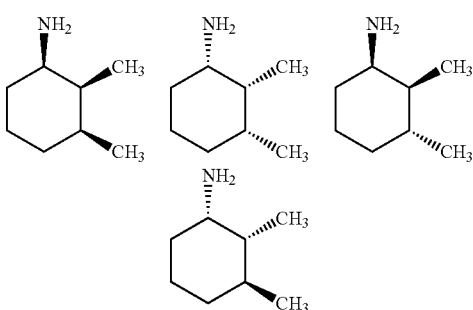

Example 1

Preparation of 4,6-dichloro-N-(4,4-dimethylcyclohexyl)-1H-indole-2-carboxamide (1A)

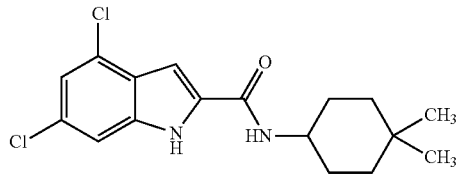

(1A)

A mixture of 4,6-dichloro-1H-indole-2-carboxylic acid (I-1d: 205 g, 891.1 mmol in 9 batches) and 4,4-dimethylcyclohexylamine.HCl (I-6b: 160.4 g, 980.2 mmol) in dry DMF (2290 mL) was cooled to 0° C. and added HATU (406.3 g, 1070 mmol) followed by DIPEA (775.5 mL, 4450 mmol) drop-wise and the mixture was stirred under inert atmosphere at room temperature for 17 h. Ice-cold water (7000 mL) was added to the reaction mixture and stirred vigorously and the precipitated solid was collected by filtration and dried thoroughly. The combined crude solids from all batches were purified by column chromatography over silica gel (100-200 mesh) using a solvent gradient of 30%-40% ethyl acetate in hexanes as eluent to afford 213 g of light brown solid. It was triturated with ether/hexanes (3:7) in five cycles to give off-white solid. The solid was treated with charcoal in ethyl acetate/methanol (4:1) at 70° C. for 3h and filtered to afford 207 g (68.5%) of 4,6-dichloro-N-(4,4-dimethylcyclohexyl)-1H-indole-2-carboxamide (1A) as a white solid.

$^1$H NMR (400 MHz, DMSO-$d_6$): δ 12.06 (s, 1H), 8.44 (d, J=8.0 Hz, 1H), 7.41 (s, 1H), 7.30 (s, 1H), 7.22 (s, 1H), 3.80-3.65 (m, 1H), 1.70-1.60 (m, 2H), 1.60-1.45 (m, 2H), 1.45-1.35 (m, 2H), 1.35-1.20 (m, 2H), 0.95 (s, 3H), 0.93 (s, 3H). $^{13}$C NMR (100 MHz, DMSO-$d_6$): δ 159.3, 136.7, 133.7, 127.5, 126.2, 124.8, 119.3, 111.1, 100.6, 48.1, 37.6 (2C), 32.1, 29.3 (2C), 28.1 (2C). ESI MS: m/z 339.01 [(M+H]& 341.03 [(M+2)+H]. HPLC purity: 99.7%.

Example 2

Preparation of N-(4,4-Dimethylcyclohexyl)-4,6-difluoro-1H-indole-2-carboxamide (2A)

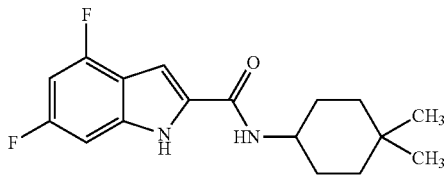

(2A)

A mixture of 4,6-difluoro-1H-indole-2-carboxylic acid (5 g, 25.36 mmol×4 batches) and 4,4-dimethylcyclohexylamine.HCl (I-6b: 4.6 g, 28.10 mmol, for each batch) in dry DMF (75 mL) was cooled to 0° C. and HATU (11.62 g, 30.57 mmol, for each batch) was added followed by DIPEA (22 mL, 127.9 mmol, for each batch) drop-wise and the mixture was stirred under inert atmosphere at room temperature for 17h. Ice-cold water (50 mL) was added to the reaction mixture with vigorous stirring. The precipitated solid was collected by filtration and dried thoroughly. The crude compound obtained from combining all the batches was purified by column chromatography over silica gel (100-200 mesh) using a solvent gradient of 30%-40% ethyl acetate in hexanes as eluent to afford 23 g of off-white solid. It was triturated with ether/hexanes (3:7) in five cycles to afford 20.6 g (66.2%) of 4,6-difluoro-N-(4,4-dimethylcyclohexyl)-1H-indole-2-carboxamide (2A) as an white solid.

$^1$H NMR (400 MHz, DMSO-$d_6$): δ 11.97 (s, 1H), 8.30 (d, J=8.0 Hz, 1H), 7.26 (s, 1H), 7.12 (d, J=8.8 Hz, 1H), 6.88 (t, J=10.4 Hz, 1H), 3.80-3.65 (m, 1H), 1.70-1.60 (m, 2H), 1.60-1.45 (m, 2H), 1.45-1.35 (m, 2H), 1.35-1.20 (m, 2H), 0.95 (s, 3H), 0.92 (s, 3H).

ESI MS: m/z 307.11 (M+H) & 308.12 [(M+1)+H]. HPLC purity: 98.6%.

Example 3

The compounds in Table 1 below were prepared using the general procedures described in Method A above with the appropriate starting materials.

TABLE 1

| Example No. | Structure/Name | Analytical Data |
|---|---|---|
| 3A | ![structure] CH₃ and H₃C groups on indole, N-(4-Isopropylphenyl)-4,6-dimethyl-1H-indole-2-carboxamide | LC MS: m/z 307.67 (M + H). |

TABLE 1-continued

| Example No. | Structure/Name | Analytical Data |
|---|---|---|
| 3B | 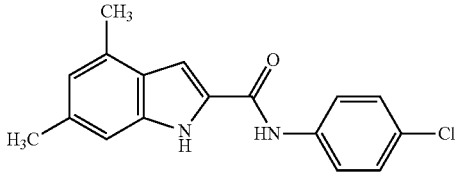<br>N-(4-chlorophenyl)-4,6-dimethyl-1H-indole-2-carboxamide | LC MS: m/z 299.53 (M + H). |
| 3C | 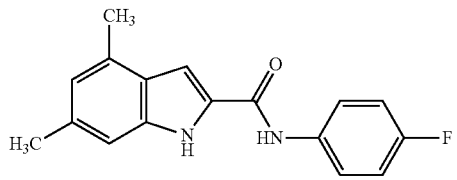<br>N-(4-fluorophenyl)-4,6-dimethyl-1H-indole-2-carboxamide | LC MS: m/z 283.58 (M + H). |
| 3D | 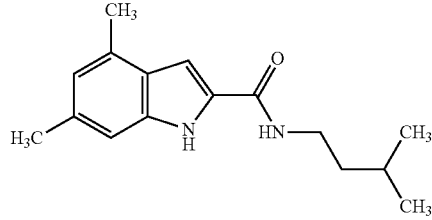<br>N-isopentyl-4,6-dimethyl-1H-indole-2-carboxamide | LC MS: m/z 259.63 (M + H). |
| 3E | 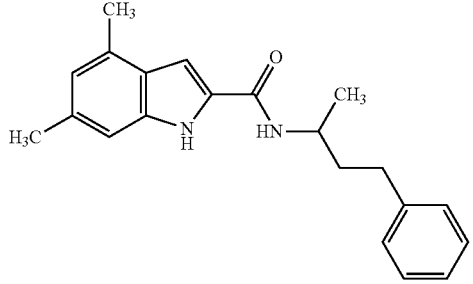<br>4,6-dimethyl-N-(4-phenylbutan-2-yl)-1H-indole-2-carboxamide | LC MS: m/z 321.65 (M + H). |
| 3F | 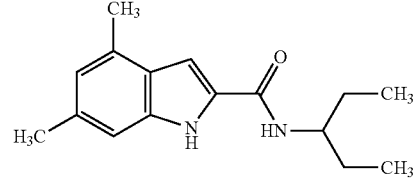<br>4,6-dimethyl-N-(pentan-3-yl)-1H-indole-2-carboxamide | LC MS: m/z 259.64 (M + H). |

TABLE 1-continued

| Example No. | Structure/Name | Analytical Data |
|---|---|---|
| 3G | 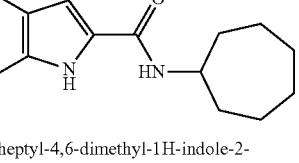\nN-cycloheptyl-4,6-dimethyl-1H-indole-2-carboxamide | LC MS: m/z 285.64 (M + H) |
| 3H | 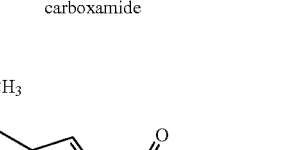\n4,6-dimethyl-N-(2-methylcyclohexyl)-1H-indole-2-carboxamide | LC MS: m/z 285.64 (M + H). (diasteromeric mixture) |
| 3I | 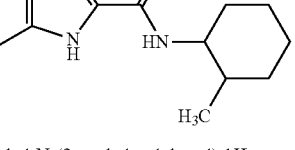\n4,6-dimethyl-N-(2-methylbutyl)-1H-indole-2-carboxamide | LC MS: m/z 259.64 (M + H). |
| 3J | 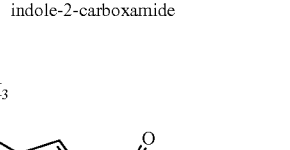\nN-isobutyl-4,6-dimethyl-1H-indole-2-carboxamide | LC MS: m/z 245.61 (M + H). |
| 3K | 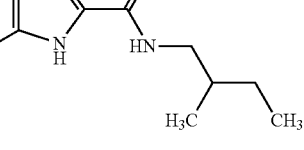\n4,6-dimethyl-N-(p-tolyl)-1H-indole-2-carboxamide | LC MS: m/z 279.62 (M + H). |

TABLE 1-continued

| Example No. | Structure/Name | Analytical Data |
|---|---|---|
| 3L | 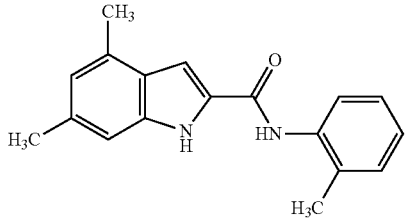<br>4,6-dimethyl-N-(o-tolyl)-1H-indole-2-carboxamide | LC MS: m/z 279.60 (M + H). |
| 3M | 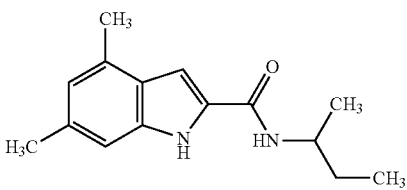<br>N-(sec-butyl)-4,6-dimethyl-1H-indole-2-carboxamide | LC MS: m/z 245.64 (M + H). |
| 3N | 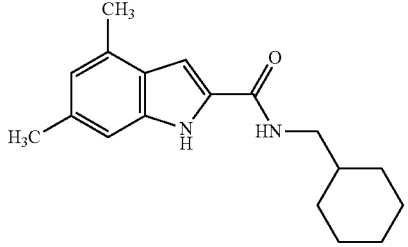<br>N-(cyclohexylmethyl)-4,6-dimethyl-1H-indole-2-carboxamide | LC MS: m/z 254.68 (M + H). |

Example 4

The compounds in Table 2 below were prepared using the general procedures described in Method B above with the appropriate starting materials.

TABLE 2

| Example No. | Structure/Name | Analytical Data |
|---|---|---|
| 4A | 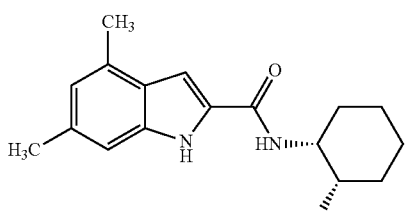<br>4,6-dimethyl-N-((1R,2S)-2-methylcyclohexyl)-1H-indole-2-carboxamide | $^1$H NMR (400 MHz, CDCl$_3$): δ 11.34 (s, 1H), 7.77 (d, J = 8.35 Hz, 1H), 7.28 (s, 1H), 7.01 (s, 1H), 6.66 (s, 1H), 4.1 (br s, 1H), 2.45 (s, 3H), 2.34 (s, 3H), 1.95 (br s, 1H), 1.69-1.50 (m, 8H), 0.87 (d, J = 7.0 Hz, 3H). ESI MS: m/z 285.28 (M + H). HPLC purity: 97.95%. |

TABLE 2-continued

| Example No. | Structure/Name | Analytical Data |
|---|---|---|
| 4B | 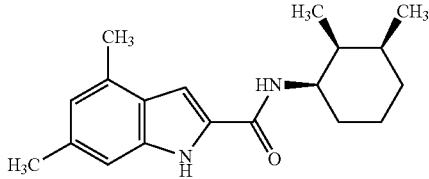<br>N-((1R,2S,3S)-2,3-dimethylcyclohexyl)-4,6-dimethyl-1H-indole-2-carboxamide | $^1$H NMR (400 MHz, CDCl$_3$): δ 9.06 (s, 1H), 7.05 (s, 1H), 6.78 (s, 1H), 6.77 (s, 1H), 6.06 (d, J = 8.3 Hz, 1H), 4.14-4.13 (m, 1H), 2.52 (s, 3H), 2.42 (s, 3H), 2.17-2.16 (m, 1H), 1.78-1.67 (m, 3H), 1.47-1.35 (m, 3H), 1.30 (br s, 1H), 0.92 (d, J = 6.8 Hz, 3H), 0.83 (d, J = 7.3 Hz, 3H).<br>ESI MS: m/z 299.28 (M + H).<br>HPLC purity: 98.96%. |
| 4C | 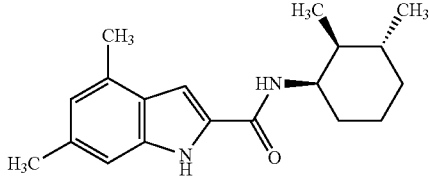<br>N-((1R,2S,3R)-2,3-dimethylcyclohexyl)-4,6-dimethyl-1H-indole-2-carboxamide | $^1$H NMR (400 MHz, CDCl$_3$): δ 9.03 (s, 1H), 7.05 (s, 1H), 6.79 (s, 1H), 6.77 (s, 1H), 6.20 (d, J = 9.27 Hz, 1H), 4.37-4.34 (m, 1H), 2.53 (s, 3H), 2.42 (s, 3H), 1.93-1.90 (m, 1H), 1.76-1.62 (m, 3H), 1.55-1.31 (m, 3H), 1.07-1.03 (m, 1H), 0.99 (d, J = 4.88 Hz, 3H), 0.97 (d, J = 3.9 Hz, 3H).<br>ESI MS: m/z 299.21 (M + H).<br>HPLC purity: 98.70%. |
| 4D | 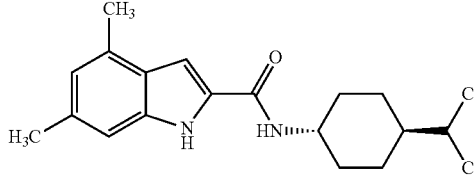<br>N-(trans-4-isopropylcyclohexyl)-4,6-dimethyl-1H-indole-2-carboxamide | $^1$H NMR (400 MHz, DMSO-d$_6$): δ 11.32 (s, 1H), 8.12 (d, J = 7.9 Hz, 1H), 7.13 (s, 1H), 7.01 (s, 1H), 6.66 (s, 1H), 3.7 (m, 1H), 2.43 (s, 3H), 2.33 (s, 3H), 1.91-1.88 (m, 2H), 1.74-1.72 (m, 2H), 1.45 (m, 1H), 1.4-1.24 (m, 2H), 1.09-1.04 (m, 3H), 0.87 (d, J = 6.6 Hz, 6H).<br>ESI MS: m/z 313.26 (M + H).<br>HPLC purity: 95.63%. |
| 4E | 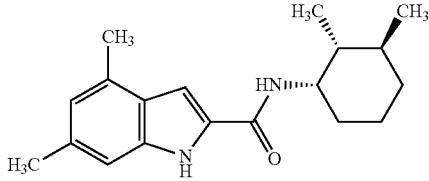<br>N-((1S,2R,3S)-2,3-dimethylcyclohexl)-4,6-dimethyl-1H-indole-2-carboxamide | $^1$H NMR (400 MHz, CDCl$_3$): δ 9.02 (s, 1H), 7.05 (s, 1H), 6.78 (s, 1H), 6.76 (d, J = 1.27 Hz, 1H), 6.20 (d, J = 8.88 Hz, 1H), 4.37-4.34 (m, 1H), 2.53 (s, 3H), 2.42 (s, 3H), 1.92-1.91 (m, 1H), 1.77-1.62 (m, 3H), 1.49-1.31 (m, 3H), 1.10-1.07 (m, 1H), 0.99 (d, J = 5.1 Hz, 3H), 0.97 (d, J = 3.81 Hz, 3H).<br>ESI MS: m/z 299.21 (M + H).<br>HPLC purity: 99.98%. |
| 4F | 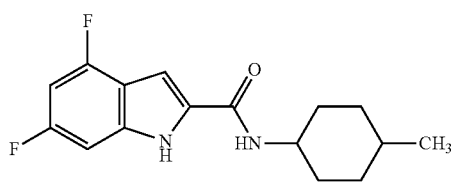<br>4,6-difluoro-N-(4-methylcyclohexyl)-1H-indole-2-carboxamide | $^1$H NMR (400 MHz, DMSO-d$_6$): δ 11.97 (s, 1H), 8.29 (d, J = 8.0 Hz, 0.41H), 8.14 (d, J = 7.7 Hz, 0.59H), 7.36 (d, J = 2.2 Hz, 0.59H), 7.26 (d, J = 2.2 Hz, 0.41H), 7.01 (d, J = 9.5 Hz, 1H), 6.91-6.85 (m, 1H), 3.96-3.90 (m, 0.59H), 3.78-3.67 (m, 0.41H), 1.87-1.82 (m, 1H), 1.75-1.30 (m, 7H), 1.08-1.0 (m, 1H), 0.95 (d, J = 6.9 Hz, 1.77H) 0.89 (d, J = 6.6 Hz, 1.23H).<br>ESI MS: m/z 293.2 (M + H).<br>HPLC purity: 99.88%.<br>(cis and trans isomeric mixture) |

TABLE 2-continued

| Example No. | Structure/Name | Analytical Data |
|---|---|---|
| 4G | 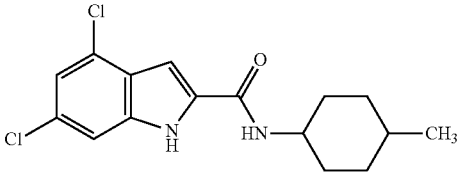<br>4,6-dichloro-N-(4-methylcyclohexyl)-1H-indole-2-carboxamide | $^1$H NMR (400 MHz, CDCl$_3$): δ 9.62 (s, 1H), 7.37 (s, 1H), 7.17 (s, 0.61H), 7.16 (s, 0.39), 6.89 (t, J = 1.0 Hz, 061H), 6.86 (t, J = 1.0 Hz, 0.39H), 6.26 (d, J = 7.5 Hz, 0.61H), 5.99 (d, J = 8.0 Hz, 0.39H), 4.30-4.20 (m, 0.61H), 4.0-3.9 (m, 0.39H), 2.14-2.06 (m, 1H), 1.86-1.08 (m, 8H), 0.99 (d, J = 6.4 Hz, 1.83H), 0.93 (d, J = 6.7 Hz, 1.17H).<br>ESI MS: m/z 325.1 (M + H).<br>HPLC purity: 99.94%.<br>(cis and trans isomeric mixture) |
| 4H | 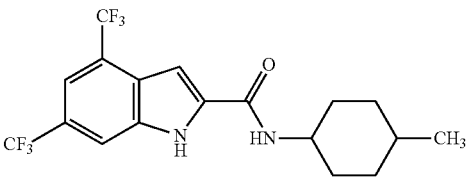<br>N-(4-methylcyclohexyl)-4,6-bis(trifluoromethyl)-1H-indole-2-carboxamide | $^1$H NMR (400 MHz, DMSO-d$_6$): δ 12.63 (s, 1H), 8.66 (d, J = 8.2 Hz, 0.40H), 8.53 (d, J = 7.0 Hz, 0.60H), 8.03 (s, 1H), 7.68 (s, 1H), 7.59 (s, 0.06H), 7.53 (s, 0.40H), 3.97-3.90 (m, 0.60H), 3.82-3.75 (m, 0.40H), 1.90-1.30 (m, 8H), 1.1-1.02 (m, 1H), 0.97 (d, J = 7.0 Hz, 1.8H), 0.90 (d, J = 6.3 Hz, 1.2H).<br>ESI MS: m/z 393.2 (M + H).<br>HPLC purity: 99.92%.<br>(cis and trans isomeric mixture) |
| 4I | 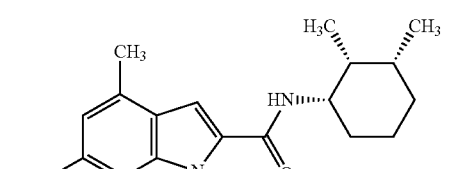<br>N-((1S,2R,3R)-2,3-dimethylcyclohexyl)-4,6-dimethyl-1H-indole-2-carboxamide | $^1$H NMR (400 MHz, CDCl$_3$): δ 8.98 (s, 1H), 7.05 (s, 1H), 6.78 (s, 1H), 6.77 (s, 1H), 6.04 (d, J = 7.5 Hz, 1H), 4.13-4.11 (m, 1H), 2.51 (s, 3H), 2.42 (s, 3H), 2.16-2.15 (m, 1H), 1.76 (br s, 2H), 1.67 (br s, 1H), 1.49-1.30 (m, 3H), 1.20-1.14 (m, 1H), 0.92 (d, J = 6.8 Hz, 3H), 0.83 (d, J = 7.52 Hz, 3H).<br>ESI MS: m/z 299.21 (M + H).<br>HPLC purity: 97.39%. |
| 4J | 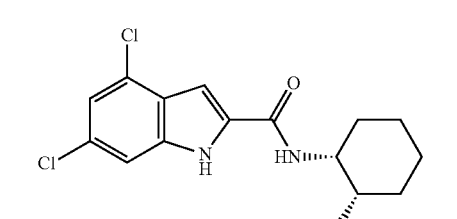<br>4,6-dichloro-N-((1R,2S)-2-methylcyclohexyl)-1H-indole-2-carboxamide | $^1$H NMR (400 MHz, CDCl$_3$): δ 10.14 (s, 1H), 7.39 (s, 1H), 7.17 (d, J = 1.6 Hz, 1H), 6.89 (d, J = 1.6 Hz, 1H), 6.25 (d, J = 8.88 Hz, 1H), 4.38-4.28 (m, 1H), 2.08-2.0 (m, 1H), 1.85-1.79 (m, 1H), 1.70-1.60 (m, 3H), 1.58-1.48 (m, 2H), 1.45-1.33 (m, 2H), 0.98 (d, J = 6.98 Hz, 3H).<br>ESI MS: m/z 325.17 (M + H).<br>HPLC purity: 96.99%. |
| 4K | 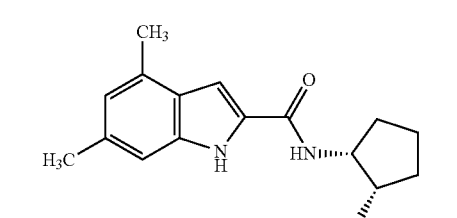<br>4,6-dimethyl-N-((1R,2S)-2-methylcyclopentyl)-1H-indole-2-carboxamide | $^1$H NMR (400 MHz, CDCl$_3$): δ 9.02 (s, 1H), 7.04 (s, 1H), 6.78 (s, 1H), 6.77 (s, 1H), 5.97 (d, J = 7.92 Hz, 1H), 4.51-4.45 (m, 1H), 2.52 (s, 3H), 2.42 (s, 3H), 2.31-2.24 (m, 1H), 2.20-2.06 (m, 1H), 1.95-1.89 (m, 1H), 1.87-1.77 (m, 1H), 1.68-1.59 (m, 2H), 1.38-1.31 (s, 1H), 0.97 (d, J = 7.30 Hz, 3H).<br>ESI MS: m/z 271.22 (M + H).<br>HPLC purity: 96.62% |

TABLE 2-continued

| Example No. | Structure/Name | Analytical Data |
|---|---|---|
| 4L | 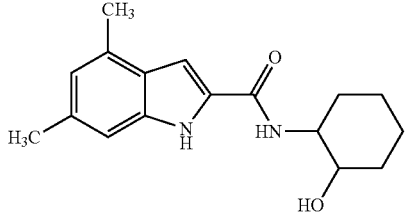<br>N-(2-hydroxycyclohexyl)-4,6-dimethyl-1H-indole-2-carboxamide | 1H NMR (400 MHz, DMSO-d6): δ 11.30 (s, 1H), 8.04 (d, J = 8.0 Hz, 1H), 7.13 (s, 1H), 7.02 (s, 1H), 6.65 (s, 1H), 4.64 (d, J = 5.2 Hz, 1H), 3.63-3.43 (m, 2H), 2.43 (s, 3H), 2.33 (m, 3H), 1.89-1.85 (m, 2H), 1.66-1.63 (m, 2H), 1.24-1.22 (m, 4H).<br>$^{13}$C NMR (100 MHz, DMSO-d6): δ 161.28, 136.58, 132.45, 130.52, 129.80, 125.20, 121.63, 109.40, 101.01, 66.73, 44.38, 34.94, 30.48, 21.45, 18.36.<br>ESI MS: m/z 287.2 [M + H].<br>HPLC purity: >99.0%.<br>(diastereomeric mixture) |
| 4M | 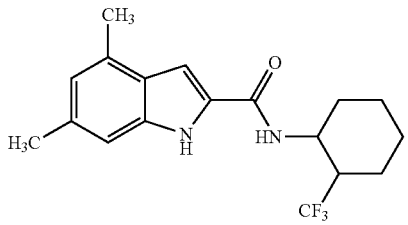<br>4,6-dimethyl-N-(2-(trifluoromethyl)cyclohexyl)-1H-indole-2-carboxamide | $^1$H NMR (400 MHz, DMSO-d$_6$): δ 11.37 (s, 1H), 7.90 (d, J = 9.6 Hz, 1H), 7.32 (s, 1H), 7.02 (s, 1H), 6.67 (s, 1H), 4.72 (dd, J = 3.33, 9.10 Hz, 1H), 2.68-2.62 (m, 1H), 2.46 (s, 3H), 2.34 (s, 3H), 2.07-1.97 (m, 1H), 1.83-1.35 (m, 7H).<br>$^{13}$C NMR (100 MHz, DMSO-d6): δ 161.12, 137.20, 133.21, 130.60, 130.53, 125.65, 122.19, 109.84, 102.81, 43.09, 42.80, 30.91, 24.13, 21.98, 18.96.<br>ESI MS: m/z 339.4 [M + H].<br>HPLC purity: >99.0%.<br>(diastereomeric mixture) |
| 4N | 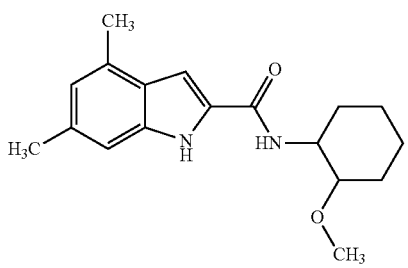<br>N-(2-methoxycyclohexyl)-4,6-dimethyl-1H-indole-2-carboxamide | $^1$H NMR (400 MHz, DMSO-d$_6$): δ 11.32 (s, 1H), 8.15 (d, J = 8.8 Hz, 1H), 7.12 (d, 1H), 7.02 (s, 1H), 6.66 (s, 1H), 3.83-3.78 (m, 1H), 3.26 (s, 3H), 3.23-3.16 (m, 1H), 2.44 (s, 3H), 2.33 (m, 3H), 2.12-2.09 (m, 1H), 1.84-1.82 (m, 1H), 1.78-1.71 (m, 2H), 1.40-1.09 (m, 4H).<br>$^{13}$C NMR (100 MHz, DMSO-d6): δ 160.56, 136.52, 132.34, 130.85, 129.77, 125.19, 121.59, 109.39, 100.89, 80.41, 55.74, 52.04, 31.64, 29.81, 24.17, 21.44, 18.40.<br>ESI MS: m/z 301.4 [M + H].<br>HPLC purity: >99.0%.<br>(diastereomeric mixture). |
| 4O | 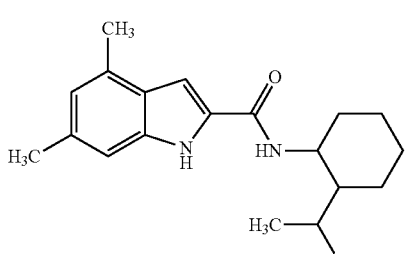<br>N-(2-isopropylcyclohexyl)-4,6-dimethyl-1H-indole-2-carboxamide | $^1$H NMR (400 MHz, DMSO-d$_6$): δ 11.36 (s, 1H), 7.50 (d, J = 9.2 Hz, 1H), 7.34 (s, 1H), 7.01 (s, 1H), 6.66 (s, 1H), 4.45-4.53 (m, 1H), 3.56-3.68 (m, 1H), 3.15-3.12 (m, 2H), 2.45 (s, 3H), 2.34 (s, 3H), 1.76-1.40 (m, 4H), 1.26-1.12 (m, 6H), 0.89-0.83 (m, 3H).<br>$^{13}$C NMR (100 MHz, DMSO-d6): δ 161.17, 137.03, 132.95, 130.79, 130.39, 125.63, 122.03, 109.69, 102.53, 54.00, 32.12, 29.56, 24.50, 21.89, 21.14, 20.98, 18.86.<br>ESI MS: m/z 313.4 [M + H].<br>HPLC purity: >96.1%.<br>(diastereomeric mixture). |

TABLE 2-continued

| Example No. | Structure/Name | Analytical Data |
|---|---|---|
| 4P | 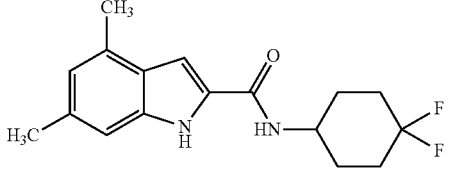<br>4,6-dichloro-N-(4,4-difluorocyclohexyl)-1H-indole-2-carboxamide | $^1$H NMR (400 MHz, DMSO-d$_6$): δ 12.09 (s, 1H), 8.51 (d, J = 7.50 Hz, 1H), 7.42 (s, 1H), 7.32 (d, J = 1.3 Hz, 1H), 7.23 (d, J = 1.3 Hz, 1H), 4.04-4.02 (m, 1H), 2.07-1.90 (m, 6H), 1.69-1.61 (m, 2H).<br>ESI MS: m/z 347.0 (M + H) & 349.0 [(M + 2) + H].<br>HPLC purity: 98.84%. |
| 4Q | 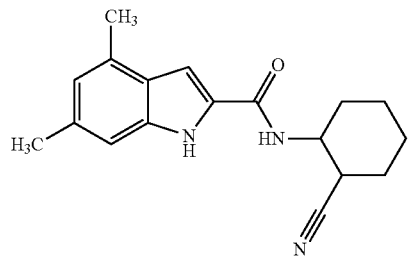<br>N-(2-cyanocyclohexyl)-4,6-dimethyl-1H-indole-2-carboxamide | $^1$H NMR (400 MHz, DMSO-d$_6$): δ 11.43 (s, 0.49H), 11.38 (s, 0.51H), 8.5-8.48 (m, 1H), 7.31 (s, 0.51H), 7.11 (s, 0.49H), 7.04 (s, 1H), 6.68 (s, 1H), 4.07-4.02 (m, 0.51H), 3.97-3.91 (m, 0.49H), 3.54-3.58 (m, 0.49H), 2.82-2.76 (m, 0.51H), 2.45 (s, 3H), 4.34 (s, 3H), 2.14-1.62 (m, 6 H), 1.41-1.35 (m, 2 H).<br>ESI MS: m/z 296.31 (M + H).<br>HPLC purity: 99.81%.<br>(diasteromeric mixture) |
| 4R | 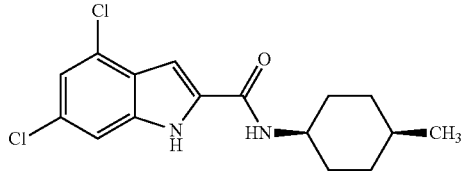<br>4,6-dichloro-N-(cis-4-methylcyclohexyl)-1H-indole-2-carboxamide | $^1$H NMR (400 MHz, DMSO-d$_6$): δ 12.03 (s, 1H), 8.26 (d, J = 7.48 Hz, 1H), 7.42 (s, 1H), 7.37 (d, J = 1.32 Hz, 1H), 7.21 (d, J = 1.81 Hz, 1H), 3.94-3.92 (m, 1H), 1.70-1.43 (m, 9H), 0.95 (d, J = 6.8 Hz, 3H).<br>ESI MS: m/z 325.23 (M + H) & 327.15 [(M + 2) + H].<br>HPLC purity: 98.05%. |
| 4S | 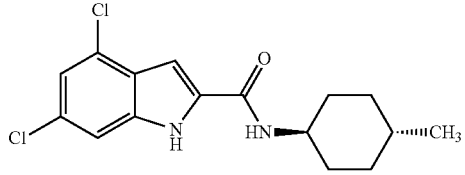<br>4,6-dichloro-N-(trans-4-methylcyclohexyl)-1H-indole-2-carboxamide | $^1$H NMR (400 MHz, DMSO-d$_6$): δ 12.01 (s, 1H), 8.40 (d, J = 7.88 Hz, 1H), 7.41 (s, 1H), 7.29 (s, 1H), 7.21 (s, 1H), 3.76-3.72 (m, 1H), 1.86-1.83 (m, 2H), 1.72-1.69 (m, 2H), 1.40-1.31 (m, 3H), 1.07-1.01 (m, 2H), 0.89 (d, J = 6.4 Hz, 3H).<br>ESI MS: m/z 325.17 (M + H) & 327.15 [(M + 2) + H].<br>HPLC purity: 98.99%. |
| 4T | 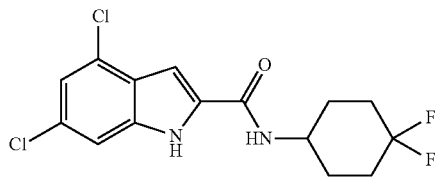<br>4,6-dichloro-N-(4,4-difluorocyclohexyl)-1H-indole-2-carboxamide | $^1$H NMR (400 MHz, DMSO-d$_6$): δ 12.09 (s, 1H), 8.51 (d, J = 7.5 Hz, 1H), 7.42 (s, 1H), 7.32 (d, J = 1.3 Hz, 1H), 7.23 (d, J = 1.3 Hz, 1H), 4.04-4.02 (m, 1H), 2.07-1.90 (m, 6H), 1.69-1.61 (m, 2H).<br>ESI MS: m/z 347.0 (M + H) & 349.0 [(M + 2) + H].<br>HPLC purity: 98.84%. |

TABLE 2-continued

| Example No. | Structure/Name | Analytical Data |
|---|---|---|
| 4U | 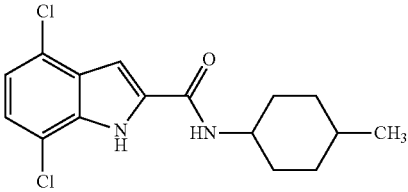<br>4,7-dichloro-N-(4-methylcyclohexyl)-1H-indole-2-carboxamide | $^1$H NMR (400 MHz, DMSO-d$_6$): δ 12.09 (s, 0.63H), 12.01 (s, 0.37H), 7.67-7.57 (m, 2H), 7.48 (s, 1H), 7.21-7.17 (m, 1H), 4.03-4.12 (m, 0.63H), 3.77-3.73 (m, 0.37H), 1.92-1.54 (m, 6H), 1.42-1.25 (m, 2H), 1.08-1.02 (m, 1H), 0.91 (d, J = 6.8 Hz, 1.89H), 0.89 (d, J = 6.8 Hz, 1.11H).<br>ESI MS: 324.9 (M + H) & 327.0 {(M + 2) + H].<br>HPLC purity: 97.05%<br>(cis and trans isomeric mixture) |
| 4V | 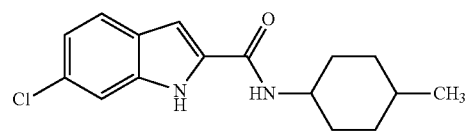<br>6-chloro-N-(4-methylcyclohexyl)-1H-indole-2-carboxamide | $^1$H NMR (400 MHz, DMSO-d$_6$): δ 11.65-11.63 (m, 1H), 8.23 (d, J = 8.0 Hz, 0.25H), 8.08 (d, J = 7.6 Hz, 0.75H), 7.64-7.61 (m, 1H), 7.43 (s, 1H), 7.24 (s, 0.75H), 7.16 (s, 0.25H), 7.05-7.03 (m, 1H), 3.94-3.92 (m, 0.75H), 3.74-3.72 (m, 0.25H), 1.86-1.31 (m, 8H), 1.07-1.01 (m, 1H), 0.95 (d, J = 6.8 Hz, 2.25H), 0.89 (d, J = 6.7 Hz, 0.75H).<br>ESI MS: m/z 291.11 (M + H).<br>HPLC purity: 99.96%.<br>(cis and trans isomeric mixture) |
| 4W | 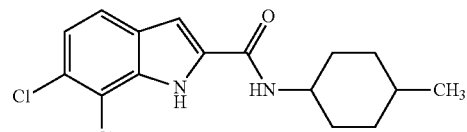<br>6,7-dichloro-N-(4-methylcyclohexyl)-1H-indole-2-carboxamide | $^1$H NMR (400 MHz, DMSO-d$_6$): δ 11.81 (s, 0.33H), 11.74 (s, 0.67H), 8.30 (d, J = 7.2 Hz, 0.67H), 8.17 (d, J = 7.2 Hz, 0.33H), 7.64-7.61 (m, 1H), 7.26-7.23 (m, 1H), 7.2 (s, 1H), 3.94 (m, 0.33H), 3.75-3.69 (m, 0.67H), 1.90-1.51 (m, 5H), 1.44-1.23 (m, 3H), 1.08-1.02 (m, 1H), 0.96 (d, J = 6.8 Hz, 0.99H), 0.90 (d, J = 6.8 Hz, 2.01H).<br>ESI MS: 325.04 (M + H) & 327.02 [(M + 2) + H].<br>HPLC purity: 98.53%.<br>(cis and trans isomeric mixture). |
| 4X | 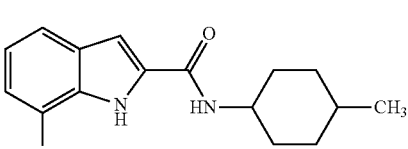<br>7-chloro-N-(4-methylcyclohexyl)-1H-indole-2-carboxamide | $^1$H NMR (400 MHz, DMSO-d$_6$): δ 11.64 (s, 0.57H), 11.56 (s, 0.43H), 8.29 (d, J = 7.2 Hz, 0.43H), 8.16 (d, J = 6.8 Hz, 0.57H), 7.62-7.59 (m, 1H), 7.30-7.28 (m, 1H), 7.22-7.18 (m, 1H), 7.08-7.04 (m, 1H), 3.95-3.94 (m, 0.57H), 3.76-3.72 (m, 0.43H), 1.91-1.51 (m, 6H), 1.44-1.29 (m, 2H), 1.08-1.02 (m, 1H), 0.96 (d, J = 6.8 Hz, 1.7H), 0.90 (d, J = 6.4 Hz, 1.29H).<br>ESI MS: 291.11 (M + H).<br>HPLC purity: 99.98%.<br>(cis and trans isomeric mixture) |

TABLE 2-continued

| Example No. | Structure/Name | Analytical Data |
|---|---|---|
| 4Y | 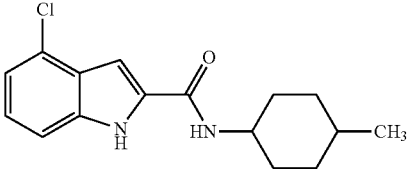<br>4-chloro-N-(4-methylcyclohexyl)-1H-indole-2-carboxamide | $^1$H NMR (400 MHz, DMSO-$d_6$): δ 12.0 (br s, 1H), 8.42 (d, J = 8.4 Hz, 0.45H), 8.28 (d, J = 7.2 Hz, 0.55H), 7.41-7.38 (m, 1H), 7.33 (s, 0.55H), 7.26 (s, 0.45H), 7.18-7.10 (m, 2H), 3.94 (m, 0.55H), 3.75-3.73 (m, 0.45H), 1.86-1.32 (m, 8H), 1.07-1.02 (m, 1H), 0.96 (d, J = 6.8 Hz, 1.65H), 0.89 (d, J = 6.4 Hz, 1.35H).<br>ESI MS: m/z 291.11 (M + H).<br>HPLC purity: 99.80%.<br>(cis and trans isomeric mixture) |
| 4Z | 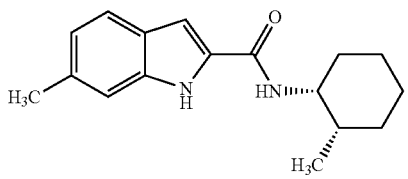<br>6-methyl-N-((1R,2S)-2-methylcyclohexyl)-1H-indole-2-carboxamide | $^1$H NMR (400 MHz, DMSO-$d_6$): δ 11.39 (s, 1H), 7.78 (d, J = 8.35 Hz, 1H), 7.47 (d, J = 7.90 Hz, 1H), 7.22 (s, 1H), 7.2 (s, 1H), 6.86 (d, J = 7.91 Hz, 1H), 4.10 (br s, 1H), 2.38 (s, 3H), 1.94 (br s, 1H), 1.68-1.48 (m, 6H), 1.38-1.33 (m, 2H), 0.87 (d, J = 6.60 Hz, 3H).<br>ESI MS: m/z 271.2 (M + H).<br>HPLC purity: 99.34%. |
| 4AA | 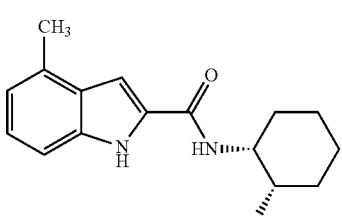<br>4-methyl-N-((1R,2S)-2-methylcyclohexyl)-1H-indole-2-carboxamide | $^1$H NMR (400 MHz, CDCl$_3$): δ 9.14 (br s, 1H), 7.28 (br s, 1H), 7.21-7.17 (m, 1H), 6.94 (d, J = 7.03 Hz, 1H), 6.83 (d, J = 0.90 Hz, 1H), 6.19 (d, J = 8.79 Hz, 1H), 4.31-4.28 (m, 1H), 2.58 (s, 3H), 1.99 (br s, 1H), 1.8 (br s, 1H), 1.79-1.61 (m, 3H), 1.53-1.32 (m, 4H), 0.97 (d, J = 6.60 Hz, 3H).<br>ESI MS: m/z 271.2 (M + H).<br>HPLC purity: 96.60%. |
| 4AB | 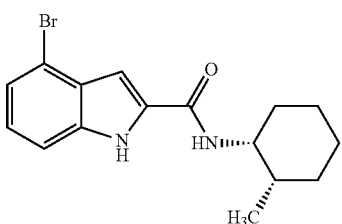<br>4-bromo-N-((1R,2S)-2-methylcyclohexyl)-1H-indole-2-carboxamide | $^1$H NMR (400 MHz, CDCl$_3$): δ 9.53 (br s, 1H), 7.39 (d, J = 8.0 Hz, 1H), 7.33 (d, J = 7.6 Hz, 1H), 7.15 (t, J = 7.86 Hz, 1H), 6.86 (d, J = 2.0 Hz, 1H), 6.24 (d, J = 8.0 Hz, 1H), 4.30 (br s, 1H), 1.99 (br s, 1H), 1.82-1.62 (m, 4H), 1.51-1.32 (m, 4H), 0.97 (d, J = 7.03 Hz, 3H).<br>ESI MS: m/z 335.08 (M + H) & 337.12 [(M + 2) + H].<br>HPLC purity: 98.04%. |
| 4AC | 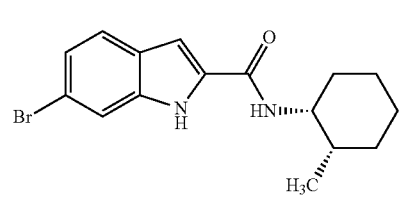<br>6-bromo-N-((1R,2S)-2-methylcyclohexyl)-1H-indole-2-carboxamide | $^1$H NMR (400 MHz, CDCl$_3$): δ 9.45 (br s, 1H), 7.61 (s, 1H), 7.51 (d, J = 8.35 Hz, 1H), 7.23 (d, J = 1.3 Hz, 1H), 6.80 (s, 1H), 6.17 (d, J = 7.91 Hz, 1H), 4.30 (br s, 1H), 1.99 (br s, 1H), 1.79-1.62 (m, 4H), 1.51-1.25 (m, 4H), 0.95 (d, J = 6.59 Hz, 3H).<br>ESI MS: m/z 335.08 (M + H) & 337.12 [(M + 2) + H].<br>HPLC purity: 98.66%. |

TABLE 2-continued

| Example No. | Structure/Name | Analytical Data |
|---|---|---|
| 4AD | 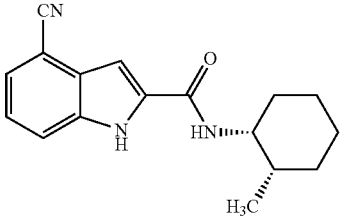<br>4-cyano-N-((1R,2S)-2-methylcyclohexyl)-1H-indole-2-carboxamide | $^1$H NMR (400 MHz, DMSO-$d_6$): δ 12.2 (s, 1H), 8.18 (d, J = 7.93 Hz, 1H), 7.76 (d, J = 8.25 Hz, 1H), 7.63-7.59 (m, 2H), 7.35-7.32 (m, 1H), 4.14 (br s, 1H), 1.97 (br s, 1H), 1.69 (br s, 2H), 1.6-1.3 (m, 6H), 0.88 (d, J = 6.98 Hz, 3H). |
| 4AE | 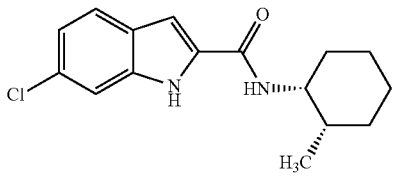<br>6-cyano-N-((1R,2S)-2-methylcyclohexyl)-1H-indole-2-carboxamide | $^1$H NMR (400 MHz, CDCl$_3$): δ 10.01 (br s, 1H), 7.81 (s, 1H), 7.72 (d, J = 7.93 Hz, 1H), 7.41-7.32 (m, 1H), 6.89 (s, 1H), 6.26 (d, J = 7.3 Hz, 1H), 4.33 (br s, 1H), 2.02 (br s, 1H), 1.8-1.66 (m, 4H), 1.46-1.2 (m, 4H), 0.97 (d, J = 6.98 Hz, 3H). |
| 4AF | 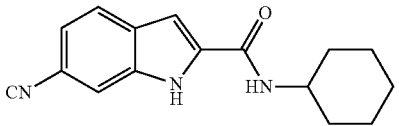<br>6-cyano-N-cyclohexyl-1H-indole-2-carboxamide | $^1$H NMR (400 MHz, DMSO-$d_6$): δ 12.08 (s, 1H), 8.42 (d, J = 7.61 Hz, 1H), 7.84 (s, 1H), 7.81 (d, J = 8.56 Hz, 2H), 7.36 (d, J = 8.24 Hz, 1H), 7.28 (s, 1H), 3.79 (br s, 1H), 1.85-1.74 (m, 4H), 1.61 (d, J = 11.73 Hz, 1H), 1.37-1.27 (m, 4H), 1.23-1.15 (m, 1H).<br>ESI MS: m/z 268.19 (M + H).<br>HPLC purity: 98.94%. |
| 4AG | 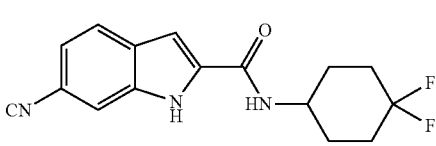<br>6-cyano-N-(4,4-difluorocyclohexyl)-1H-indole-2-carboxamide | $^1$H NMR (400 MHz, DMSO-$d_6$): δ 12.16 (s, 1H), 8.54 (d, J = 7.6 Hz, 1H), 7.84 (s, 1H), 7.82 (s, 1H), 7.37 (d, J = 8.4 Hz, 1H), 7.29 (s, 1H), 4.09-3.96 (m, 1H), 2.06-1.63 (m, 8H).<br>ESI MS: m/z 304.14 (M + H).<br>HPLC purity: 97.47%. |
| 4AH | 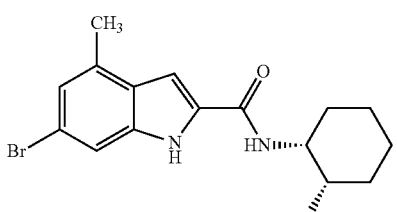<br>6-bromo-4-methyl-N-((1R,2S)-2-methylcyclohexyl)-1H-indole-2-carboxamide | $^1$H NMR (400 MHz, CDCl$_3$): δ 9.69 (s, 1H), 7.46 (s, 1H), 7.06 (s, 1H), 6.79 (s, 1H), 6.20 (d, J = 8.78 Hz, 1H), 4.40-4.25 (m, 1H), 2.54 (s, 3H), 2.05-1.98 (m, 1H), 1.83-1.62 (m, 4H), 1.58-1.30 (m, 4H), 0.97 (d, J = 6.83 Hz, 3H).<br>ESI MS: m/z 349.14 (M + H).<br>HPLC purity: 97.03%. |

TABLE 2-continued

| Example No. | Structure/Name | Analytical Data |
|---|---|---|
| 4AI | 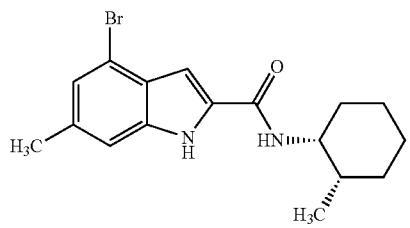<br>4-bromo-6-methyl-N-((1R,2S)-2-methylcyclohexyl)-1H-indole-2-carboxamide | $^1$H NMR (400 MHz, CDCl$_3$): δ 9.24 (s, 1H), 7.18 (s, 1H), 7.16 (s, 1H), 6.79 (s, 1H), 6.19 (d, J = 8.78 Hz, 1H), 4.35-4.25 (m, 1H), 2.45 (s, 3H), 1.98 (br s, 1H), 1.82-1.59 (m, 4H), 1.55-1.31 (m, 4H), 0.96 (d, J = 6.83 Hz, 3H).<br>ESI MS: m/z 349.14 (M + H).<br>HPLC purity: 98.69%. |
| 4AJ | 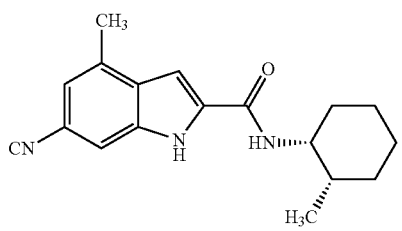<br>6-cyano-4-methyl-N-((1R,2S)-2-methylcyclohexyl)-1H-indole-2-carboxamide | $^1$H NMR (400 MHz, CDCl$_3$): δ 9.43 (br s, 1H), 7.46 (s, 1H), 7.37 (br s, 1H), 6.97 (s, 1H), 6.24 (d, J = 8.25 Hz, 1H), 4.29-4.28 (m, 1H), 2.49 (s, 3H), 2.0 (br s, 1H), 1.79-1.64 (m, 4H), 1.53-1.24 (m, 4H), 0.9 (d, J = 6.98 Hz, 3H).<br>ESI MS: m/z 296.21 (M + H).<br>HPLC purity: 99.33%. |
| 4AK | 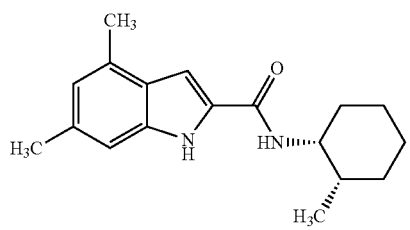<br>4-cyano-6-methyl-N-((1R,2S)-2-methylcyclohexyl)-1H-indole-2-carboxamide | $^1$H NMR (400 MHz, CDCl$_3$): δ 9.81 (s, 1H), 7.65 (s, 1H), 7.17 (s, 1H), 6.86 (d, J = 1.37 Hz, 1H), 6.26 (d, J = 8.21 Hz, 1H), 4.34-4.32 (m, 1H), 2.60 (s, 3H), 2.02 (br s, 1H), 1.82-1.65 (m, 5H), 1.45-1.25 (m, 3H). 0.98 (d, J = 6.84 Hz, 3H).<br>ESI MS: m/z 296.21 (M + H).<br>HPLC purity: 96.47%. |
| 4AL | 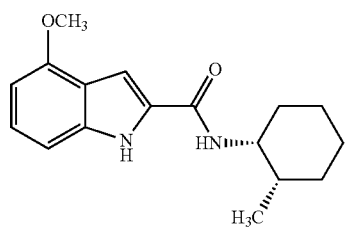<br>4-methoxy-N-((1R,2S)-2-methylcyclohexyl)-1H-indole-2-carboxamide | $^1$H NMR (400 MHz, DMSO-d$_6$): δ 11.53 (s, 1H), 7.83 (d, J = 8.25 Hz, 1H), 7.39 (s, 1H), 7.1-6.99 (m, 2H), 6.50 (d, J = 7.6 Hz, 1H), 4.1 (br s, 1H), 3.87 (s, 3H), 1.93 (br s, 1H), 1.67-1.33 (m, 8H), 0.86 (d, J = 6.98 Hz, 3H).<br>ESI MS: m/z 287.19 (M + H).<br>HPLC purity: 99.01%. |
| 4AM | 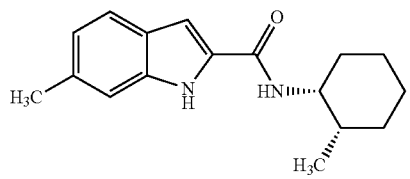<br>6-methoxy-N-((1R,2S)-2-methylcyclohexyl)-1H-indole-2-carboxamide | $^1$H NMR (400 MHz, DMSO-d$_6$): δ 9.11 (br s, 1H), 7.50 (d, J = 8.88 Hz, 1H), 6.86 (s, 1H), 6.82-6.77 (m, 2H), 6.1 (d, J = 8.2 Hz, 1H), 4.29-4.25 (m, 1H), 3.85 (s, 3H), 1.96 (br s, 1H), 1.80-1.75 (m, 1H), 1.64-1.59 (m, 3H), 1.54-1.25 (m, 4H), 0.94 (d, J = 6.83 Hz, 3H).<br>ESI MS: m/z 287.19 (M + H).<br>HPLC purity: 98.63%. |

TABLE 2-continued

| Example No. | Structure/Name | Analytical Data |
|---|---|---|
| 4AN | 4,5-dimethoxy-N-((1R,2S)-2-methylcyclohexyl)-1H-indole-2-carboxamide | $^1$H NMR (400 MHz, DMSO-d$_6$): δ 11.4 (s, 1H), 7.88 (d, J = 6.98 Hz, 1H), 7.36 (s, 1H), 7.08-6.98 (m, 2H), 4.11-4.10 (m, 1H), 3.93 (s, 3H), 3.78 (s, 3H), 1.95 (br s, 1H), 1.69-1.66 (m, 2H), 1.54-146 (m, 4H), 1.37-1.23 (m, 2H), 0.87 (d, J = 6.98 Hz, 3H). ESI MS: m/z 317.11 (M + H). HPLC purity: 99.82%. |
| 4AO | 4,6-dimethoxy-N-((1R,2S)-2-methylcyclohexyl)-1H-indole-2-carboxamide | $^1$H NMR (400 MHz, DMSO-d$_6$): δ 11.36 (s, 1H), 7.70 (d, J = 8.25 Hz, 1H), 7.31 (s, 1H), 6.46 (s, 1H), 6.16 (s, 1H), 4.08 (br s, 1H), 3.84 (s, 3H), 3.74 (s, 3H), 1.91 (br s, 1H), 1.64-1.52 (m, 2H), 1.48-1.32 (m, 6H), 0.85 (d, J = 6.98 Hz, 3H). ESI MS: m/z 317.11 (M + H). HPLC purity: 99.04%. |
| 4AP | N-((1R,2S)-2-methylcyclohexyl)-5H-[1,3]dioxolo[4,5-f]indole-6-carboxamide | $^1$H NMR (400 MHz, DMSO-d$_6$): δ 9.08 (s, 1H), 6.96 (s, 1H), 6.84 (s, 1H), 6.71 (d, J = 1.9 Hz, 1H), 6.04 (d, J = 8.88 Hz, 1H), 5.96 (s, 2H), 4.27-4.24 (m, 1H), 1.95 (br s, 1H), 1.77-1.73 (m, 1H), 1.64-1.59 (m, 3H), 1.53-1.27 (m, 4H), 0.94 (d, J = 7.0 Hz, 3H). ESI MS: m/z 301.09 (M + H). HPLC purity: 99.08%. |
| 4AQ | 5,6-dimethoxy-N-((1R,2S)-2-methylcyclohexyl)-1H-indole-2-carboxamide | $^1$H NMR (400 MHz, CDCl$_3$): δ 9.03 (br s, 1H), 7.02 (s, 1H), 6.88 (s, 1H), 6.73 (d, J = 1.59 Hz. 1H), 6.07 (d, J = 8.25 Hz, 1H), 4.28-4.25 (m, 1H), 3.94 (s, 3H), 3.92 (s, 3H), 1.97 (br s, 1H), 1.6-1.76 (m, 1H), 1.65-1.59 (m, 3H), 1.51-1.25 (m, 4H), 0.95 (d, J = 6.98 Hz, 3H). ESI MS: m/z 317.2 (M + H). HPLC purity: 99.14%. |
| 4AR | 5-methoxy-N-((1R,2S)-2-methylcyclohexyl)-1H-indole-2-carboxamide | $^1$H NMR (400 MHz, DMSO-d$_6$): δ 11.40 (s, 1H), 7.80 (d, J = 8.56 Hz, 1H), 7.31 (d, J = 8.88 Hz, 1H), 7.17 (s, 1H), 7.05 (d, J = 1.90 Hz, 1H), 6.82 (dd, J = 1.59 Hz & 7.3 Hz, 1H), 4.09 (br s, 1H), 3.75 (s, 3H), 1.95 (br s, 1H), 1.69-1.66 (m, 2H), 1.52-1.34 (m, 6H), 0.87 (d, J = 6.66 Hz, 3H). ESI MS: m/z 287.9 (M + H). HPLC purity: 98.79%. |

TABLE 2-continued

| Example No. | Structure/Name | Analytical Data |
|---|---|---|
| 4AS | 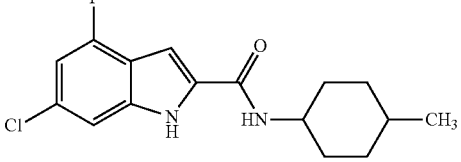<br>6-chloro-4-fluoro-N-(4-methylcyclohexyl)-1H-indole-2-carboxamide | $^1$H NMR (400 MHz, DMSO-$d_6$): δ 12.01 (s, 1H), 8.33 (d, J = 8.0 Hz, 0.39H), 8.18 (d, J = 7.2 Hz, 0.61H), 7.37-7.27 (m, 2H), 6.97 (m, 1H), 3.94-3.93 (m, 0.61H), 3.80-3.70 (m, 0.39H), 1.86-1.30 (m, 8H), 1.04-0.88 (m, 4H).<br>ESI MS: m/z 309.2 [M + H].<br>HPLC purity: >99.0%.<br>(cis and trans isomeric mixture) |
| 4AT | 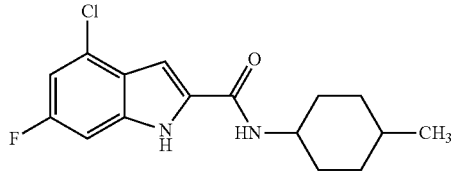<br>4-chloro-6-fluoro-N-(4-methylcyclohexyl)-1H-indole-2-carboxamide | $^1$H NMR (400 MHz, DMSO-$d_6$): δ 11.96 (s, 1H), 8.36 (d, J = 8.0 Hz, 0.39H), 8.22 (d, J = 7.2 Hz, 0.61H), 7.35 (s, 0.61H), 7.27 (s, 0.39H), 7.17-7.10 (m, 2H), 3.94-3.93 (m, 0.61H), 3.80-3.70 (m, 0.39H), 1.89-1.28 (m, 8H), 1.09-0.85 (m, 4H).<br>ESI MS: m/z 309.2 [M + H].<br>HPLC purity: >99.0%.<br>(cis and trans isomeric mixture) |
| 4AU | 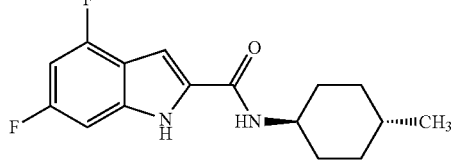<br>4,6-difluoro-N-(trans-4-methylcyclohexyl)-1H-indole-2-carboxamide | $^1$H NMR (400 MHz, DMSO-$d_6$): δ 12.8 (s, 1H), 8.28 (d, J = 7.91 Hz, 1H), 7.26 (s, 1H), 7.02-7.0 (m, 1H), 6.89-6.84 (m, 1H), 3.76-3.69 (m, 1H), 1.86-1.83 (m, 2H), 1.72-1.69 (m, 2H), 1.38-1.30 (m, 3H), 1.07-0.98 (m, 2H), 0.89 (d, J = 6.6 Hz, 3H).<br>ESI MS: m/z 293.18 (M + H).<br>HPLC purity: 99.53%. |
| 4AV | 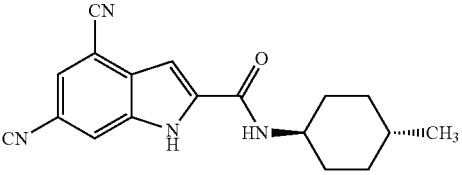<br>4,6-dicyano-N-(trans-4-methylcyclohexyl)-1H-indole-2-carboxamide | $^1$H NMR (400 MHz, DMSO-$d_6$): δ 12.79 (s, 1H), 8.68 (d, J = 8.30 Hz, 1H), 8.13-8.20 (m, 2H), 7.57 (s, 1H), 3.78-3.72 (m, 1H), 1.88-1.70 (m, 4H), 1.40-1.32 (m, 3H), 1.08-0.99 (m, 2H), 0.90-0.89 (d, J = 6.34 Hz, 3H).<br>ESI MS: 307.15 (M + H).<br>HPLC purity: 99.38%. |
| 4AW | 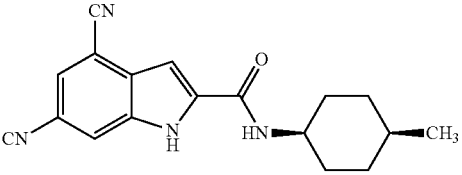<br>4,6-dicyano-N-(cis-4-methyl-cyclohexyl)-1H-indole-2-carboxamide | $^1$H NMR (400 MHz, DMSO-$d_6$): δ 12.76 (s, 1H), 8.49 (d, J = 7.32 Hz, 1H), 8.15 (s, 1H), 8.11 (s, 1H), 7.65 (s, 1H), 3.97-3.95 (m, 1H), 1.72-1.51 (m, 7H), 1.46-1.43 (m, 2H), 0.96 (d, J = 6.83 Hz, 3H).<br>ESI MS: 307.15 (M + H).<br>HPLC purity: 99.71%. |
| 4AX | 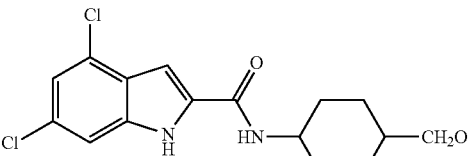<br>4,6-dichloro-N-(4-(hydroxymethyl)-cyclohexyl)-1H-indole-2-carboxamide | $^1$H NMR (400 MHz, DMSO-$d_6$): δ 12.08 (s, 1H), 8.46 (d, J = 8.0 Hz, 0.41H), 8.29 (d, J = 7.2 Hz, 0.59H), 7.41 (s, 1H), 7.35 (s, 0.59H), 7.29 (s, 0.41H), 7.21 (s, 1H), 4.45-4.40 (m, 1H), 3.95 (m, 0.59H), 3.75-3.73 (m, 0.41H), 3.37-3.33 (m, 1H), 3.25-3.22 (m, 1H), 1.89-1.78 (m, 2H), 1.63-1.50 (m, 5H), 1.37-1.23 (m, 1H), 1.04-0.94 (m, 1H).<br>ESI-MS: m/z 341.06 (M + H) & 343.14 [(M + 2) + H].<br>HPLC purity: 96.12%.<br>(cis and trans isomeric mixture). |

TABLE 2-continued

| Example No. | Structure/Name | Analytical Data |
|---|---|---|
| 4AY | 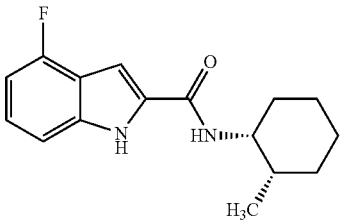<br>4-fluoro-N-((1R,2S)-2-methylcyclohexyl)-1H-indole-2-carboxamide | $^1$H NMR (400 MHz, DMSO-d$_6$): δ 11.88 (s, 1H), 7.96 (d, J = 8.4, Hz, 1H), 7.42 (s, 1H), 7.25 (d, J = 8.4 Hz, 1H), 7.17-7.12 (m, 1H), 6.81 (t, J = 8.0 Hz, 1H), 4.11 (br s, 1H), 1.95 (br s, 1H), 1.67-1.34 (m, 8H), 0.87 (d, J = 6.8 H, 3H).<br>ESI-MS: m/z 275.11 (M + H).<br>HPLC purity: 97.59%. |
| 4AZ | 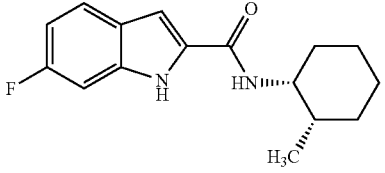<br>6-fluoro-N-((1R,2S)-2-methylcyclohexyl)-1H-indole-2-carboxamide | $^1$H NMR (400 MHz, CDCl$_3$): δ 9.56 (br s, 1H), 7.57 (q, J = 5.07 Hz, 1H), 7.12 (d, J = 9.52 Hz, 1H), 6.95-6.89 (m, 1H), 6.82 (s, 1H), 6.16 (d, J = 8.25 Hz, 1H), 4.35-4.25 (m, 1H), 1.99 (br s, 1H), 1.82-1.75 (m, 1H), 1.70-1.67 (m, 3H), 1.63-1.27 (m, 4H), 0.96 (d, J = 6.98 Hz, 3H).<br>ESI-MS: m/z 275.18 (M + H).<br>HPLC purity: 96.88%. |
| 4BA | 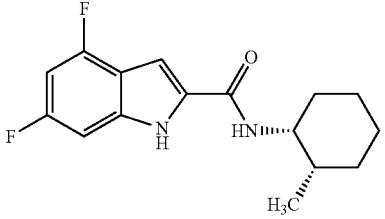<br>4,6-difluoro-N-((1R,2S)-2-methylcyclohexyl)-1H-indole-2-carboxamide | $^1$H NMR (400 MHz, DMSO-d$_6$): δ 11.98 (s, 1H), 7.97 (d, J = 8.25 Hz, 1H), 7.46 (s, 1H), 7.02 (d, J = 8.25 Hz, 1H), 6.89 (t, J = 10.15 Hz, 1H), 4.2-4.05 (m, 1H), 2.0-1.9 (s, 1H), 1.7-1.25 (m, 8H), 0.87 (d, J = 6.98 Hz, 3H).<br>ESI-MS: m/z 293.16 (M + H).<br>HPLC purity: 96.87%. |
| 4BB | 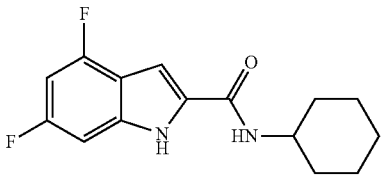<br>N-cyclohexyl-4,6-difluoro-1H-indole-2-carboxamide | $^1$H NMR (400 MHz, CD$_3$OD): δ 7.17 (s, 1H), 6.98 (d, J = 9.5 Hz, 1H), 6.68-6.60 (m, 1H), 3.87-3.82 (m, 1H), 2.02-1.78 (m, 4H), 1.72-1.65 (m, 1H), 1.45-1.18 (m, 5H).<br>ESI-MS: m/z 279.13 (M + H).<br>HPLC purity: 99.71%. |
| 4BC | 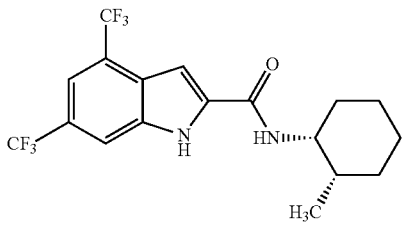<br>N-((1R,2S)-2-methylcyclohexyl)-4,6-bis(trifluoromethyl)-1H-indole-2-carboxamide | $^1$H NMR (400 MHz, CDCl$_3$): δ 10.63 (s, 1H), 7.99 (s, 1H), 7.69 (s, 1H), 7.01 (s, 1H), 6.34 (d, J = 8.4 Hz, 1H), 4.38-4.36 (m, 1H), 2.06 (br s, 1H), 1.86-1.37 (m, 8H), 1.00 (d, J = 6.8 Hz, 3H).<br>ESI-MS: m/z 393.2 (M + H).<br>HPLC purity: 97.89%. |

TABLE 2-continued

| Example No. | Structure/Name | Analytical Data |
|---|---|---|
| 4BD | 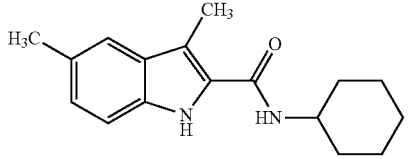<br>N-cyclohexyl-3,5-dimethyl-1H-indole-2-carboxamide | ESI-MS: m/z 270.99 (M + H).<br>HPLC purity: 99.19%. |
| 4BE | 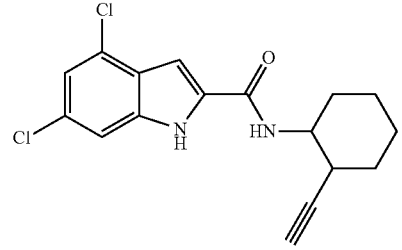<br>4,6-Dichloro-N-(2-ethynylcyclohexyl)-1H-indole-2-carboxamide | 1H NMR (400 MHz, DMSO-d6): δ 12.05 (br s, 1H), 8.29 (s, 1H), 7.33-7.51 (m, 2H), 7.23 (d, J = 1.76 Hz, 1H), 3.22 (s, 1H), 2.18 (d, J = 12.55 Hz, 2H), 1.76-1.91 (m, 2H), 1.47-1.68 (m, 5H), 1.19-1.41 (m, 1H).<br>ESI-MS: m/z 334.84 (M + H).<br>HPLC purity: 97%.<br>(diastereomeric mixture) |
| 4BF | 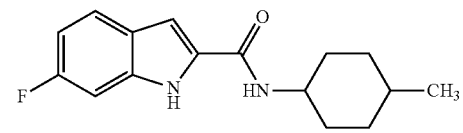<br>6-Fluoro-N-(4-methylcyclohexyl)-1H-indole-2-carboxamide | $^1$H NMR (400 MHz, CDCl$_3$): δ 9.31 (s, 1H), 7.60-7.50 (m, 1H), 7.10 (d, J = 9.2 Hz, 1H), 6.95-6.87 (m, 1H), 6.81 (d, J = 1.27 Hz, 0.65H), 6.77 (d, J = 1.27 Hz, 0.35H), 6.19 (d, J = 7.29 Hz, 0.65H), 5.89 (d, J = 8.25 Hz, 0.35H), 4.25-4.20 (m, 0.65H), 3.97-3.85 (m, 0.35H), 2.12-2.05 (m, 1H), 1.82-1.62 (m, 4H), 1.45-1.15 (m, 4H), 0.97 (d, J = 6.66 Hz, 1.95H), 0.93 (d, J = 6.34 Hz, 1.05H).<br>ESI MS: m/z 275.31 (M + H).<br>HPLC purity: 99.68%.<br>(cis and trans isomeric mixture) |
| 4BG | 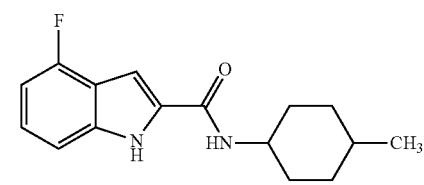<br>4-Fluoro-N-(4-methylcyclohexyl)-1H-indole-2-carboxamide | $^1$H NMR (400 MHz, DMSO-d$_6$): δ 11.88 (s, 1H), 8.28 (d, J = 7.61 Hz, 0.43H), 8.14 (d, J = 6.66 Hz, 0.57H), 7.35-7.12 (m, 3H), 6.85-6.75 (m, 1H), 3.94 (br s, 0.57H), 3.85-3.75 (m, 0.43H), 1.9-1.8 (m, 1H), 1.72-1.28 (m, 7H), 1.09-1.0 (m, 1H), 0.97-0.87 (m, 3H).<br>ESI-MS: m/z 275.18 (M + H).<br>HPLC purity: 98.5%.<br>(cis and trans isomeric mixture) |
| 4BH | 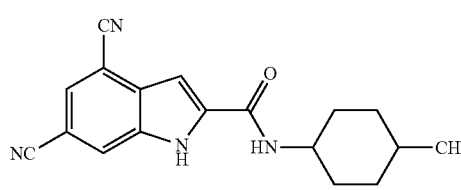<br>4-cyano-6-isocyano-N-(4-methyl-cyclohexyl)-1H-indole-2-carboxamide | $^1$H NMR (400 MHz, DMSO-d$_6$): δ 12.76 (s, 1H), 8.65 (d, J = 7.91 Hz, 0.45H), 8.49 (d, J = 7.03 Hz, 0.55H), 8.15 (d, J = 3.07 Hz, 1H), 8.11 (d, J = 1.32 Hz, 1H), 7.65 (s, 0.55H), 7.57 (s, 0.45H), 4.03-3.94 (m, 0.55H), 3.78-3.72 (m, 0.45H), 1.87-1.82 (m, 1H), 1.74-1.28 (m, 7H), 1.08-1.0 (m, 1H), 0.96 (d, J = 6.59 Hz, 1.65H), 0.9 (d, J = 6.59 Hz, 1.35H).<br>ESI-MS: m/z 307.15 (M + H).<br>HPLC purity: 99.9%.<br>(cis and trans isomeric mixture) |

Example 5

The compounds in Table 3 below were prepared using the general procedures described in Method C above with the appropriate starting materials.

mg, 1.43 mmol) in xylene (7.5 mL) were added Pd(OAc)$_2$ (58 mg, 0.26 mmol), JohnPhos (51 mg, 0.17 mmol), $^t$BuOK (644 mg, 5.74 mmol) and aniline (802 mg, 8.62 mmol). The resulting mixture was purged with argon for 10 minutes and then heated at 100° C. for 3 h in sealed tube. The reaction

TABLE 3

| Example No. | Structure/Name | Analytical Data |
|---|---|---|
| 5A | 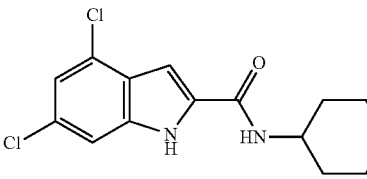<br>4,6-dichloro-N-(4-(trifluoromethyl)-cyclohexyl)-1H-indole-2-carboxamide | $^1$H NMR (400 MHz, CDCl$_3$) δ 7.35 (s, 1H), 7.18 (d, J = 1.6 Hz, 1H), 6.91 (d, J = 1.6 Hz, 1H), 6.21 (d, J = 7.2 Hz, 1H), 2.15-2.22 (m, 1H), 1.96-2.00 (m, 2H), 1.88-1.92 (m, 2H,), 1.73-1.81 (m, 2H), 1.61-1.71 (m, 3H). ESI MS: m/z 379 [M + H]$^+$. (cis and trans isomeric mixture) |
| 5B | 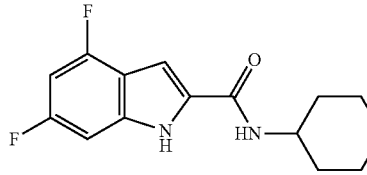<br>4,6-difluoro-N-(4-(trifluoromethyl)-cyclohexyl)-1H-indole-2-carboxamide | $^1$H NMR (400 MHz, CDCl$_3$) δ 6.93 (dd, J = 9.2 Hz, 1.6 Hz, 1H), 6.90 (d, J = 2 Hz, 1H), 6.65 (td, J = 10 Hz, 2 Hz, 1H), 6.17 (d, J = 6.8 Hz, 1H), 2.14-2.23 (m, 1H), 1.96-2.01 (m, 2H), 1.87-1.92 (m, 2H), 1.72-1.80 (m, 2H), 1.62-1.69 (m, 3H). ESI MS: m/z 347 [M + H]$^+$. (cis and trans isomeric mixture) |

Example 6

Preparation of 4-methyl-N-((1R,2S)-2-methylcyclohexyl)-6-(phenylamino)-1H-indole-2-carboxamide (6A)

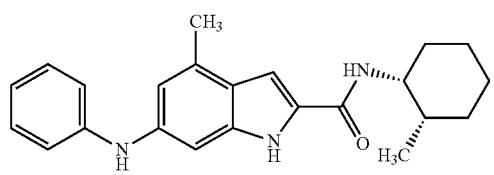

(6A)

To a stirred solution of 6-bromo-4-methyl-N-((1R,2S)-2-methylcyclohexyl)-1H-indole-2-carboxamide (4AH: 500 mg, 1.43 mmol) in xylene (7.5 mL) were added Pd(OAc)$_2$ (58 mg, 0.26 mmol), JohnPhos (51 mg, 0.17 mmol), $^t$BuOK (644 mg, 5.74 mmol) and aniline (802 mg, 8.62 mmol). The resulting mixture was purged with argon for 10 minutes and then heated at 100° C. for 3 h in sealed tube. The reaction mixture was partitioned between ethyl acetate and water. The organic layer separated and washed with brine and dried over Na$_2$SO$_4$, concentrated. The crude product was purified by column chromatography followed by preparative HPLC to obtain 160 mg of 4-methyl-N-((1R,2S)-2-methylcyclohexyl)-6-(phenylamino)-1H-indole-2-carboxamide (6A: 30%) as an off-white solid.

$^1$H NMR (400 MHz, CDCl$_3$): δ 8.98 (s, 1H), 7.3-7.27 (m, 2H), 7.09 (d, J=8.2 Hz, 2H), 6.99 (s, 1H), 6.95-6.90 (m, 1H), 6.76 (s, 1H), 6.71 (s, 1H), 6.11 (d, J=8.87 Hz, 1H), 5.75 (br s, 1H), 4.28-4.25 (m, 1H), 2.52 (s, 3H), 1.97 (br s, 1H), 1.8-1.72 (m, 1H), 1.7-1.6 (m, 3H), 1.42-1.25 (m, 4H), 0.96 (d, J=6.97 Hz, 3H). ESI MS: m/z 362.19 (M+H). HPLC purity: 99.39%.

The compounds in Table 4 below were prepared using the procedures described above for Example 6A using the appropriate starting materials.

TABLE 4

| Example No. | Structure/Name | Analytical Data |
|---|---|---|
| 6B | 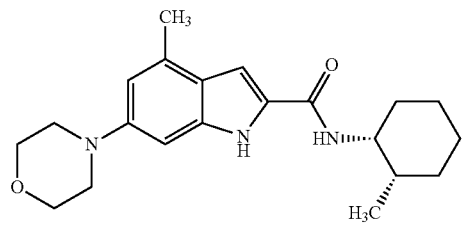<br>4-methyl-N-((1R,2S)-2-methylcyclohexyl)-6-morpholino-1H-indole-2-carboxamide | $^1$H NMR (400 MHz, CDCl$_3$): δ 8.95 (s, 1H), 6.74 (d, J = 1.27 Hz, 1H), 6.70 (s, 1H), 6.68 (s, 1H), 6.09 (d, J = 8.56 Hz, 1H), 4.3-4.22 (m, 1H), 3.89 (t, J = 4.75 Hz, 4H), 3.18 (t, J = 4.754 Hz, 4H), 2.52 (s, 3H), 1.97 (br s, 1H), 1.82-1.50 (m, 5H), 1.42-1.25 (m, 3H), 0.95 (d, J = 6.97 Hz, 3H). ESI MS: m/z 356.27 (M + H). HPLC purity: 98.36%. |

TABLE 4-continued

| Example No. | Structure/Name | Analytical Data |
|---|---|---|
| 6C | 4-methyl-N-((1R,2S)-2-methylcyclohexyl)-6-(piperidin-1-yl)-1H-indole-2-carboxamide | $^1$H NMR (400 MHz, CDCl$_3$): δ 8.95 (s, 1H), 6.73 (s, 2H), 6.69 (s, 1H), 6.09 (d, J = 8.24 Hz, 1H), 4.3-4.22 (m, 1H), 3.15 (t, J = 5.7 Hz, 4H), 2.5 (s, 3H), 1.97 (br s, 1H), 1.82-1.71 (m, 5H), 1.66-1.59 (m, 4H), 1.55-1.48 (m, 2H), 1.44-1.25 (m, 3H), 0.95 (d, J = 6.97 Hz, 3H). ESI MS: m/z 354.26 (M + H). HPLC purity: 97.07%. |
| 6D | 6-(ethylamino)-4-methyl-N-((1R,2S)-2-methylcyclohexyl)-1H-indole-2-carboxamide | $^1$H NMR (400 MHz, CDCl$_3$): δ 8.81 (s, 1H), 6.71 (s, 1H), 6.37 (s, 1H), 6.35 (s, 1H), 6.05 (d, J = 8.24 Hz, 1H), 4.27 (br s, 1H), 3.22-3.15 (m, 2H), 2.46 (s, 3H), 1.95 (br s, 1H), 1.8-1.20 (m, 11H), 0.95 (d, J = 6.97 Hz, 3H). ESI MS: m/z 314.3 (M + H). HPLC purity: 98.82%. |
| 6E | 6-(isopropylamino)-4-methyl-N-((1R,2S)-2-methylcyclohexyl)-1H-indole-2-carboxamide | $^1$H NMR (400 MHz, CDCl$_3$): δ 8.83 (s, 1H), 6.70 (d, J = 1.58, 1H), 6.35 (s, 1H), 6.30 (s, 1H), 6.05 (d, J = 8.87 Hz, 1H), 4.3-4.22 (m, 1H), 3.7-3.6 (m, 1H), 3.5 (br s, 1H), 2.45 (s, 3H), 2.0-1.95 (m, 1H), 1.82-1.74 (m, 1H), 1.66-1.61 (m, 3H), 1.56-1.48 (m, 2H), 1.43-1.29 (m, 2H), 1.23 (d, J = 6.34 Hz, 6H), 0.95 (d, J = 6.97 Hz, 3H). ESI MS: m/z 328.21 (M + H). HPLC purity: 97.26%. |

Example 7

Preparation of 4-Methyl-N-((1R,2S)-2-methylcyclohexyl)-6-morpholino-1H-indole-2-carboxamide (7A)

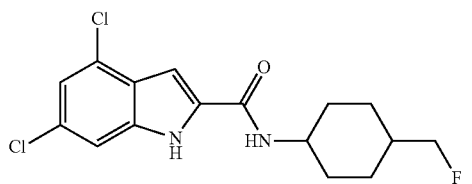

(7A)

Step 1: Preparation of Intermediate (4-(4,6-Dichloro-1H-indole-2-carboxamido)-cyclohexyl) methyl 4-methylbenzenesulfonate (I-7A-a)

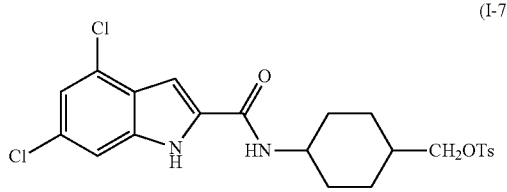

(I-7A-a)

To the stirred solution of 4,6-dichloro-N-(4-(hydroxymethyl)cyclohexyl)-1H-indole-2-carboxamide (4AX: 100 mg, 0.29 mmol) in toluene (10 mL) was added triethylamine (0.08 mL, 0.58 mmol) and DMAP (3.6 mg, 0.03 mmol). The reaction mixture was cooled to 0° C. then p-tosyl chloride (112 mg, 0.58 mmol) was added portion wise. The resulting white turbid solution was allowed to warm to room temperature and stirred for 16 h. The reaction mixture was diluted with water and extracted with ethyl acetate (2×20 mL). The combined organic phase was washed with brine, dried over anhydrous Na$_2$SO$_4$ and concentrated under reduced pressure. The crude compound was purified by column chromatography over silica gel (100-200 mesh) using a solvent gradient of 50% ethyl acetate in petroleum ether as eluent to afford 70 mg (48%) of cis and trans isomeric mixture of (4-(4,6-dichloro-1H-indole-2-carboxamido)cyclohexyl)-methyl 4-methylbenzenesulfonate (I-7A-a) as an off-white solid.

ESI MS: m/z 494.9 (M+H) & 496.9 [(M+2)+H].

Final Step: Preparation of 4,6-Dichloro-N-(4-(fluoromethyl)cyclohexyl)-1H-indole-2-carboxamide (7A)

A stirred solution of (4-(4,6-dichloro-1H-indole-2-carboxamido)-cyclohexyl)methyl 4-methylbenzenesulfonate (I-7A-a: 60 mg, 0.12 mmol) in dry THF (10 mL) was cooled to 0° C. followed by the addition of 1M TBAF (190 mg, 0.72 mmol) in THF slowly. The reaction mixture was heated to reflux for 16 h and cooled to room temperature. The mixture was then quenched with cold water and the aqueous phase was extracted with ethyl acetate (30 mL). The combined organic phase was washed with brine, dried over anhydrous Na$_2$SO$_4$ and concentrated under reduced pressure. The crude compound was purified by column chromatography over silica gel (100-200 mesh) using a solvent gradient of 10% ethyl acetate in petroleum ether as eluent to afford 20 mg (50%) of cis and trans isomeric mixture of 4,6-dichloro-N-(4-(fluoromethyl)cyclohexyl)-1H-indole-2-carboxamide (7A) as an off-white solid.

$^1$H NMR (400 MHz, DMSO-d$_6$): δ 12.08 (s, 1H), 8.50 (d, J=8.0 Hz, 0.36H), 8.29 (d, J=6.8 Hz, 0.64H), 7.41 (s, 1H), 7.38 (s, 0.64H), 7.31 (s, 0.36H), 7.23 (s, 1H), 4.46 (d, J=6.4 Hz, 0.64H), 4.34 (d, J=6.4 Hz, 1H), 4.21 (d, J=6.0 Hz, 0.36H), 4.0 (m, 0.64H), 3.77-3.75 (m, 0.36H), 1.92-1.57 (m, 7H), 1.41-1.33 (m, 1H), 1.17-1.08 (m, 1H).

ESI MS: m/z 343.01 (M+H) & 344.96 [(M+2)+H]. HPLC purity: 98.12%.

Example 8

Preparation of 4,6-Dichloro-N-(4-(methoxymethyl)cyclohexyl)-1H-indole-2-carboxamide (8A)

(8A)

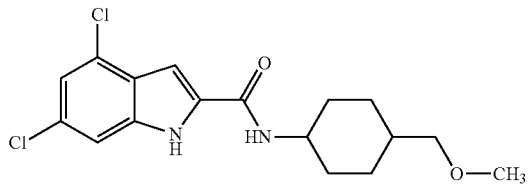

To a stirred suspension of sodium methoxide (54.6 mg, 1.01 mmol) in methanol (10 mL) was added (4-(4,6-dichloro-1H-indole-2-carboxamido)cyclohexyl)methyl 4-methylbenzenesulfonate (I-7A-a: 100 mg, 0.20 mmol). The resulting reaction mixture was heated to reflux for 24 h. The reaction mixture was cooled to room temperature, evaporated to dryness and diluted with water. The aqueous phase was extracted with ethyl acetate (2×20 mL). The combined organic layer was washed with water, brine, dried over anhydrous Na$_2$SO$_4$ solution and concentrated under reduced pressure. The crude compound was purified by column chromatography over silica gel (100-200 mesh) using a solvent gradient of 20% ethyl acetate in petroleum ether as eluent to afford 35 mg (49%) of cis and trans isomeric mixture of 4,6-dichloro-N-(4-(methoxymethyl)cyclohexyl)-1H-indole-2-carboxamide (A) as a white solid.

$^1$H NMR (400 MHz, DMSO-d$_6$): δ 12.02 (s, 1H), 8.43 (d, J=8.0 Hz, 0.52H), 8.26 (d, J=7.2 Hz, 0.48H), 7.41 (s, 1H), 7.36 (s, 0.48H), 7.30 (s, 0.52H), 7.21 (s, 1H), 3.97 (m, 0.52H), 3.76-3.74 (m, 0.48H), 3.26-3.15 (m, 5H), 1.89-1.76 (m, 3H), 1.66-1.54 (m, 4H), 1.38-1.30 (m, 1H), 1.08-1.0 (m, 1H). ESI MS: m/z 355.08 (M+H) & 357.06 [(M+2)+H]. HPLC purity: 98.11%.

Example 9

Preparation of N-Cyclohexyl-4-methyl-6-(2-morpholinoethoxy)-1H-indole-2-carboxamide (9A)

(9A)

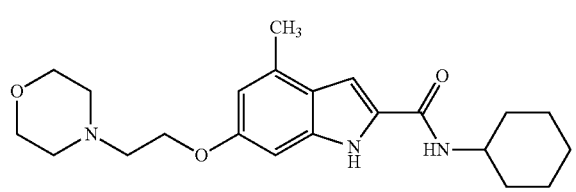

Step 1: Preparation of Intermediate 6-(benzyloxy)-N-cyclohexyl-4-methyl-1H-indole-2-carboxamide (I-9A-a)

(I-9A-a)

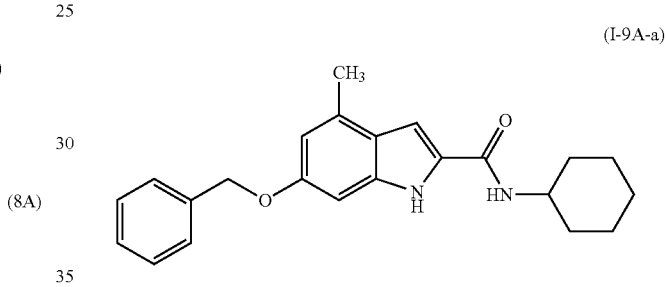

Intermediate I-9A-a was prepared according to method B in general procedure.

ESI MS: m/z 363.23 (M+H)

Step 2: Preparation of Intermediate N-cyclohexyl-6-hydroxy-4-methyl-1H-indole-2-carboxamide (I-9A-b)

(I-9A-b)

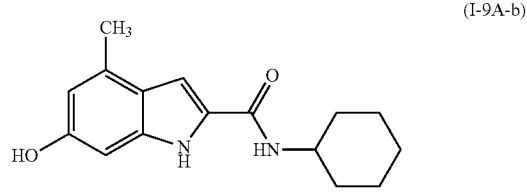 [SMILES: Cc1cc(O)cc2[nH]c(C(=O)NC3CCCCC3)cc12]

To a solution of 6-(benzyloxy)-N-cyclohexyl-4-methyl-1H-indole-2-carboxamide (I-9A-a: 1.5 g, 4.14 mmol) in ethanol (30 mL) was added 10% Pd—C (300 mg) and the mixture placed in a Parr hydrogenator (50 psi) at room temperature for 6 h. The reaction mixture was filtered through celite pad and washed with ethanol (30 mL), concentrated under reduced pressure to afford 1.2 g (90%) of N-cyclohexyl-6-hydroxy-4-methyl-1H-indole-2-carboxamide (I-9A-b) as an off-white solid.

ESI MS: m/z 273.28 (M+H).

Step 3: Preparation of Intermediate 6-(2-bromoethoxy)-N-cyclohexyl-4-methyl-1H-indole-2-carboxamide (I-9A-c)

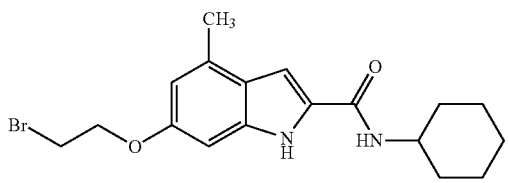

To a stirred solution of N-cyclohexyl-6-hydroxy-4-methyl-1H-indole-2-carboxamide (I-9A-b: 0.7 g, 2.57 mmol) in acetonitrile (20 mL) was added $Cs_2CO_3$ (1.67 g, 5.14 mmol) cooled to 0° C. followed by 1,2-dibromoethane (1.1 mL, 12.86 mmol) dropwise. The reaction mixture was stirred at room temperature for 16 h, diluted with water (20 mL) and extracted with ethyl acetate (2×100 mL). The combined ethyl acetate layers were washed with brine (100 mL), dried over anhydrous $Na_2SO_4$ and concentrated under reduced pressure. The crude compound was purified by column chromatography over silica gel (100-200 mesh) using a solvent gradient of 50% ethyl acetate in petroleum ether as eluent to afford 200 mg (21%) of 6-(2-bromoethoxy)-N-cyclohexyl-4-methyl-1H-indole-2-carboxamide (I-9A-c) as an off-white solid.

ESI MS: m/z 379.12 (M+H).

Final Step: Preparation of N-cyclohexyl-4-methyl-6-(2-morpholinoethoxy)-1H-indole-2-carboxamide (9A)

To a stirred solution of 6-(2-bromoethoxy)-N-cyclohexyl-4-methyl-1H-indole-2-carboxamide (I-9A-c: 0.1 g, 0.26 mmol) in acetonitrile (5 mL) at 0° C. was added $Cs_2CO_3$ (172.7 mg, 0.53 mmol) followed by morpholine (46.12 mg, 0.53 mmol) dropwise. The resulting reaction mixture was stirred at room temperature for 16 h, diluted with water (10 mL) and extracted with ethyl acetate (2×20 mL). The combined ethyl acetate layers were washed with brine (20 mL), dried over anhydrous $Na_2SO_4$ and concentrated under reduced pressure. The crude compound was purified by preparative HPLC to afford 70 mg (70%) of N-cyclohexyl-4-methyl-6-(2-morpholinoethoxy)-1H-indole-2-carboxamide (9A) as a white solid.

$^1$H NMR (400 MHz, $CDCl_3$): δ 9.10 (s, 1H), 6.75 (s, 1H), 6.69 (s, 1H), 6.63 (s, 1H), 5.95 (d, J=7.92 Hz, 1H), 4.13 (t, J=5.67 Hz, 2H), 3.99-3.97 (m, 1H), 3.75 (t, J=4.84 Hz, 4H), 2.83 (t, J=5.71 Hz, 2H), 2.60-2.49 (m, 7H), 2.06-2.03 (m, 2H), 1.79-1.63 (m, 3H), 1.45-1.42 (m, 2H), 1.39-1.20 (m, 3H). ESI MS: m/z 386.26 (M+H). HPLC purity: 99.62%.

Pharmacological Data

The utility of the compounds of the present invention may be evidenced by using any one of the assays described herein below.

The following abbreviations used herein below have the corresponding meanings:
Mtb: *Mycobacterium tuberculosis*
TB: Tuberculosis
H37Rv: Laboratory strain of Mtb from ATCC (catalogue #27294)
ATCC: American type culture collection
ADS: Albumin: Dextrose: Sodium chloride
DMSO: Dimethyl sulfoixde
MoA: Mechanism of action
MIC: Minimum inhibitory concentration
Bacterial Strain, Culture Media and Chemicals

*Mycobacterium tuberculosis* H37Rv (ATCC #27294) (Mtb) strain was maintained in Middlebrook 7H9 broth medium supplemented with 0.05% Tween 80 and 10% ADS supplement. ADS supplement contains 5% bovine serum albumin fraction V. 2% D-dextrose and 0.8% of sodium chloride. Middlebrook 7H11 agar medium supplemented with 10% OADC (oleic acid, albumin, dextrose and catalase) was used as solid media for growing Mtb. Stock solutions of the compounds were prepared using 90% DMSO.

Minimum Inhibitory Concentration ($MIC_{50}$) Determination

In Table 5 below, $MIC_{50}$ is defined as the lowest concentration of the compound that inhibited 50% growth of the wild type strain compared to untreated controls. Test compounds were two or three fold serially diluted in duplicates and spotted by mosquito HTS to 384-well clear plates, resulting in 10 dilutions of each compound. A volume of 50 μl of Mtb culture (final $OD_{600}$ of 0.02) was added to each well, and the assay plates were incubated at 37° C. for 5 days. Growth of bacteria was measured by reading absorbance at 600 nM using a Spectramax M2 spectrophotometer. $MIC_{50}$ values were determined by using Activity Base software.

TABLE 5

| Example No. | Name | $MIC_{50}$ (μmol I-1) |
|---|---|---|
| 1A | 4,6-Dichloro-N-(4,4-dimethylcyclohexyl)-1H-indole-2-carboxamide | 0.015 |
| 2A | N-(4,4-Dimethylcyclohexyl)-4,6-difluoro-1H-indole-2-carboxamide (2A): | 0.023 |
| 3A | N-(4-Isopropylphenyl)-4,6-dimethyl-1H-indole-2-carboxamide | 8.67 |
| 3B | N-(4-Chlorophenyl)-4,6-dimethyl-1H-indole-2-carboxamide | 2.95 |
| 3C | N-(4-Fluorophenyl)-4,6-dimethyl-1H-indole-2-carboxamide | 2.45 |
| 3D | N-Isopentyl-4,6-dimethyl-1H-indole-2-carboxamide | 3.26 |
| 3E | 4,6-Dimethyl-N-(4-phenylbutan-2-yl)-1H-indole-2-carboxamide | 5.74 |
| 3F | 4,6-Dimethyl-N-(pentan-3-yl)-1H-indole-2-carboxamide | 4.33 |
| 3G | N-Cycloheptyl-4,6-dimethyl-1H-indole-2-carboxamide | 0.098 |
| 3H | 4,6-Dimethyl-N-(2-methylcyclohexyl)-1H-indole-2-carboxamide | 0.32 |
| 3I | 4,6-Dimethyl-N-(2-methylbutyl)-1H-indole-2-carboxamide | 2.48 |
| 3J | N-Isobutyl-4,6-dimethyl-1H-indole-2-carboxamide | 11.85 |
| 3K | 4,6-Dimethyl-N-(p-tolyl)-1H-indole-2-carboxamide | 5.64 |
| 3L | 4,6-Dimethyl-N-(o-tolyl)-1H-indole-2-carboxamide | 3.12 |
| 3M | N-(sec-Butyl)-4,6-dimethyl-1H-indole-2-carboxamide | 9.33 |
| 3N | N-(Cyclohexylmethyl)-4,6-dimethyl-1H-indole-2-carboxamide | 0.87 |
| 4A | 4,6-Dimethyl-N-((1R,2S)-2-methylcyclohexyl)-1H-indole-2-carboxamide | 0.07 |
| 4B | N-((1R,2S,3S)-2,3-Dimethylcyclohexyl)-4,6-dimethyl-1H-indole-2-carboxamide | 0.01 |
| 4C | N-((1R,2S,3R)-2,3-Dimethylcyclohexyl)-4,6-dimethyl-1H-indole-2-carboxamide | 0.03 |
| 4D | N-(trans-4-Isopropylcyclohexyl)-4,6-dimethyl-1H-indole-2-carboxamide | 0.03 |

TABLE 5-continued

| Example No. | Name | MIC$_{50}$ (µmol I-1) |
|---|---|---|
| 4E | N-((1S,2R,3S)-2,3-Dimethylcyclohexyl)-4,6-dimethyl-1H-indole-2-carboxamide | 0.08 |
| 4F | 4,6-Difluoro-N-(4-methylcyclohexyl)-1H-indole-2-carboxamide | 0.37 |
| 4G | 4,6-Dichloro-N-(4-methylcyclohexyl)-1H-indole-2-carboxamide | 0.057 |
| 4H | N-(4-Methylcyclohexyl)-4,6-bis(trifluoromethyl)-1H-indole-2-carboxamide | 0.32 |
| 4I | N-((1S,2R,3R)-2,3-Dimethylcyclohexyl)-4,6-dimethyl-1H-indole-2-carboxamide | 0.02 |
| 4J | 4,6-Dichloro-N-((1R,2S)-2-methylcyclohexyl)-1H-indole-2-carboxamide | 0.035 |
| 4K | 4,6-Dimethyl-N-((1R,2S)-2-methylcyclopentyl)-1H-indole-2-carboxamide | 0.69 |
| 4L | N-(2-Hydroxycyclohexyl)-4,6-dimethyl-1H-indole-2-carboxamide | 2.924 |
| 4M | 4,6-Dimethyl-N-(2-(trifluoromethyl)cyclohexyl)-1H-indole-2-carboxamide | 0.585 |
| 4N | N-(2-Methoxycyclohexyl)-4,6-dimethyl-1H-indole-2-carboxamide | 5.78 |
| 4O | N-(2-Isopropylcyclohexyl)-4,6-dimethyl-1H-indole-2-carboxamide | 0.765 |
| 4P | 4,6-Dichloro-N-(4,4-difluorocyclohexyl)-1H-indole-2-carboxamide | 0.565 |
| 4Q | N-(2-Cyanocyclohexyl)-4,6-dimethyl-1H-indole-2-carboxamide | 2.06 |
| 4R | 4,6-Dichloro-N-(cis-4-methylcyclohexyl)-1H-indole-2-carboxamide | 0.14 |
| 4S | 4,6-Dichloro-N-(trans-4-methylcyclohexyl)-1H-indole-2-carboxamide | 0.14 |
| 4T | 4,6-Dichloro-N-(4,4-difluorocyclohexyl)-1H-indole-2-carboxamide | 0.565 |
| 4U | 4,7-Dichloro-N-(4-methylcyclohexyl)-1H-indole-2-carboxamide | 8.42 |
| 4V | 6-Chloro-N-(4-methylcyclohexyl)-1H-indole-2-carboxamide | 0.20 |
| 4W | 6,7-Dichloro-N-(4-methylcyclohexyl)-1H-indole-2-carboxamide | 0.72 |
| 4X | 7-Chloro-N-(4-methylcyclohexyl)-1H-indole-2-carboxamide | 0.9 |
| 4Y | 4-Chloro-N-(4-methylcyclohexyl)-1H-indole-2-carboxamide | 0.22 |
| 4Z | 6-Methyl-N-((1R,2S)-2-methylcyclohexyl)-1H-indole-2-carboxamide | 0.36 |
| 4AA | 4-Methyl-N-((1R,2S)-2-methylcyclohexyl)-1H-indole-2-carboxamide | 0.25 |
| 4AB | 4-Bromo-N-((1R,2S)-2-methylcyclohexyl)-1H-indole-2-carboxamide | 0.29 |
| 4AC | 6-Bromo-N-((1R,2S)-2-methylcyclohexyl)-1H-indole-2-carboxamide | 0.5 |
| 4AD | 4-Cyano-N-((1R,2S)-2-methylcyclohexyl)-1H-indole-2-carboxamide | 0.76 |
| 4AE | 6-Cyano-N-((1R,2S)-2-methylcyclohexyl)-1H-indole-2-carboxamide | 0.27 |
| 4AF | 6-Cyano-N-cyclohexyl-1H-indole-2-carboxamide | 2.275 |
| 4AG | 6-Cyano-N-(4,4-difluorocyclohexyl)-1H-indole-2-carboxamide | 3.36 |
| 4AH | 6-Bromo-4-methyl-N-((1R,2S)-2-methylcyclohexyl)-1H-indole-2-carboxamide | 0.01 |
| 4AI | 4-Bromo-6-methyl-N-((1R,2S)-2-methylcyclohexyl)-1H-indole-2-carboxamide | 0.06 |
| 4AJ | 6-Cyano-4-methyl-N-((1R,2S)-2-methylcyclohexyl)-1H-indole-2-carboxamide | 0.15 |
| 4AK | 4-Cyano-6-methyl-N-((1R,2S)-2-methylcyclohexyl)-1H-indole-2-carboxamide | 0.02 |
| 4AL | 4-Methoxy-N-((1R,2S)-2-methylcyclohexyl)-1H-indole-2-carboxamide | 1.59 |
| 4AM | 6-Methoxy-N-((1R,2S)-2-methylcyclohexyl)-1H-indole-2-carboxamide | 6.19 |
| 4AN | 4,5-Dimethoxy-N-((1R,2S)-2-methylcyclohexyl)-1H-indole-2-carboxamide | 1.02 |
| 4AO | 4,6-Dimethoxy-N-((1R,2S)-2-methylcyclohexyl)-1H-indole-2-carboxamide | 1.46 |
| 4AP | N-((1R,2S)-2-Methylcyclohexyl)-5H-[1,3]dioxolo[4,5-f]indole-6-carboxamide | 2.13 |
| 4AQ | 5,6-Dimethoxy-N-((1R,2S)-2-methylcyclohexyl)-1H-indole-2-carboxamide | 19.5 |
| 4AR | 5-Methoxy-N-((1R,2S)-2-methylcyclohexyl)-1H-indole-2-carboxamide | 7.53 |
| 4AS | 6-Chloro-4-fluoro-N-(4-methylcyclohexyl)-1H-indole-2-carboxamide | 0.23 |
| 4AT | 4-Chloro-6-fluoro-N-(4-methylcyclohexyl)-1H-indole-2-carboxamide | 0.165 |
| 4AU | 4,6-Difluoro-N-(trans-4-methylcyclohexyl)-1H-indole-2-carboxamide | 0.56 |
| 4AV | 4,6-Dicyano-N-(trans-4-methylcyclohexyl)-1H-indole-2-carboxamide | 0.225 |
| 4AW | 4,6-Dicyano-N-(cis-4-methyl-cyclohexyl)-1H-indole-2-carboxamide | >20 |
| 4AX | 4,6-Dichloro-N-(4-(hydroxymethyl)-cyclohexyl)-1H-indole-2-carboxamide | 13.485 |
| 4AY | 4-Fluoro-N-((1R,2S)-2-methylcyclohexyl)-1H-indole-2-carboxamide | 1.83 |
| 4AZ | 6-Fluoro-N-((1R,2S)-2-methylcyclohexyl)-1H-indole-2-carboxamide | 1.35 |
| 4BA | 4,6-Difluoro-N-((1R,2S)-2-methylcyclohexyl)-1H-indole-2-carboxamide | 0.28 |
| 4BB | N-Cyclohexyl-4,6-difluoro-1H-indole-2-carboxamide | >20 |
| 4BC | N-((1R,2S)-2-Methylcyclohexyl)-4,6-bis(trifluoromethyl)-1H-indole-2-carboxamide | 1.6 |
| 4BD | N-cyclohexyl-3,5-dimethyl-1H-indole-2-carboxamide | 3.51 |
| 4BE | 4,6-Dichloro-N-(2-ethynylcyclohexyl)-1H-indole-2-carboxamide | 0.22 |
| 4BF | 6-Fluoro-N-(4-methylcyclohexyl)-1H-indole-2-carboxamide | 1.62 |
| 4BG | 4-Fluoro-N-(4-methylcyclohexyl)-1H-indole-2-carboxamide | 2.13 |
| 4BH | 4-cyano-6-isocyano-N-(4-methyl-cyclohexyl)-1H-indole-2-carboxamide | 0.235 |
| 5A | 4,6-Dichloro-N-(4-(trifluoromethyl)-cyclohexyl)-1H-indole-2-carboxamide | 0.305 |
| 5B | 4,6-Difluoro-N-(4-(trifluoromethyl)-cyclohexyl)-1H-indole-2-carboxamide | 1.185 |
| 6A | 4-Methyl-N-((1R,2S)-2-methylcyclohexyl)-6-(phenylamino)-1H-indole-2-carboxamide | 0.145 |
| 6B | 4-Methyl-N-((1R,2S)-2-methylcyclohexyl)-6-morpholino-1H-indole-2-carboxamide | 14.25 |
| 6C | 4-Methyl-N-((1R,2S)-2-methylcyclohexyl)-6-(piperidin-1-yl)-1H-indole-2-carboxamide | 5.115 |
| 6D | 6-(Ethylamino)-4-methyl-N-((1R,2S)-2-methylcyclohexyl)-1H-indole-2-carboxamide | 4.855 |
| 6E | 6-(Isopropylamino)-4-methyl-N-((1R,2S)-2-methylcyclohexyl)-1H-indole-2-carboxamide | 2.924 |
| 7A | 4-Methyl-N-((1R,2S)-2-methylcyclohexyl)-6-morpholino-1H-indole-2-carboxamide (7A): | 0.14 |
| 8A | 4,6-Dichloro-N-(4-(methoxymethyl)cyclohexyl)-1H-indole-2-carboxamide | 1.51 |
| 9A | N-Cyclohexyl-4-methyl-6-(2-morpholinoethoxy)-1H-indole-2-carboxamide | 4.94 |

Various in vitro and in vivo assays can be used to show utility of the compounds of the present invention, such as bactericidal activity, activity against starvation or hypoxic non-replicating bacteria, activity against macrophage-intracellular bacteria, acute and established animal efficacy studies in diverse species like mouse, rat, guinea-pigs, rabbits, monkey, etc. See, Pethe K, et. al., "A chemical genetic screen in *Mycobacterium tuberculosis* identifies carbon-source-dependent growth inhibitors devoid of in vivo efficacy", *Nat. Commun*, 1(57), 1-8 (2010); and Wayne, L. G. In *Mycobacterium Tuberculosis Protocols*, Parish, T., Stoker, N. G., Eds., Humana Press, Totowa, N.J., pp 247-270 (2001).

Mechanism of Action (MoA):
Mode of Action Studies.

To evaluate the mode of action of indolecarboxamide compounds, spontaneous resistant mutants of Mtb were generated against selected indolecarboxamide compounds (Examples 4R and 4AU). Briefly, $10^9$ colony forming units of Mtb H37Rv were plated onto 7H11 plates containing 2.5, 5 and 10 µM concentration of Examples 4R and 4AU. These plates were incubated at 37° C. incubator for 3 weeks. Colonies formed on the plates were further sub-cultured in the absence of antibiotics and resistance to Examples 1A, 2A, 4R, 4S, and 4AU were confirmed by MIC determination. Genomic DNA from selected six spontaneous resistant isolates was isolated and subjected to whole genome sequencing using Solexa system as reported earlier by Pethe. See, Pethe K, et. al., "A chemical genetic screen in *Mycobacterium tuberculosis* identifies carbon-source-dependent growth inhibitors devoid of in vivo efficacy", *Nat. Commun*, 1(57), 1-8 (2010). Computational analysis and further capillary sequencing results revealed that the mutations in all spontaneous resistant mutants are mapped to Rv0206c gene. Five of the mutants showed single nucleotide polymorphism resulting in one of the following amino acid changes in Rv0206c namely V684G, L189R, T311I, S591I and G253E. One of the mutants showed two nucleotide changes resulting in V683G and V684G changes.

Rv0206c codes for MmpL3 protein which belongs to "Mycobacterial membrane protein Large" group, a member of the resistance, nodulation and division protein family. There are 14 MmpL proteins in Mtb, of which 'MmpL3' is an essential for viability of Mtb and it is also conserved across various *Mycobacterium* species including *M. leprae*. See, Domenech P., et. al., "Contribution of the *Mycobacterium tuberculosis* MmpL protein family to virulence and drug resistance", *Infect. Immun*, 73(6) pp 3492-3501 (2005). It is believed to be involved in transportation of essential molecules. See, Domenech P., et. al., "Contribution of the *Mycobacterium tuberculosis* MmpL protein family to virulence and drug resistance", *Infect. Immun*, 73(6) pp 3492-3501 (2005); Grzegorzewicz A E et al., "Inhibition of mycolic acid transport across the *Mycobacterium tuberculosis* plasma membrane", *Nat. Chem. Biol.* 8(4), pp 334-341 (2012); and Tahlan, K., et. al., "SQ109 targets MmpL3, a membrane transporter of trehalose monomycolate involved in mycolic acid donation to the cell wall core of *Mycobacterium tuberculosis*" *Antimicrob. Agents Chemother* 56(4), pp 1797-1809 (2012). Mmpl3 acts as a trehalose monomycolate (TMM) transporter, essential for translocation of mycolic acids into the cell envelope. See, Grzegorzewicz A E, et, al., "Inhibition of mycolic acid transport across the *Mycobacterium tuberculosis* plasma membrane" *Nat. Chem. Biol.* 8(4), pp 334-341 (2012). Recently, Tullius and co-workers also showed association of MmpL3 & MmpL11 with the uptake of heme as a source of iron. See, Wayne, L. G. *In Mycobacterium Tuberculosis Protocols*, Parish, T., Stoker, N. G., Eds., Humana Press, Totowa, N.J., pp 247-270 (2001). Recently, spontaneous resistance mutants raised against several novel chemical inhibitors have shown to have their mutations mapped to mmpL3. See, Grzegorzewicz A E, et, al., "Inhibition of mycolic acid transport across the *Mycobacterium tuberculosis* plasma membrane" *Nat. Chem. Biol.* 8(4), pp 334-341 (2012); La R, V., et, al., "MmpL3 is the cellular target of the antitubercular pyrrole derivative BM212" *Antimicrob. Agents Chemother* 56(1) pp 324-331 (2012); Scherman M. S., et. al., "Screening a library of 1600 adamantyl ureas for anti-*Mycobacterium tuberculosis* activity in vitro and for better physical chemical properties for bioavailability: *Bioorg. Med. Chem* 20(10) pp 3255-3262 (2012); Stanley, S. A., et. al., "Identification of Novel Inhibitors of *M. tuberculosis* Growth Using Whole Cell Based High-Throughput Screening" *ACS Chem. Biol.* (2012); and Tahlan, K., et. al., "SQ109 targets MmpL3, a membrane transporter of trehalose monomycolate involved in mycolic acid donation to the cell wall core of *Mycobacterium tuberculosis*" *Antimicrob. Agents Chemother* 56(4) pp 1797-1809 (2012).

What is claimed is:
1. A compound of Formula (I)

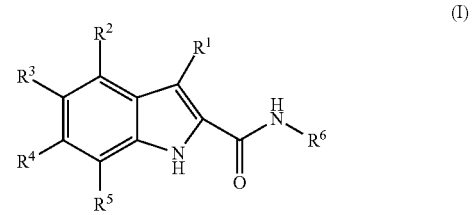

wherein:
$R^1$ is H;
$R^2$ is H, methyl, trifluoromethyl, chloro, bromo, fluoro, or cyano;
$R^3$ is H;
$R^4$ is H, methyl, trifluoromethyl, chloro, bromo, fluoro, cyano, or (phenyl)NH—;
$R^5$ is H or chloro;
provided that $R^2$, $R^3$, $R^4$ and $R^5$ are not all hydrogen;
$R^6$ is $(C_5-C_7)$cycloalkyl or —$CH_2$-(cyclohexyl), where said $(C_5-C_7)$cycloalkyl is optionally substituted with one to two substituents each independently selected from halo, methyl, isopropyl, fluoro-substituted methyl, and ethynyl, provided that $R^6$ is not an unsubstituted cyclohexyl, when $R^2$ and $R^4$ are both methyl;
or a pharmaceutically acceptable salt thereof.

2. A compound of claim 1, wherein said compound is selected from the group consisting of
N-cycloheptyl-4,6-dimethyl-1H-indole-2-carboxamide;
4-bromo-N-cycloheptyl-6-(trifluoromethyl)-1H-indole-2-carboxamide;
4,6-dimethyl-N-(2-methylcyclohexyl)-1H-indole-2-carboxamide;
N-(cyclohexylmethyl)-4,6-dimethyl-1H-indole-2-carboxamide;
4,6-dimethyl-N-((1R,2S)-2-methylcyclohexyl)-1H-indole-2-carboxamide;
4,6-dimethyl-N-((1S,2R)-2-methylcyclohexyl)-1H-indole-2-carboxamide;
N-((1R,2S,3S)-2,3-dimethylcyclohexyl)-4,6-dimethyl-1H-indole-2-carboxamide;
N-((1R,2S,3R)-2,3-dimethylcyclohexyl)-4,6-dimethyl-1H-indole-2-carboxamide;
N-(trans-4-isopropylcyclohexyl)-4,6-dimethyl-1H-indole-2-carboxamide;
N-((1S,2R,3S)-2,3-dimethylcyclohexyl)-4,6-dimethyl-1H-indole-2-carboxamide;
4,6-difluoro-N-(4-methylcyclohexyl)-1H-indole-2-carboxamide;
4,6-dichloro-N-(4-methylcyclohexyl)-1H-indole-2-carboxamide;
N-(4-methylcyclohexyl)-4,6-bis(trifluoromethyl)-1H-indole-2-carboxamide;

N-((1S,2R,3R)-2,3-dimethylcyclohexyl)-4,6-dimethyl-1H-indole-2-carboxamide;
4,6-dichloro-N-((1R,2S)-2-methylcyclohexyl)-1H-indole-2-carboxamide;
4,6-dimethyl-N-((1R,2S)-2-methylcyclopentyl)-1H-indole-2-carboxamide;
4,6-dimethyl-N-(2-(trifluoromethyl)cyclohexyl)-1H-indole-2-carboxamide;
N-(4-isopropylcyclohexyl)-4,6-dimethyl-1H-indole-2-carboxamide;
N-(2-isopropylcyclohexyl)-4,6-dimethyl-1H-indole-2-carboxamide;
4,6-dichloro-N-(4,4-difluorocyclohexyl)-1H-indole-2-carboxamide;
4,6-dichloro-N-(cis-4-methylcyclohexyl)-1H-indole-2-carboxamide;
4,6-dichloro-N-(trans-4-methylcyclohexyl)-1H-indole-2-carboxamide;
4,6-dichloro-N-(4,4-dimethylcyclohexyl)-1H-indole-2-carboxamide;
4,6-dichloro-N-(4-(trifluoromethyl)cyclohexyl)-1H-indole-2-carboxamide;
N-(4,4-Dimethylcyclohexyl)-4,6-difluoro-1H-indole-2-carboxamide;
4,6-dichloro-N-(4-(fluoromethyl)cyclohexyl)-1H-indole-2-carboxamide;
4,6-dichloro-N-(1-ethynylcyclohexyl)-1H-indole-2-carboxamide;
6-chloro-N-(4-methylcyclohexyl)-1H-indole-2-carboxamide;
6,7-dichloro-N-(4-methylcyclohexyl)-1H-indole-2-carboxamide;
7-chloro-N-(4-methylcyclohexyl)-1H-indole-2-carboxamide;
4-chloro-N-(4-methylcyclohexyl)-1H-indole-2-carboxamide;
6-methyl-N-((1R,2S)-2-methylcyclohexyl)-1H-indole-2-carboxamide;
4-methyl-N-((1R,2S)-2-methylcyclohexyl)-1H-indole-2-carboxamide;
4-bromo-N-((1R,2S)-2-methylcyclohexyl)-1H-indole-2-carboxamide;
6-bromo-N-((1R,2S)-2-methylcyclohexyl)-1H-indole-2-carboxamide;
4-cyano-N-((1R,2S)-2-methylcyclohexyl)-1H-indole-2-carboxamide;
6-cyano-N-((1R,2S)-2-methylcyclohexyl)-1H-indole-2-carboxamide;
6-bromo-4-methyl-N-((1R,2S)-2-methylcyclohexyl)-1H-indole-2-carboxamide;
4-bromo-6-methyl-N-((1R,2S)-2-methylcyclohexyl)-1H-indole-2-carboxamide;
6-cyano-4-methyl-N-((1R,2S)-2-methylcyclohexyl)-1H-indole-2-carboxamide;
4-cyano-6-methyl-N-((1R,2S)-2-methylcyclohexyl)-1H-indole-2-carboxamide;
4-methyl-N-((1R,2S)-2-methylcyclohexyl)-6-(phenylamino)-1H-indole-2-carboxamide;
6-chloro-4-fluoro-N-(4-methylcyclohexyl)-1H-indole-2-carboxamide;
4-chloro-6-fluoro-N-(4-methylcyclohexyl)-1H-indole-2-carboxamide;
4,6-dicyano-N-(trans-4-methylcyclohexyl)-1H-indole-2-carboxamide;
4,6-difluoro-N-(trans-4-methylcyclohexyl)-1H-indole-2-carboxamide;
5,6-dichloro-N-(4-methylcyclohexyl)-1H-indole-2-carboxamide;
4,6-dicyano-N-(4-methylcyclohexyl)-1H-indole-2-carboxamide; and
4,6-dichloro-N-(1-ethynylcyclohexyl)-1H-indole-2-carboxamide;

or a pharmaceutically acceptable salt thereof.

3. A compound of claim 1, wherein said compound is selected from the group consisting of
4,6-difluoro-N-(4-methylcyclohexyl)-1H-indole-2-carboxamide;
4,6-dichloro-N-(4-methylcyclohexyl)-1H-indole-2-carboxamide;
N-(4-methylcyclohexyl)-4,6-bis(trifluoromethyl)-1H-indole-2-carboxamide;
4,6-dichloro-N-((1R,2S)-2-methylcyclohexyl)-1H-indole-2-carboxamide;
4-bromo-N-cycloheptyl-6-(trifluoromethyl)-1H-indole-2-carboxamide;
5,6-dichloro-N-(4-methylcyclohexyl)-1H-indole-2-carboxamide;
4,6-dichloro-N-(cis-4-methylcyclohexyl)-1H-indole-2-carboxamide;
4,6-dichloro-N-(trans-4-methylcyclohexyl)-1H-indole-2-carboxamide;
4,6-dicyano-N-(4-methylcyclohexyl)-1H-indole-2-carboxamide;
4,6-Dichloro-N-(4,4-dimethylcyclohexyl)-1H-indole-2-carboxamide;
6-chloro-4-fluoro-N-(4-methylcyclohexyl)-1H-indole-2-carboxamide;
4-chloro-6-fluoro-N-(4-methylcyclohexyl)-1H-indole-2-carboxamide;
4,6-dichloro-N-(4-(trifluoromethyl)cyclohexyl)-1H-indole-2-carboxamide;
N-(4,4-Dimethylcyclohexyl)-4,6-difluoro-1H-indole-2-carboxamide;
4,6-dichloro-N-(4-(fluoromethyl)cyclohexyl)-1H-indole-2-carboxamide; and 4,6-difluoro-N-(trans-4-methylcyclohexyl)-1H-indole-2-carboxamide;

or a pharmaceutically acceptable salt thereof.

4. A compound of claim 1, wherein said compound is selected from the group consisting of
4,6-Dichloro-N-(4,4-dimethylcyclohexyl)-1H-indole-2-carboxamide; and
N-(4,4-Dimethylcyclohexyl)-4,6-difluoro-1H-indole-2-carboxamide;

or a pharmaceutically acceptable salt thereof.

5. A compound having the following structure

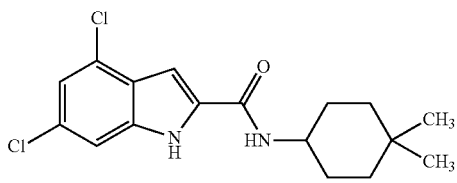 [SMILES: CC1(C)CCC(NC(=O)c2cc3c(Cl)cc(Cl)cc3[nH]2)CC1]

or a pharmaceutically acceptable salt thereof.

6. A compound having the following structure

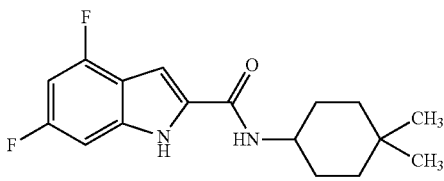 [SMILES: CC1(C)CCC(NC(=O)c2cc3c(F)cc(F)cc3[nH]2)CC1]

or a pharmaceutically acceptable salt thereof.

7. A pharmaceutical composition comprising a compound of claim 1, or a pharmaceutically acceptable salt thereof, and a pharmaceutically acceptable carrier or excipient.

8. The pharmaceutical composition of claim 7 further comprising at least one additional pharmaceutical agent.

9. The pharmaceutical composition of claim 8 wherein said at least one additional pharmaceutical agent is an antituberculosis agent.

10. The pharmaceutical composition of claim 9 wherein said antituberculosis agent is selected from the group consisting of isoniazid, rifampicin, pyrazinamide, ethambutol, streptomycin, kanamycin, amikacin, capreomycin, ofloxacin, levofloxacin, moxifloxacin, cycloserine, para-aminosalicylic acid, ethioamide, prothionamide, thioacetazone clofazimine, amoxicilin with clavulanate, imipenem, linezolid, clarithromycin, and thioridazine.

11. A method for treating a disease, disorder or syndrome mediated by the transportation of essential molecules in the mmpL3 pathway comprising the step of administering to a patient in need thereof a compound according to claim 1 or a pharmaceutically acceptable salt thereof.

12. The method of claim 11 wherein said patient is human.

13. The method of claim 12 wherein said disease, disorder or syndrome is tuberculosis.

14. The method of claim 13 wherein said essential molecules is trehalose monomycolate.

15. The method of claim 1 wherein said human has (i) a sputum smear-positive, sputum smear-negative, or extrapulmonary tuberculosis; (ii) tuberculosis caused by drug resistant *Mycobacterium tuberculosis* complex (*M. tuberculosis*) organisms; or (iii) tuberculosis combined with human immunodeficiency virus (HIV) infection.

16. A method of treating tuberculosis comprising the step of administering to a patient in need thereof a pharmaceutical composition of claim 8.

17. The method of claim 16 wherein said patient is human.

18. The method of claim 17 wherein said disease, disorder or syndrome is tuberculosis.

19. The method of claim 18 wherein said essential molecules is trehalose monomycolate.

20. A compound of claim 1, wherein $R^6$ is $(C_5-C_7)$cycloalkyl, where said $(C_5-C_7)$cycloalkyl is substituted with one to two substituents each independently selected from methyl; or a pharmaceutically acceptable salt thereof.

21. A pharmaceutical composition comprising a compound of claim 5, or a pharmaceutically acceptable salt thereof, and a pharmaceutically acceptable carrier or excipient.

22. The pharmaceutical composition of claim 21 further comprising at least one additional pharmaceutical agent.

23. The pharmaceutical composition of claim 22 wherein said at least one additional pharmaceutical agent is an antituberculosis agent.

24. The pharmaceutical composition of claim 23 wherein said antituberculosis agent is selected from the group consisting of isoniazid, rifampicin, pyrazinamide, ethambutol, streptomycin, kanamycin, amikacin, capreomycin, ofloxacin, levofloxacin, moxifloxacin, cycloserine, para-aminosalicylic acid, ethioamide, prothionamide, thioacetazone clofazimine, amoxicilin with clavulanate, imipenem, linezolid, clarithromycin, and thioridazine.

25. A pharmaceutical composition comprising a compound of claim 6, or a pharmaceutically acceptable salt thereof, and a pharmaceutically acceptable carrier or excipient.

26. The pharmaceutical composition of claim 25 further comprising at least one additional pharmaceutical agent.

27. The pharmaceutical composition of claim 26 wherein said at least one additional pharmaceutical agent is an antituberculosis agent.

28. The pharmaceutical composition of claim 27 wherein said antituberculosis agent is selected from the group consisting of isoniazid, rifampicin, pyrazinamide, ethambutol, streptomycin, kanamycin, amikacin, capreomycin, ofloxacin, levofloxacin, moxifloxacin, cycloserine, para-aminosalicylic acid, ethioamide, prothionamide, thioacetazone clofazimine, amoxicilin with clavulanate, imipenem, linezolid, clarithromycin, and thioridazine.

29. A pharmaceutical composition comprising a compound of claim 20, or a pharmaceutically acceptable salt thereof, and a pharmaceutically acceptable carrier or excipient.

30. The pharmaceutical composition of claim 29 further comprising at least one additional pharmaceutical agent.

31. The pharmaceutical composition of claim 30 wherein said at least one additional pharmaceutical agent is an antituberculosis agent.

32. The pharmaceutical composition of claim 31 wherein said antituberculosis agent is selected from the group consisting of isoniazid, rifampicin, pyrazinamide, ethambutol, streptomycin, kanamycin, amikacin, capreomycin, ofloxacin, levofloxacin, moxifloxacin, cycloserine, para-aminosalicylic acid, ethioamide, prothionamide, thioacetazone clofazimine, amoxicilin with clavulanate, imipenem, linezolid, clarithromycin, and thioridazine.

* * * * *